(12) United States Patent
Ewing et al.

(10) Patent No.: US 7,417,028 B2
(45) Date of Patent: Aug. 26, 2008

(54) HUMAN GLUCAGON-LIKE-PEPTIDE-1 MODULATORS AND THEIR USE IN TREATMENT OF DIABETES AND RELATED CONDITIONS

(75) Inventors: William R. Ewing, Yardley, PA (US); Claudio Mapelli, Plainsboro, NJ (US); Richard B. Sulsky, West Trenton, NJ (US); Tasir Shamsul Haque, Yardley, PA (US); Ving G. Lee, Hamilton, NJ (US); Douglas James Riexinger, Flemington, NJ (US); Rogelio L. Martinez, Monmouth, NJ (US); Yeheng Zhu, Stockton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 204 days.

(21) Appl. No.: 11/170,968

(22) Filed: Jun. 30, 2005

(65) Prior Publication Data

US 2006/0287242 A1    Dec. 21, 2006

Related U.S. Application Data

(60) Provisional application No. 60/585,358, filed on Jul. 2, 2004, provisional application No. 60/684,805, filed on May 26, 2005.

(51) Int. Cl.
| | |
|---|---|
| A61K 38/08 | (2006.01) |
| A61K 38/00 | (2006.01) |
| A61K 38/02 | (2006.01) |
| A61K 38/28 | (2006.01) |
| C07K 2/00 | (2006.01) |
| C07K 7/04 | (2006.01) |
| C07K 1/00 | (2006.01) |

(52) U.S. Cl. .................. 514/17; 514/2; 514/4; 514/15; 530/300; 530/327; 530/330; 530/333

(58) Field of Classification Search ........................ None
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau, II et al. |
| 5,612,359 A | 3/1997 | Murugesan |
| 5,614,492 A | 3/1997 | Habener |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |

(Continued)

FOREIGN PATENT DOCUMENTS

EP    0 142 146    5/1985

(Continued)

OTHER PUBLICATIONS

C.W. Thornber. Chem. Soc. Rev. (1979) 8(4), pp. 563-580.*

(Continued)

*Primary Examiner*—Andrew D. Kosar
(74) *Attorney, Agent, or Firm*—Brian C. Carey; Briana C. Bergen

(57) ABSTRACT

The present invention provides novel human glucagon-like peptide-1 (GLP-1)-receptor modulators that have biological activity similar or superior to native GLP-1 peptide and thus are useful for the treatment or prevention of diseases or disorders associated with GLP activity. Further, the present invention provides novel, chemically modified peptides that not only stimulate insulin secretion in type II diabetics, but also produce other beneficial insulinotropic responses. These synthetic peptide GLP-1 receptor modulators exhibit increased stability to proteolytic cleavage making them ideal therapeutic candidates for oral or parenteral administration. The peptides of this invention show desirable pharmacokinetic properties and desirable potency in efficacy models of diabetes.

22 Claims, 4 Drawing Sheets

U.S. PATENT DOCUMENTS

| | | | |
|---|---|---|---|
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,885,983 | A | 3/1999 | Biller et al. |
| 5,962,440 | A | 10/1999 | Sulsky |
| 5,998,375 | A | 12/1999 | Thøgersen et al. |
| 6,043,265 | A | 3/2000 | Murugesan et al. |
| 6,548,667 | B2 | 4/2003 | Park et al. |
| 6,737,417 | B2 | 5/2004 | Jo et al. |
| 2002/0019419 | A1 | 2/2002 | De Laszlo et al. |
| 2003/0195157 | A1 | 10/2003 | Natarajan et al. |

FOREIGN PATENT DOCUMENTS

| | | |
|---|---|---|
| EP | 0 221 025 | 5/1987 |
| FR | 2 596 393 | 10/1987 |
| GB | 2 205 837 | 12/1988 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/34332 | 6/2000 |
| WO | WO 03/033671 A | 4/2003 |
| WO | WO 2004/094461 | 11/2004 |

OTHER PUBLICATIONS

U.S. Appl. No. 11/172,488, filed Jun. 30, 2005, Mathur et al.

Ashworth, D.M. et al., "2-Cyanopyrrolidides as Potent, Stable Inhibitors of Dipeptidyl Peptidase IV", Bioorganic & Medicinal Chemistry Letters, vol. 6, No. 10, pp. 1163-1166 (1996).

Ashworth, D.M. et al., "4-Cyanothiazolidides as Very Potent, Stable Inhibitors of Dipeptidyl Peptidase IV", Bioorganic & Medicinal Chemistry Letters, vol. 6, No. 22, pp. 2745-2748 (1996).

Atheron, E. et al., Chapter 1: "The Fluorenylmethoxycarbonyl Amino Protecting Group", The Peptides: Analysis, Synthesis, Biology, vol. 9: Special Methods in Peptide Synthesis, Part C, Academic Press, Inc., publ., Udenfriend, S. et al., eds., pp. 1-38 (1987).

Barany, G. et al., Chapter 1: "Solid-Phase Peptide Synthesis", The Peptides: Analysis, Synthesis, Biology, vol. 2: Special Methods in Peptide Synthesis, Part A, Academic Press, Inc., publ., Gross, E. et al., eds., pp. 1-284 (1979).

Biller, S.A. et al., "Isoprenoid (Phoshinlmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Burgess, K. et al., "Solid Phase Syntheses of Oligoureas", J. Am. Chem. Soc., vol. 119, No. 7, pp. 1556-1564 (1997).

Byrne, M.M. et al., "Inhibitory effects of hyperglycaemia on fed jejunal motility: potential role of hyperinsulinaemia", European Journal of Clinical Investigation, vol. 28, pp. 72-78 (1998).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreactive Analogs of Terpenoid Pyrophosphates to Studies of Multistep Biosynthesis. Demostration That 'Presqualene Pyrophosphate' Is an Essential Intermediate on the Path to Squalene", Journal of the American Chemical Society, vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Davern, P. et al., "Chemical and Biological Reactivity of Sulfamidopenicillins", J. Chem. Soc. Perkin Trans. 2, pp. 381-387 (1994).

Fehder, W.P. et al., "Development and Evaluation of a Chromatographic Procedure for Partial Purification of Substance P with Quantitation by an Enzyme Immunassay", Clinical and Diagnostic Laboratory Immunology, vol. 5, No. 3, pp. 303-307 (1998).

Fehrentz, J.-A. et al., "An Efficient Synthesis of Optically Active α($t$-Butoxycarbonylamino)-aldehydes from α-Amino Acids", Synthesis, pp. 676-678 (1983).

Fingl, E. et al., Section I: "Introduction", Chapter I: "General Principles", The Pharmacological Basics of Therapeutics, $5^{th}$ Ed., Macmillan Publishing Co., Inc., publ., Goodman, L.S. et al., eds., pp. 1-46 (1975).

Flint, A. et al., "Glucagon-like Peptide 1 Promotes Satiety and Suppresses Energy Intake in Humans", J. Clin. Invest., vol. 101, No. 3, pp. 515-520 (1998).

Gennaro, A.R., ed., Remington's Pharmaceutical Sciences, $18^{th}$ Ed., Mack Publishing Company, publ., pp. xv-xvi (table of contents) (1990).

Gennaro, A.R., ed., Remington: Practice of the Science and Pharmacy, $19^{th}$ Ed., Mack Publishing Company, publ., pp. xv-xvi (table of contents) (1995).

Gennaro, A.R., ed., Reminton: Practice of the Science and Pharmacy, vol. II, $19^{th}$ Ed., Mack Publishing Company, publ., pp. vii-viii (table of contents) (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Gluschankof, P. et al., "Enzymes processing somatostatin precursors: An Arg-Lys esteropeptidase from the rat brain cortex converting somatostain-28 into somatostatin-14", Proc. Natl. Acad. Sci. USA, vol. 81, pp. 6662-6666 (1984).

Gutzwiller, J.-P. et al., "Glucagon-like peptide-1: a potent regulator of food intake in humans", Gut, vol. 44, pp. 81-86 (1999).

Hara, S., "Ileal $Na^+$/bile acid cotransporter inhibitors", Drugs of the Future, vol. 24, No. 4, pp. 425-430 (1999).

Holst, J.J., "Glucagon-like Peptide-1, A Gastrointestinal Hormone with a Pharmaceutical Potential", Current Medicinal Chemistry, vol. 6, No. 11, pp. 1005-1017 (1999).

Ito, Y. et al., "Difference in cholesterol-binding and cytolytic activities between listeriolysin O and seeligeriolysin O: a possible role of alanine residue in tryptophan-rich undecapeptide", FEMS Microbiology Letters, vol. 203, pp. 185-189 (2001).

Johannsson, G. et al., "Growth Hormone Treatment of Abdominally Obese Men Reduces Abdominal Fat Mass, Improve Glucose and Lipoprotein Metabolism, and Reduces Diastolic Blood Pressure", Journal of Clinical Endocrinology and Metabolism, vol. 82, No. 3, pp. 727-734 (1997).

King, D.S. et al., "A cleavage method which minimizes side reactions following Fmoc solid phase peptide synthesis", Int. J. Peptide Protein Res., vol. 36, pp. 255-266 (1990).

Krause, B.R. et al., Chapter 6: ACAT Inhibitors: "Physiologic Mechanisms for Hypolipidemic and Anti-Atherosclerotic Activites in Experimental Animals", Inflammation: Mediators and Pathways, CRC Press, Inc., publ., Ruffolo, Jr., R.R. et al., eds., pp. 173-198 (1995).

McClard, R.W. et al., "Novel Phosphonylphosphinyl (P-C-P-C) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptorα (PPAR-α) and PPAR-γ: Effect of PPAR-α Activation on Abnormal Lipid Metabolism in Liver of Zucker Fatty Rats", Diabetes, vol. 47, pp. 1841-1847 (1998).

Näslund, E. et al., "Energy intake and appetite are suppressed by glucagon-like peptide-1 (GLP-1) in obese men", International Journal of Obesity, vol. 23, pp. 304-311 (1999).

Nicolosi, R.J. et al., "The ACAT inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rosenblum, S.B. et al., "Dicovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of the Future, vol. 24, No. 1, pp. 9-15 (1999).

Stewart, J.M. et al., Solid Phase Peptide Synthesis, 2$^{nd}$ Ed., Pierce Chemical Company, publ., pp. vii-xi (table of contents), 92 (1984).

Stoffers, D.A. et al., "Insulinotropic Glucagon-Like Peptide 1 Agonists Stimulate Expression of Homeodomain Protein IDX-1 and Increase Islet Size in Mouse Pancreas", Diabetes, vol. 49, pp. 741-748 (2000).

Stout, D.M. et al., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity. Inhibitors of Acyl-CoA:Cholesterol Acyltransferase (ACAT). 7. Development of a Series of Substituted N-Phenyl-N+-[(1-phenylcyclopentyl)-methyl]ureas with Enhanced Hypocholestrolemic Activity", Chemtracts—Organic Chemistry, vol. 8, pp. 359-362 (1995).

Wettergren, A. et al., "Truncated GLP-1 (Proglucagon 78-107-Amide) Inhibits Gastric and Pancreatic Functions in Man", Digestive Diseases and Sciences, vol. 38, No. 4, pp. 665-673 (1993).

Yamada, M. et al., "A Potent Dipeptide Inhibitor of Dipetidyl Peptidase IV", Bioorganic & Medicinal Chemistry Letters, vol. 8, pp. 1537-1540 (1998).

* cited by examiner

Effect of acute sc injection of ~~Compound III~~ SEQ ID NO:58 on plasma glucose in an ipGTT in ob/ob mice

HUMAN GLUCAGON-LIKE-PEPTIDE-1 MODULATORS AND THEIR USE IN TREATMENT OF DIABETES AND RELATED CONDITIONS This application claims priority to U.S. Provisional Patent Application Ser. No. 60/585,358, filed Jul. 2, 2004 and U.S. Provisional Patent Application Ser. No. 60/684,805, filed May 26, 2005, each of which is hereby incorporated by reference in its entirety.

FIELD OF THE INVENTION

The present invention provides novel human glucagon-like peptide-1 (GLP-1) peptide receptor modulators, agonists or partial agonists, which exhibit superior biological properties of the native peptide, GLP-1, and exhibit increased stability to proteolytic cleavage as compared to GLP-1 native sequences, and thus are useful for the amelioration of the diabetic condition.

BACKGROUND OF THE INVENTION

GLP-1 is an important gut hormone with regulatory function in glucose metabolism and gastrointestinal secretion and metabolism. Human GLP-1 is a 30 amino acid peptide originating from preproglucagon, which is synthesized for example, in the L-cells in the distal ileum, in the pancreas and in the brain. Processing of preproglucagon to yield GLP-1 (7-36)amide and GLP-2 occurs mainly in the L-cells and the brainstem. GLP-1 is normally secreted in response to food intake, in particular carbohydrates and lipids stimulate GLP-1 secretion. GLP-1 has been identified as a very potent and efficacious stimulator of glucose-dependent insulin release with a reduced risk to induce hypoglycemia. GLP-1 lowers plasma glucagon concentrations, slows gastric emptying, stimulates insulin biosynthesis and enhances insulin sensitivity (Nauck, 1997, *Horm. Metab. Res.* 47:1253-1258). GLP-1 also enhances the ability of the pancreatic beta-cells to sense and respond to glucose in subjects with impaired glucose tolerance (Byrne, Eur. *J. Clin. Invest.,* 28:72-78, 1998). The insulinotropic effect of GLP-1 in humans increases the rate of glucose metabolism partly due to increased insulin levels and partly due to enhanced insulin sensitivity (D'Alessio, *Eur. J. Clin. Invest.,* 28:72-78, 1994). Inhibition of glucagon release is thought to be an additional mechanism which contributes to the improvements in glucose homeostasis observed following treatment of type II diabetic patients with GLP-1 (Nauck, M. A., et al., *Diabetologia* 36:741-744, 1993). The above stated pharmacological properties of GLP-1 make it a highly desirable therapeutic agent for the treatment of type-II diabetes.

Additionally, recent studies have shown that infusions of slightly supraphysiological amounts of GLP-1 significantly enhance satiety and reduce food intake in normal subjects (Flint, A., Raben, A., Astrup, A. and Holst, J. J., *J. Clin. Invest,* 101:515-520, 1998; Gutswiller, J. P., Goke, B., Drewe, J., Hildebrand, P., Ketterer, S., Handschin, D., Winterhaider, R., Conen, D and Beglinger, C. *Gut* 44:81-86, 1999). The effect on food intake and satiety has also been reported to be preserved in obese subjects (Naslund, E., Barkeling, B., King, N., Gutniak, M., Blundell, J. E., Holst, J. J., Rossner, S., and Hellstrom, P. M., *Int. J. Obes. Relat. Metab. Disord.,* 23:304-311, 1999).

In the above-cited studies a pronounced effect of GLP-1 on gastric emptying was also suspected to occur. Gastric emptying results in post-prandial glucose excursions. It has also been shown that in addition to stimulation of insulin secretion, GLP-1 stimulates the expression of the transcription factor, islet-duodenal homeobox-1 (IDX-1), while stimulating B-cell neogenesis and may thereby be an effective treatment and/or preventive agent for diabetes (Stoffers, D. A., Kieffer, T. J. Hussain, M. A., Drucker, D. J., Bonner-Weir, S., Habener, J. F. and Egan, J. M. *Diabetes,* 40:741-748, 2000). GLP-1 has also been shown to inhibit gastric acid secretion (Wettergren, A., Schjoldager, B., Mortensen, P. E., Myhre, J., Christiansen, J., Holst, J. J., *Dig. Dis. Sci.,* 38:665-673, 1993), which may provide protection against gastric ulcers.

It has recently been reported that GLP-1 has a number of additional extra-pancreatic effects that could, for example, result in cardioprotection, neuroprotection, and induction of learning and memory (reviewed in Ahren, B., *Horm. Metab. Res.* 36:842-845, 2004). Therefore, it has also been proposed that GLP-1 could be used in the treatment of heart failure (Nikolaidis, L. A., et al., *Circulation* 110:955-961, 2004), ischemia/reperfusion injury (Nikolaidis, L. A., et al., *Circulation* 109:962-965, 2004), and Alzheimer's Disease (Perry, T. and Greig, N. H., *J. Alzheimers Dis.* 4:487-496, 2002).

GLP-1 is an incretin hormone, for example, an intestinal hormone that enhances meal-induced insulin secretion (Holst, J. J., *Curr. Med. Chem.,* 6:1005-1017, 1999). It is a product of the glucagon gene encoding proglucagon. This gene is expressed not only in the A-cells of the pancreas but also in the endocrine L-cells of the intestinal mucosa. Proglucagon is a peptide (protein) containing 160 amino acids. Further processing of proglucagon results in the generation of a) glucagon, b) an N-terminal, presumably inactive fragment, and c) a large C-terminal fragment commonly referred as "the major proglucagon fragment". This fragment is considered to be biologically inactive. Even though this fragment is present in both pancreas and in the L-cells of the gut, it is only in the intestines the breakdown products of the "the major proglucagon fragment" resulting in two highly homologous peptides commonly referred as GLP-1 and GLP-2 are observed. These two peptides have important biological activities. As such, the amino acid sequence of GLP-1, which is present in the L-cells, is identical to the 78-107 portion of proglucagon.

Presently, therapy involving the use of GLP-1-type molecules has presented a significant problem because the serum half-life of such peptides is quite short. For example, GLP-1 (7-37) has a serum half-life of less than 5 minutes. Thus there exists a critical need for biologically active GLP-1 receptor modulators, agonists or antagonists, that possess extended pharmacodynamic profiles. It is to this and other needs that the present invention is directed.

The present invention therefore provides novel peptides that act as GLP-1 receptor modulators, agonists or partial agonists, which exhibit similar or superior biological properties of the native peptide, GLP-1, and thus are useful for the amelioration of the diabetic and related conditions.

SUMMARY OF THE INVENTION

In one aspect, the present invention is directed to an isolated polypeptide comprising a polypeptide having a sequence of Formula I:

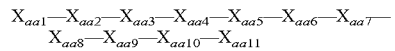

wherein, $X_{aa1}$ is a naturally or nonnaturally occurring amino acid comprising an imidazole; wherein one or more carbon atoms of the amino acid are optionally substituted with one or more alkyl groups; wherein the amino acid optionally has a free amino group which is optionally substituted with alkyl, acyl, benzoyl, L-lactyl, alkyloxycarbonyl, aryloxycarbonyl, aralkyloxycarbonyl, heterocyclyloxycarbonyl, heteroarylalkyloxycarbonyl, alkylcarbamoyl, arylcarbamoyl, arylalkylcarbamoyl, heterocyclylsulfonyl, alkylsulfonyl, arylsulfonyl, arylalkylsulfonyl, heteroarylalkylsulfonyl or heteroarylsulfonyl; and wherein when the free amino group is not present $X_{aa1}$ is the des-amino acid of histidine in which one or more carbon atoms of the amino acid are optionally substituted with one or more alkyl groups;

$X_{aa2}$ is a naturally or nonnaturally occurring amino acid selected from the group consisting of D-alanine, α-aminoisobutyric acid (Aib), N-methyl-D-alanine, N-ethyl-D-alanine, 2-methyl-azetidine-2-carboxylic acid, alpha-methyl-(L)-proline, 2-methylpiperidine-2-carboxylic acid and isovaline;

$X_{aa3}$ is a naturally or nonnaturally occurring amino acid having (1) an amino acid side chain comprising a carboxylic acid or (2) an imidazole side chain, and wherein one or more carbon atoms of the amino acid is optionally substituted with one or more alkyl groups;

$X_{aa4}$ is glycine;

$X_{aa5}$ is a naturally or nonnaturally occurring amino acid selected from the group consisting of (L)-threonine and (L)-norvaline; and wherein one or more carbon atoms of the amino acid is optionally substituted with one or more alkyl groups;

$X_{aa6}$ is a naturally or nonnaturally occurring amino acid having a disubstituted alpha carbon having two side chains; wherein at least one of the two side chains has an aromatic ring and at least one of the two chains has an alkyl group; and wherein one or more carbon atoms of the amino acid is optionally substituted with one or more alkyl groups or one or more halo groups.

$X_{aa7}$ is a naturally or nonnaturally occurring amino acid having an amino acid side chain which is substituted with a hydroxyl group; and wherein one or more carbon atoms of the amino acid is optionally substituted with one or more alkyl groups;

$X_{aa8}$ is a naturally or nonnaturally occurring amino acid selected from the group consisting of L-serine and L-histidine; and wherein one or more carbon atoms of the amino acid is optionally substituted with one or more alkyl groups;

$X_{aa9}$ is a naturally or nonnaturally occurring amino acid having an amino acid side chain comprising a carboxylic acid; and wherein one or more carbon atoms of the amino acid is optionally substituted with one or more alkyl groups;

$X_{aa10}$ is a naturally or nonnaturally occurring amino acid of Formula II:

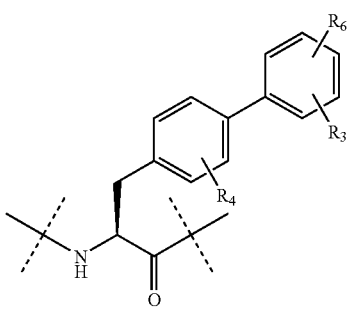

Formula II wherein $R_4$ is selected from the group consisting of hydrogen, alkyl, and halo;

wherein $R_3$ and $R_6$ are each independently selected from the group consisting of hydrogen, halo, methyl, ethyl, alkyl, hydroxyl, methoxy, and alkoxy;

wherein the phenyl ring proximal to the beta-carbon of the amino acid is additionally optionally substituted with alkyl or halo; and wherein the phenyl ring distal to the beta-carbon of the amino acid is additionally optionally substituted with halo, methyl, ethyl, alkyl, hydroxyl, methoxy, and alkoxy;

$X_{aa11}$ is a naturally or nonnaturally occurring amino acid of Formula IVa:

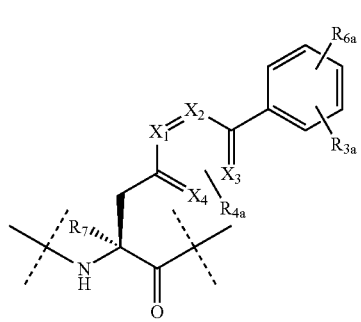

Formula IVa wherein the C-terminal carbonyl carbon of said amino acid is attached to a nitrogen to form a carboxamide ($NH_2$);

wherein $R_{4a}$ is selected from the group consisting of hydrogen, alkyl, and halo;

wherein $R_{3a}$ and $R_{6a}$ are each independently selected from the group consisting of hydrogen, halo, methyl, ethyl, alkyl, hydroxyl, methoxy, and alkoxy;

wherein $R_7$ is selected from the group consisting of hydrogen, methyl, and ethyl; and wherein $X_1$, $X_2$, $X_3$ and $X_4$ are each C or N, with the proviso that at least one of $X_1$, $X_2$, $X_3$ and $X_4$ is N;

wherein the phenyl ring proximal to the beta-carbon of the amino acid is additionally optionally substituted with alkyl or halo; and wherein the phenyl ring distal to the beta-carbon of the amino acid is additionally optionally substituted with halo, methyl, ethyl, alkyl, hydroxyl, methoxy, and alkoxy.

Further, $Xaa_3$ may be histidine, wherein the histidine is optionally substituted with one or more alkyl groups. $X_{aa3}$ may be L-aspartic acid or L-glutamic acid, wherein each of the L-aspartic acid or L-glutamic acid is optionally substituted with one or more alkyl groups.

$X_{aa6}$ may be alpha-methyl-phenylalanine, alpha-methyl-2-fluorophenylalanine, or alpha-methyl-2,6-difluorophenylalanine, wherein each of the alpha-methyl-phenylalanine, alpha-methyl-2-fluorophenylalanine, or alpha-methyl-2,6-difluorophenylalanine is optionally substituted with one or more alkyl groups.

$X_{aa7}$ may be L-threonine, wherein the threonine is optionally substituted with one or more alkyl groups.

$X_{aa9}$ may be L-aspartic acid or L-glutamic acid, wherein each of the L-aspartic acid or L-glutamic acid is optionally substituted with one or more alkyl groups.

$X_{aa1}$ may be L-histidine, the histidine having a terminal amino group which is optionally substituted with alkyl, dialkyl, acyl, benzoyl, L-lactyl, alkyloxycarbonyl, aryloxycarbonyl, aralkyloxycarbonyl, heterocyclyloxycarbonyl, heteroarylalkyloxycarbonyl, alkylcarbamoyl, arylcarbamoyl, aralkylcarbamoyl, heterocyclylsulfonyl, alkylsulfonyl, arylsulfonyl, arylalkylsulfonyl, heteroarylalkylsulfonyl or heteroarylsulfonyl.

$X_{aa1}$ may be selected from the group consisting of L-N-methyl-His, L-α-methyl-His, des-amino-His, 3-(1H-imidazol-4-yl)-2-methylpropanoyl, and (S)-3-(1H-imidazol-4-yl)-2-hydroxypropanoyl(L-β-imidazolelactyl).

$X_{aa2}$ may be selected from the group consisting of α-amino-isobutyric acid (Aib), D-alanine, N-methyl-D-alanine, alpha-methyl-(L)-proline, 2-methyl-azetidine-2-carboxylic acid and 2-methylpiperidine-2-carboxylic acid.

$X_{aa4}$ may be glycine.

$X_{aa5}$ may be selected from the group consisting of L-Thr, and L-Nva.

$X_{aa6}$ may be selected from the group consisting of L-α-Me-Phe, L-α-Me-2-fluoro-Phe, and L-α-Me-2,6-difluoro-Phe.

$X_{aa7}$ may be L-Thr.

$X_{aa8}$ may be selected from the group consisting of L-Ser, and L-His.

$X_{aa9}$ may be L-Asp.

$X_{aa10}$ may be selected from the group consisting of 4-phenyl-phenylalanine, 4-[(4'-methoxy-2'-ethyl)phenyl]phenylalanine, 4-[(4'-ethoxy-2'-ethyl)phenyl]phenylalanine, 4-[(4'-methoxy-2'-methyl)phenyl]phenylalanine, 4-[(4'-ethoxy-2'-methyl)phenyl]phenylalanine, 4-(2'-ethylphenyl)phenylalanine, 4-(2'-methylphenyl)phenylalanine, 4-[(3',5'-dimethyl)phenyl]phenylalanine and 4-[(3',4'-dimethoxy)phenyl]phenylalanine.

$X_{aa11}$ may be selected from the group consisting of 4-phenyl-3-pyridylalanine, 4-(2'-methylphenyl)-3-pyridylalanine, 4-(2'-fluorophenyl)-3-pyridylalanine, 4-(2'-chlorophenyl)-3-pyridylalanine, 4-[(3',5'-dimethyl)phenyl]-3-pyridylalanine, 4-(4'-trifluoromethylphenyl)-3-pyridylalanine, 4-(3'-methoxyphenyl)-3-pyridylalanine, 4-(3'-methylphenyl)-3-pyridylalanine, 4-(2'-methylphenyl)-3,5-pyrimidylalanine and 4-(2'-ethylphenyl)-3-pyridylalanine;

wherein the C-terminal carbonyl carbon of $X_{aa11}$ is attached to a nitrogen to form a carboxamide ($NH_2$); and wherein $R_7$ is selected from the group consisting of hydrogen and methyl.

In another aspect, the isolated polypeptide may be a polypeptide of Formula VI:

wherein:

$X_{aa2}$ is an amino acid selected from the group consisting of D-Ala, N-methyl-D-Ala, α-methyl-L-Pro, 2-methyl-azetidine-2-carboxylic acid, 2-methylpiperidine-2-carboxylic acid and α-aminoisobutyric (Aib);

X and Y are each independently selected from the group consisting of hydrogen and fluoro;

$X_{aa8}$ is an amino acid selected from the group consisting of L-Ser and L-His;

$R_3$ is selected from the group of hydrogen, methyl and ethyl;

$R_6$ is selected from the group of hydrogen, hydroxy, methoxy and ethoxy;

$R_{3a}$ is selected from the group of hydrogen, fluoro, methyl and ethyl;

$R_{6a}$ is selected from the group of hydrogen, methyl and methoxy; and $R_7$ is selected from the group of hydrogen and methyl.

Further, $X_{aa2}$ may be an amino acid selected from the group consisting of N-methyl-D-Ala, α-methyl-L-Pro and α-aminoisobutyric (Aib);

X may be fluoro;

Y may be hydrogen;

$X_{aa8}$ may be an amino acid selected from the group consisting of L-Ser and L-His;

$R_3$ may be ethyl;

$R_6$ may be methoxy;

$R_{3a}$ may be selected from the group consisting of methyl and ethyl;

$R_{6a}$ may be hydrogen;

$R_7$ may be hydrogen.

In another aspect, the isolated polypeptide may be a polypeptide of Formula VII:

Formula VI

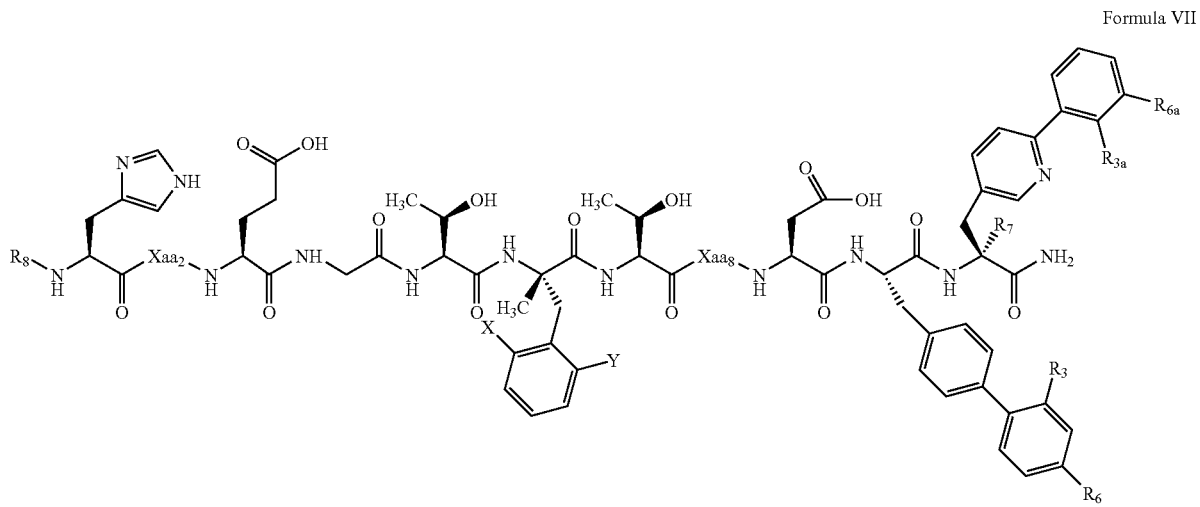

Formula VII wherein:

$R_8$ is selected from the group consisting of methyl, ethyl,

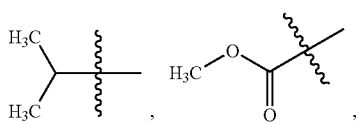

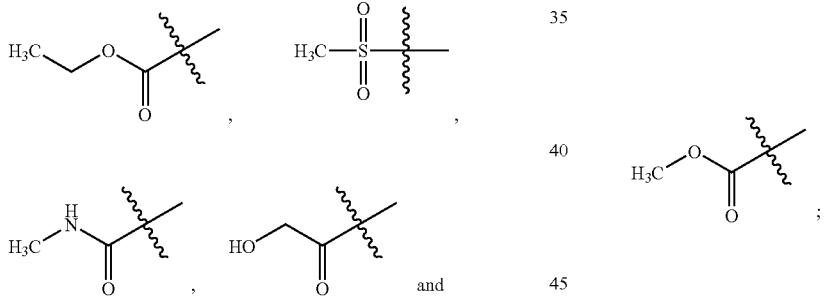
and

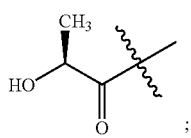;

$X_{aa2}$ is an amino acid selected from the group consisting of D-Ala, N-methyl-D-Ala, α-methyl-L-Pro, α-aminoisobutyric (Aib), 2-methyl-azetidine-2-carboxylic acid, and 2-methylpiperidine-2-carboxylic acid;

X and Y are each independently selected from the group consisting of hydrogen and fluoro;

$X_{aa8}$ is an amino acid selected from the group consisting of L-Ser and L-His;

$R_3$ is selected from the group consisting of hydrogen, methyl and ethyl;

$R_6$ is selected from the group consisting of hydrogen, hydroxy, methoxy and ethoxy;

$R_{3a}$ is selected from the group consisting of hydrogen, fluoro, methyl and ethyl;

$R_{6a}$ is selected from the group consisting of hydrogen, methyl and methoxy; and $R_7$ is selected from the group consisting of hydrogen and methyl.

Further, $R_8$ may be selected from the group consisting of methyl, and

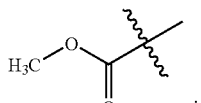;

$X_{aa2}$ may be an amino acid selected from the group consisting of N-methyl-D-Ala, α-methyl-L-Pro and aminoisobutyric acid (Aib);

X may be fluoro;

Y may be hydrogen;

$X_{aa8}$ may be an amino acid selected from the group consisting of L-Ser and L-His;

$R_3$ may be ethyl;

$R_6$ may be methoxy;

$R_{3a}$ may be selected from the group consisting of methyl and ethyl;

$R_{6a}$ may be hydrogen;

$R_7$ may be selected from the group consisting of hydrogen and methyl.

In another aspect, the isolated polypeptide may be a polypeptide of Formula VIII:

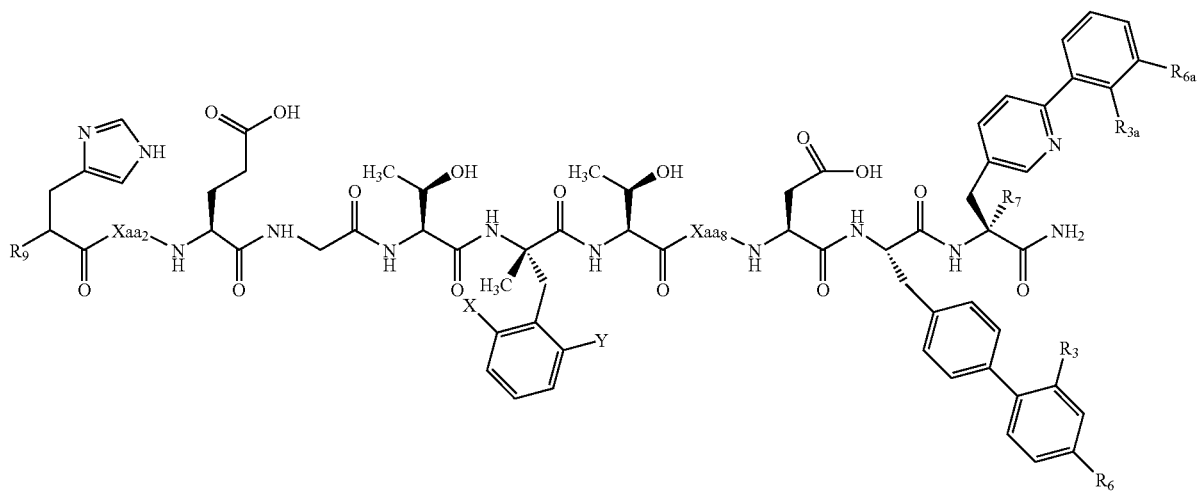

Formula VIII wherein:

R$_9$ is selected from the group consisting of hydrogen, methyl and alkyl;

X$_{aa2}$ is an amino acid selected from the group consisting of D-Ala, N-methyl-D-Ala, α-methyl-L-Pro, α-aminoisobutyric acid (Aib), 2-methyl-azetidine-2-carboxylic acid and 2-methylpiperidine-2-carboxylic acid;

X and Y are each independently selected from the group consisting of hydrogen and fluoro;

X$_{aa8}$ is an amino acid selected from the group consisting of L-Ser and L-His;

R$_3$ is selected from the group of hydrogen, methyl and ethyl;

R$_6$ is selected from the group consisting of hydrogen, hydroxy, methoxy and ethoxy;

R$_{3a}$ is selected from the group consisting of hydrogen, fluoro, methyl and ethyl;

R$_{6a}$ is selected from the group consisting of hydrogen, methyl and methoxy;

R$_7$ is selected from the group consisting of hydrogen and methyl.

Further, R$_9$ may be selected from the group consisting of hydrogen and methyl;

X$_{aa2}$ may be an amino acid selected from the group consisting of N-methyl-D-Ala, α-methyl-L-Pro, and α-aminoisobutyric acid (Aib);

X may be fluoro;

Y may be hydrogen;

X$_{aa8}$ may be an amino acid selected from the group consisting of L-Ser and L-His;

R$_3$ may be ethyl;

R$_6$ may be methoxy;

R$_{3a}$ may be selected from the group consisting of methyl and ethyl;

R$_{6a}$ may be hydrogen;

R$_7$ may be hydrogen.

In another aspect, the isolated polypeptide may be an isolated polypeptide which is a compound selected from the group of compounds in the following table:

| SEQ ID NO. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$-NH2 |
|---|---|---|---|---|---|---|---|---|---|---|---|
| 1 | H | Aib | E | G | T | L-α-Me-Phe(2-Fluoro) | T | S | D | Bip(2'-Et-4'-OMe) | 4-(2'-Methylphenyl)-3-pyridylalanine-NH2 |
| 2 | H | Aib | E | G | T | L-α-Me-Phe(2,6-di-Fluoro) | T | S | D | Bip(2'-Et-4'-OMe) | 4-(2'-Methylphenyl)-3-pyridylalanine-NH2 |
| 3 | Des-NH2-His | Aib | E | G | T | L-α-Me-Phe(2-Fluoro) | T | S | D | Bip(2'-Et-4'-OMe) | 4-(2'-Methylphenyl)-3-pyridylalanine-NH2 |
| 4 | Des-NH2-His | Aib | E | G | T | L-α-Me-Phe(2,6-di-Fluoro) | T | S | D | Bip(2'-Et-4'-OMe) | 4-(2'-Methylphenyl)-3-pyridylalanine-NH2 |

-continued

| SEQ ID NO. | X_{aa1} | X_{aa2} | X_{aa3} | X_{aa4} | X_{aa5} | X_{aa6} | X_{aa7} | X_{aa8} | X_{aa9} | X_{aa10} | X_{aa11}-NH2 |
|---|---|---|---|---|---|---|---|---|---|---|---|
| 5 | H | Aib | E | G | T | L-α-Me-Phe(2-Fluoro) | T | S | D | Bip(2'-Et-4'-OMe) | 4-(2-trifluoromethylphenyl)-3-pyridylalanine-NH2 |
| 6 | H | Aib | E | G | T | L-α-Me-Phe(2-Fluoro) | T | S | D | Bip(2'-Et-4'-OMe) | 4-(2-trifluoromethylphenyl)-3-pyridylalanine-NH2 |
| 7 | H | Aib | E | G | T | L-α-Me-Phe(2-Fluoro) | T | S | D | Bip(2'-Et-4'-OMe) | 4-[(2'-Methyl-5'-fluoro)phenyl)]-3-pyridylalanine-NH2 |
| 8 | H | Aib | E | G | T | L-α-Me-Phe(2-Fluoro) | T | S | D | Bip(2'-Et-4'-OMe) | 4-(4'-methanesulfonylphenyl)-3-pyridylalanine-NH2 |
| 9 | H | Aib | E | G | T | L-α-Me-Phe | T | S | D | Bip(2'-Et-4'-OMe) | 4-(2'-Methylphenyl)-3-pyridylalanine-NH2 |
| 10 | H | Aib | E | G | T | L-α-Me-Phe(2-Fluoro) | T | S | D | Bip(2'-Et) | 4-(2'-Methylphenyl)-3-pyridylalanine-NH2 |
| 11 | H | Aib | E | G | Nle | L-α-Me-Phe(2-Fluoro) | T | S | D | Bip(2'-Et-4'-OMe) | 4-(2'-Methylphenyl)-3-pyridylalanine-NH2 |
| 12 | H | Aib | E | G | T | L-α-Me-Phe(2,6-di-Fluoro) | T | S | D | Bip(2'-Cl) | 4-(2'-Methylphenyl)-3-pyridylalanine-NH2 |
| 13 | H | Aib | E | G | T | L-α-Me-Phe(2,6-di-Fluoro) | T | S | D | Bip(2',4'-di-OMe) | 4-(2'-Methylphenyl)-3-pyridylalanine-NH2 |
| 14 | H | Aib | E | G | T | L-α-Me-Phe(2,6-di-Fluoro) | T | S | D | Bip(2'-Me-3'-F) | 4-(2'-Methylphenyl)-3-pyridylalanine-NH2 |
| 15 | H | Aib | E | G | T | L-α-Me-Phe(2,6-di-Fluoro) | T | S | D | Bip(2'-Me-3'-F) | 4-(2'-Methylphenyl)-3-pyridylalanine-NH2 |
| 16 | H | Aib | E | G | T | L-α-Me-Phe(2-Fluoro) | T | S | D | Bip(2'-F) | 4-(2'-Methylphenyl)-3-pyridylalanine-NH2 |
| 17 | H | Aib | E | G | T | L-α-Me-Phe(2,6-di-Fluoro) | T | S | D | 4-[(2'-Cl-4'-CF3)-3'-pyridyl]-phenylalanine | 4-(2'-Methylphenyl)-3-pyridylalanine-NH2 |
| 18 | H | Aib | E | G | Nva | L-α-Me-Phe(2-Fluoro) | T | S | D | Bip(2'-Et-4'-OMe) | 4-(2'-Methylphenyl)-3-pyridylalanine-NH2 |
| 19 | H | Aib | E | G | T | L-α-Me-Phe(2-Fluoro) | T | S | D | Bip(2'-Et-4'-OMe) | 4-(2'-ethylphenyl)-3-pyridylalanine-NH2 |
| 20 | H | Aib | E | G | T | L-α-Me-Phe(2,6-di-Fluoro) | T | S | D | Bip(2'-Et) | 4-(2'-ethylphenyl)-3-pyridylalanine-NH2 |

-continued

| SEQ ID NO. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH2 |
|---|---|---|---|---|---|---|---|---|---|---|---|
| 21 | H | Aib | E | G | T | L-α-Me-Phe(2,6-di-Fluoro) | T | S | D | Bip(2'-Et-4'-OMe) | 4-(4'-pyridyl)-phenylalanine-NH2 |
| 22 | H | Aib | E | G | T | L-α-Me-Phe(2-Fluoro) | T | S | D | Bip(2'-Et-4'-OMe) | 4-[(2'-Methoxy)-3'-pyridyl)phenylalanine-NH2 |
| 23 | H | Aib | E | G | T | L-α-Me-Phe(2-Fluoro) | T | S | D | Bip(2'-Et-4'-OMe) | 4-phenyl-3-pyridylalanine-NH2 |
| 24 | H | Aib | E | G | T | L-α-Me-Phe(2-Fluoro) | T | S | D | Bip(2'-Et-4'-OMe) | 4-(3',5'-dimethylphenyl)-3-pyridylalanine-NH2 |
| 25 | H | Aib | E | G | T | L-α-Me-Phe(2-Fluoro) | T | S | D | Bip(2'-Et-4'-OMe) | 4-[(3'-chloro-4'-fluoro)phenyl]-3-pyridylalanine-NH2 |
| 26 | H | Aib | E | G | T | L-α-Me-Phe(2-Fluoro) | T | S | D | Bip(2'-Et-4'-OMe) | 4-[(3',4'-dimethoxy)phenyl]-3-pyridylalanine-NH2 |
| 27 | H | Aib | E | G | T | L-α-Me-Phe(2-Fluoro) | T | S | D | Bip(2'-Et-4'-OMe) | 4-[(2'-ethyl-4'-methoxy)phenyl)]-3-pyridylalanine-NH2 |
| 28 | L-β-Imidazolelactyl | Aib | E | G | T | L-α-Me-Phe(2-Fluoro) | T | S | D | Bip(2'-Et-4'-OMe) | 4-(2'-Methylphenyl)-3-pyridylalanine-NH2 |
| 29 | H | Aib | E | G | T | L-α-Me-Phe(2-Fluoro) | T | S | D | Bip(2'-Et-4'-OMe) | 4-(3'-Isopropoxyphenyl)-3-pyridylalanine-NH2 |
| 30 | H | Aib | E | G | T | L-α-Me-Phe(2-Fluoro) | T | S | D | Bip(2'-Et-4'-OMe) | 4-(2'-Methyl,5'-Fluoro)phenyl)-3-pyridylalanine-NH2 |
| 31 | H | Aib | E | G | T | L-α-Me-Phe(2-Fluoro) | T | S | D | Bip(2'-Et-4'-OMe) | 4-(2'-Isopropoxyphenyl)-3-pyridylalanine-NH2 |
| 32 | H | Aib | E | G | T | L-α-Me-Phe(2-Fluoro) | T | S | D | Bip(2'-Et-4'-OMe) | 4-(4'-Methoxyphenyl)-3-pyridylalanine-NH2 |
| 33 | H | Aib | E | G | T | L-α-Me-Phe(2-Fluoro) | T | S | D | Bip(2'-Et-4'-OMe) | 4-(2'-Methyl,4'-Fluoro)phenyl)-3-pyridylalanine-NH2 |
| 34 | H | Aib | E | G | T | L-α-Me-Phe(2-Fluoro) | T | S | D | Bip(2'-Et-4'-OMe) | 4-(2'-Methyl,4'-Fluoro)phenyl)-3-pyridylalanine-NH2 |
| 35 | H | Aib | E | G | T | L-α-Me-Phe(2-Fluoro) | T | S | D | Bip(2'-Et) | 4-(2'-Methylphenyl)-3-pyridylalanine-NH2 |
| 36 | H | Aib | E | G | T | L-α-Me-Phe(2-Fluoro) | T | S | D | Bip(2'-Et-4'-OMe) | 4-(2'-Trifluoromethoxyphenyl)- |

| SEQ ID NO. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$-NH2 |
|---|---|---|---|---|---|---|---|---|---|---|---|
| 37 | H | Aib | E | G | T | L-α-Me-Phe(2-Fluoro) | T | S | D | Bip(2'-Et-4'-OMe) | 4-(4'-Trifluoromethoxyphenyl)-3-pyridylalanine-NH2 |
| 38 | H | Aib | E | G | T | L-α-Me-Phe(2-Fluoro) | T | S | D | Bip(2'-Et-4'-OMe) | 4-(2'-Methyl,4'-Chloro)phenyl)-3-pyridylalanine-NH2 |
| 39 | H | Aib | E | G | T | L-α-Me-Phe(2-Fluoro) | T | S | D | Bip(2'-Me-4'-OMe) | 4-(2'-Methylphenyl)-3-pyridylalanine-NH2 |
| 40 | H | Aib | E | G | T | L-α-Me-Phe(2-Fluoro) | T | S | D | Bip(2'-Et-4'-OMe) | 4-(3'-Trifluoromethylphenyl)-3-pyridylalanine-NH2 |
| 41 | H | Aib | E | G | T | L-α-Me-Phe(2-Fluoro) | T | S | D | Bip(2'-Et-4'-OMe) | 4-(4'-Fluorophenyl)-3-pyridylalanine-NH2 |
| 42 | H | Aib | E | G | T | L-α-Me-Phe(2-Fluoro) | T | S | D | Bip(2'-Et-4'-OMe) | 4-(2'-Trifluoromethylphenyl)-3-pyridylalanine-NH2 |
| 43 | H | Aib | E | G | T | L-α-Me-Phe(2-Fluoro) | T | S | D | Bip(2'-Et-4'-OMe) | 4-(2'-Chlorophenyl)-3-pyridylalanine-NH2 |
| 44 | H | Aib | E | G | T | L-α-Me-Phe(2-Fluoro) | T | S | D | Bip(2'-Et-4'-OMe) | 4-(3'-Chlorophenyl)-3-pyridylalanine-NH2 |
| 45 | H | Aib | E | G | T | L-α-Me-Phe(2-Fluoro) | T | S | D | Bip(2'-Et-4'-OMe) | 4-(4'-Isopropylphenyl)-3-pyridylalanine-NH2 |
| 46 | H | Aib | E | G | T | L-α-Me-Phe(2-Fluoro) | T | S | D | Bip(2'-Et-4'-OMe) | 4-[(2'-Methyl-4'-methoxy)phenyl)-3-pyridylalanine-NH2 |
| 47 | H | Aib | E | G | T | L-α-Me-Phe(2-Fluoro) | T | S | D | Bip(2'-Et-4'-OMe) | 4-(4'-Trifluoromethylphenyl)-3-pyridylalanine-NH2 |
| 48 | H | Aib | E | G | T | L-α-Me-Phe(2-Fluoro) | T | S | D | Bip(2'-Et-4'-OMe) | 4-(4'-Pyridyl)-3-pyridylalanine-NH2 |
| 49 | H | Aib | E | G | T | L-α-Me-Phe(2-Fluoro) | T | S | D | Bip(2'-Et-4'-OMe) | 4-(3'-Methoxyphenyl)-3-pyridylalanine-NH2 |
| 50 | H | Aib | E | G | T | L-α-Me-Phe(2-Fluoro) | T | S | D | Bip(2'-Et-4'-OMe) | 4-(6'-Methoxypyridin-3'-yl)-3-pyridylalanine-NH2 |
| 51 | H | Aib | E | G | T | L-α-Me-Phe(2-Fluoro) | T | S | D | Bip(2'-Et-4'-OMe) | 4-(2'-Isopropylphenyl)- |

-continued

| SEQ ID NO. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$-NH2 |
|---|---|---|---|---|---|---|---|---|---|---|---|
| 52 | H | Aib | E | G | T | L-α-Me-Phe(2-Fluoro) | T | S | D | Bip(2'-Et-4'-OMe) | 4-(2'-Methoxyphenyl)-3-pyridylalanine-NH2 |
| 53 | H | Aib | E | G | T | L-α-Me-Phe(2-Fluoro) | T | S | D | Bip(2'-Et-4'-OMe) | 4-[(3',5'-di-Fluoro-2'-methoxy)phenyl]-3-pyridylalanine-NH2 |
| 54 | H | Aib | E | G | T | L-α-Me-Phe(2-Fluoro) | T | S | D | Bip(2'-Et-4'-OMe) | 4-(3'-methylphenyl)-3-pyridylalanine-NH2 |
| 55 | H | Aib | E | G | T | L-α-Me-Phe(2-Fluoro) | T | S | D | Bip(2'-Et-4'-OMe) | 4-(2'-fluorophenyl)-3-pyridylalanine-NH2 |
| 56 | H | Aib | E | G | T | L-α-Me-Phe(2,6-di-Fluoro) | T | S | D | Bip(2'-Et-4'-OMe) | 4-(2'-fluorophenyl)-3-pyridylalanine-NH2 |
| 57 | H | Aib | E | G | T | L-α-Me-Phe(2,6-di-Fluoro) | T | S | D | Bip(2'-Et-4'-OMe) | 4-(3'-Methoxyphenyl)-3-pyridylalanine-NH2 |
| 58 | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 59 | H | N—Me-(D)-Ala | E | G | T | L-α-Me-Phe(2-Fluoro) | T | S | D | Bip(2'-Et-4'-OMe) | 4-(2'-Methylphenyl)-3-pyridylalanine-NH2 |
| 60 | H | (S)-α-Me-Pro | E | G | T | L-α-Me-Phe(2-Fluoro) | T | H | D | Bip(2'-Et-4'-OMe) | 4-(2'-Methylphenyl)-3-pyridylalanine-NH2 |
| 61 | H | (S)-α-Me-Pro | E | G | T | L-α-Me-Phe(2-Fluoro) | T | S | D | Bip(2'-Et-4'-OMe) | (S)-4-(2'-Methylphenyl)-α-Me-3-pyridylalanine-NH2 |
| 62 | H | Aib | E | G | T | L-α-Me-Phe(2-Fluoro) | T | S | D | Bip(2'-Et-4'-OMe) | (S)-4-(2'-Methylphenyl)-α-Me-3-pyridylalanine-NH2 |
| 63 | H | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 64 | H | (S)-α-Me-Pro | E | G | T | L-α-Me-Phe(2,6-di-Fluoro) | T | H | D | Bip(2'-Et-4'-OMe) | 4-(2'-Methylphenyl)-3-pyridylalanine-NH2 |
| 65 | H | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH2 |

-continued

| SEQ ID NO. | X<sub>aa1</sub> | X<sub>aa2</sub> | X<sub>aa3</sub> | X<sub>aa4</sub> | X<sub>aa5</sub> | X<sub>aa6</sub> | X<sub>aa7</sub> | X<sub>aa8</sub> | X<sub>aa9</sub> | X<sub>aa10</sub> | X<sub>aa11</sub>-NH2 |
|---|---|---|---|---|---|---|---|---|---|---|---|
| 66 | H | (S)-α-Me-Pro | E | G | T | L-α-Me-Phe(2,6-di-Fluoro) | T | S | D | Bip(2'-Et-4'-OMe) | 4-(3'-Methoxyphenyl)-3-pyridylalanine-NH2 |
| 67 | H | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH2 |
| 68 | H | (S)-α-Me-Pro | E | G | T | L-α-Me-Phe(2,6-di-Fluoro) | T | S | D | Bip(2'-Et-4'-OMe) | 4-(2'-Fluorophenyl)-3-pyridylalanine-NH2 |
| 69 | H | N—Me-(L)-Ala | E | G | T | L-α-Me-Phe(2-Fluoro) | T | S | D | Bip(2'-Et-4'-OMe) | 4-(2'-Methylphenyl)-3-pyridylalanine-NH2 |
| 70 | H | Aib | E | G | T | L-α-Me-Phe(2-Fluoro) | T | S | D | Bip(2'-Et-4'-OMe) | 4-(2'-Methylphenyl)-3,5-pyrimidylalanine-NH2 |
| 71 | H | (S)-α-Me-Pro | D | G | T | L-α-Me-Phe(2-Fluoro) | T | S | D | Bip(2'-Et-4'-OMe) | 4-(2'-Methylphenyl)-3-pyridylalanine-NH2 |
| 72 | H | (S)-α-Me-Pro | E | G | T | L-α-Me-Phe(2-Fluoro) | T | S | D | Bip(2'-Et) | 4-(2'-Ethylphenyl)-3-pyridylalanine-NH2 |
| 73 | Des-NH2-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 74 | Des-NH2-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 75 | Des-NH2-His | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH2 |
| 76 | Des-NH2-His | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH2 |
| 77 | (R)-Imp | Aib | E | G | T | L-α-Me-Phe(2-Fluoro) | T | S | D | Bip(2'-Et-4'-OMe) | 4-(2'-Methylphenyl)-3-pyridylalanine-NH2 |
| 78 | (R)-Imp | Aib | E | G | T | L-α-Me-Phe(2-Fluoro) | T | H | D | Bip(2'-Et-4'-OMe) | 4-(2'-Methylphenyl)-3-pyridylalanine-NH2 |
| 79 | (S)-Imp | Aib | E | G | T | L-α-Me-Phe(2-Fluoro) | T | S | D | Bip(2'-Et-4'-OMe) | 4-(2'-Methylphenyl)-3-pyridylalanine-NH2 |
| 80 | (S)-Imp | Aib | E | G | T | L-α-Me-Phe(2-Fluoro) | T | H | D | Bip(2'-Et-4'-OMe) | 4-(2'-Methylphenyl)-3-pyridylalanine-NH2 |
| 81 | CH3O—CO-His | (S)-α-Me- | E | G | T | L-α-Me-Phe(2-Fluoro) | T | S | D | Bip(2'-Et-4'-OMe) | 4-(2'-Methylphenyl)-3- |

-continued

| SEQ ID NO. | Xaa1 | Xaa2 | Xaa3 | Xaa4 | Xaa5 | Xaa6 | Xaa7 | Xaa8 | Xaa9 | Xaa10 | Xaa11-NH2 |
|---|---|---|---|---|---|---|---|---|---|---|---|
| 82 | CH3O—CO-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 83 | CH3O—CO-His | N—Me-(D)-Ala | E | G | T | L-α-Me-Phe(2-Fluoro) | T | S | D | Bip(2'-Et-4'-OMe) | 4-(2'-Methylphenyl)-3-pyridylalanine-NH2 |
| 84 | CH3O—CO-His | N—Me-(D)-Ala | E | G | T | L-α-Me-Phe(2,6-di-Fluoro) | T | S | D | Bip(2'-Et-4'-OMe) | 4-(2'-Methylphenyl)-3-pyridylalanine-NH2 |
| 85 | CH3SO2-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 86 | CH3SO2-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 87 | L-Lactyl-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 88 | L-Lactyl-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 89 | H | Aib | E | G | T | L-α-Me-Phe(2-Fluoro) | T | S | D | Bip(2'-Et-4'-OMe) | 4-(3',5'-di-Me)phenyl-3-pyridylalanine-NH2 |
| 90 | H | Aib | E | G | T | L-α-Me-Phe(2-Fluoro) | T | S | D | Bip(2'-Et-4'-OMe) | 4-(2'-Methylphenyl)-3-pyridylalanine-NH2 |
| 91 | H | D-Ala | E | G | T | L-α-Me-Phe(2-Fluoro) | T | S | D | Bip(2'-Et-4'-OMe) | 4-(2'-Methylphenyl)-3-pyridylalanine-NH2 |
| 92 | H | Aib | E | G | T | L-α-Me-Phe(2-Fluoro) | T | S | D | Bip(2'-Et-4'-OMe) | 4-(2'-Methylphenyl)-3-pyridylalanine-NH2 |

In preferred embodiments of the subject matter described and claimed herein, a polypeptide is selected from the group consisting of SEQ ID NO's: 1, 2, 4, 9, 10, 19, 20, 23, 38, 43, 46, 49, 57, 58, 59, 61, 62, 63, 65, 69, 70, 72, 73, 74, 75, 76, 77, 78, 79, 80, 81, 82, 83, 84, and 90.
In another aspect, the isolated polypeptide is:
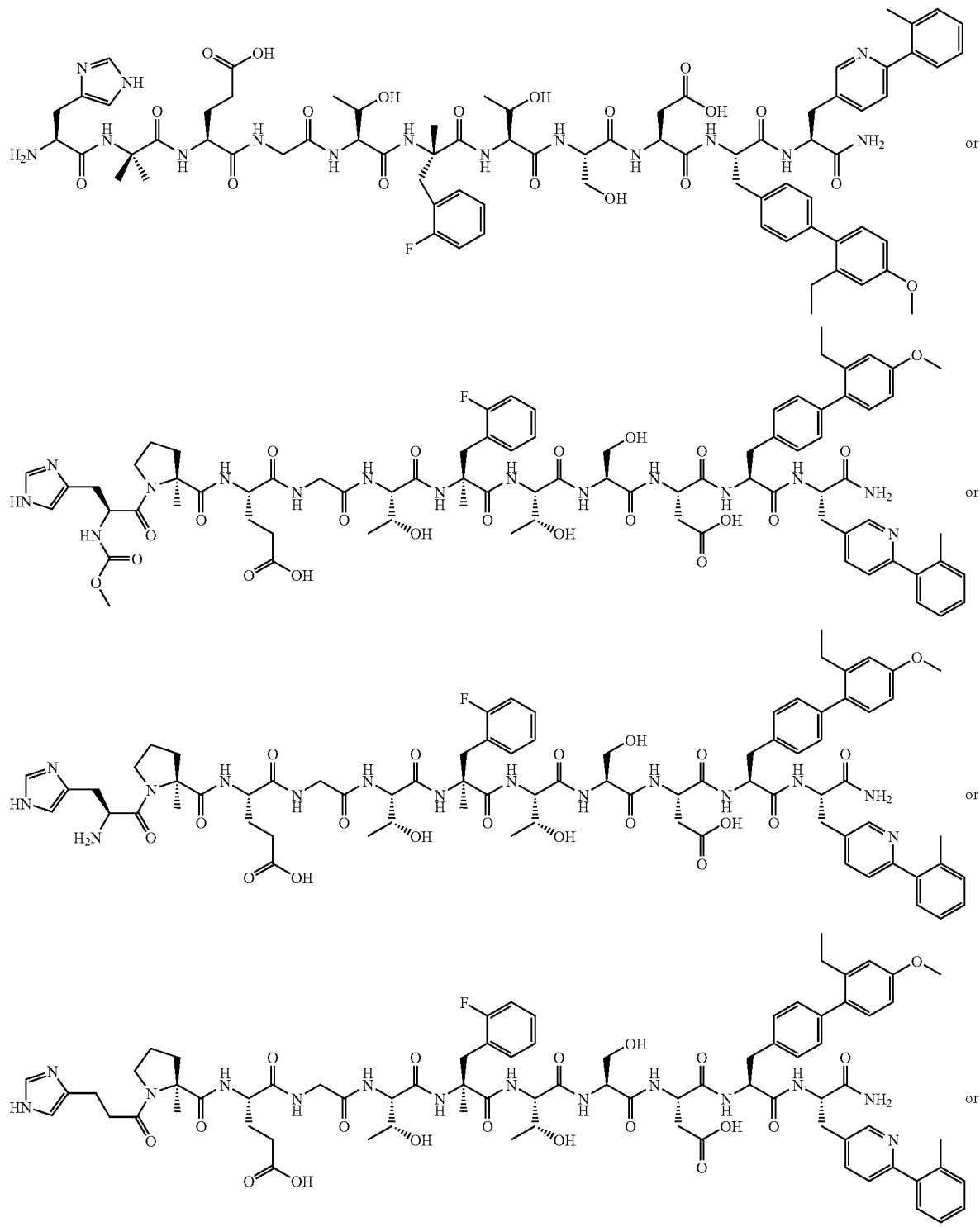

-continued
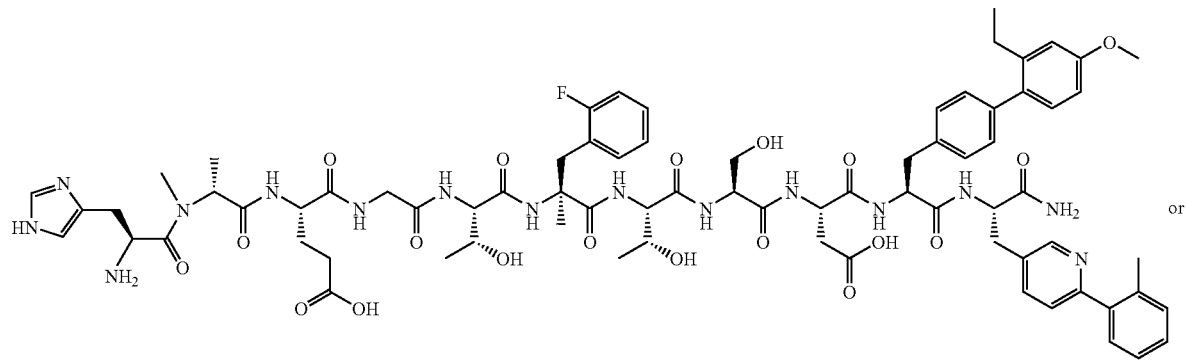 or
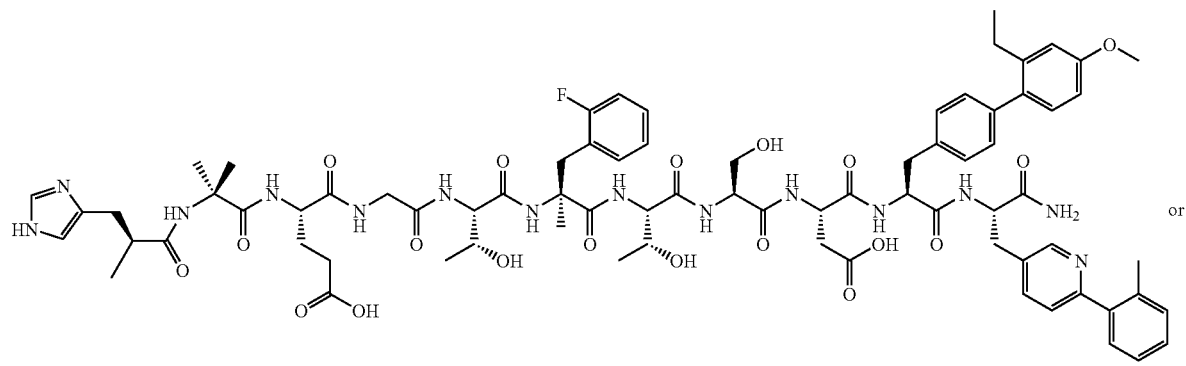 or
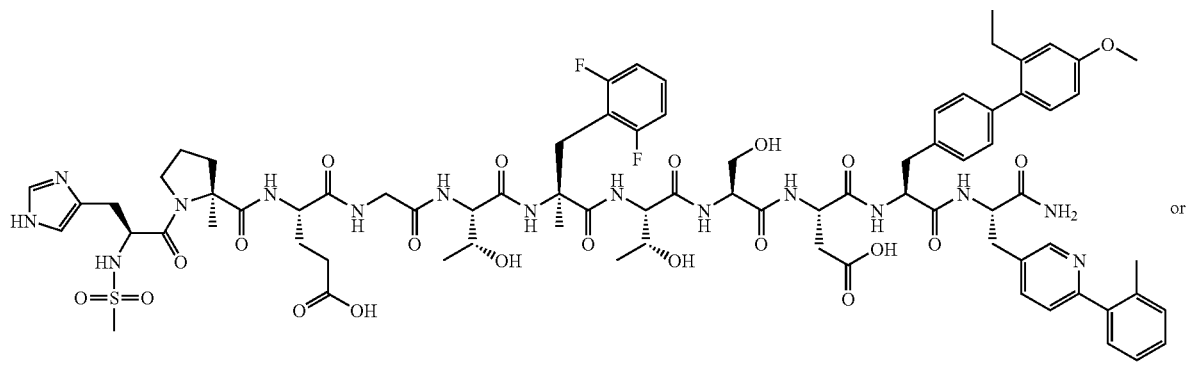 or
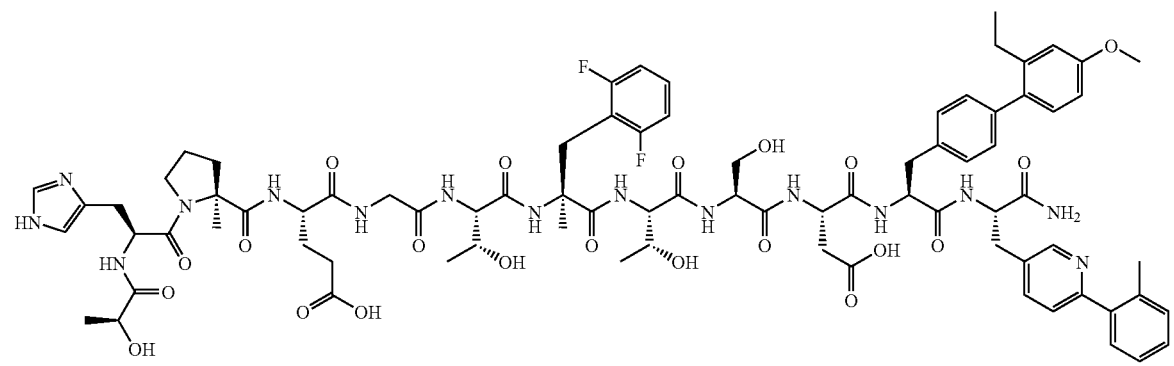

In another aspect, the isolated polypeptide is:
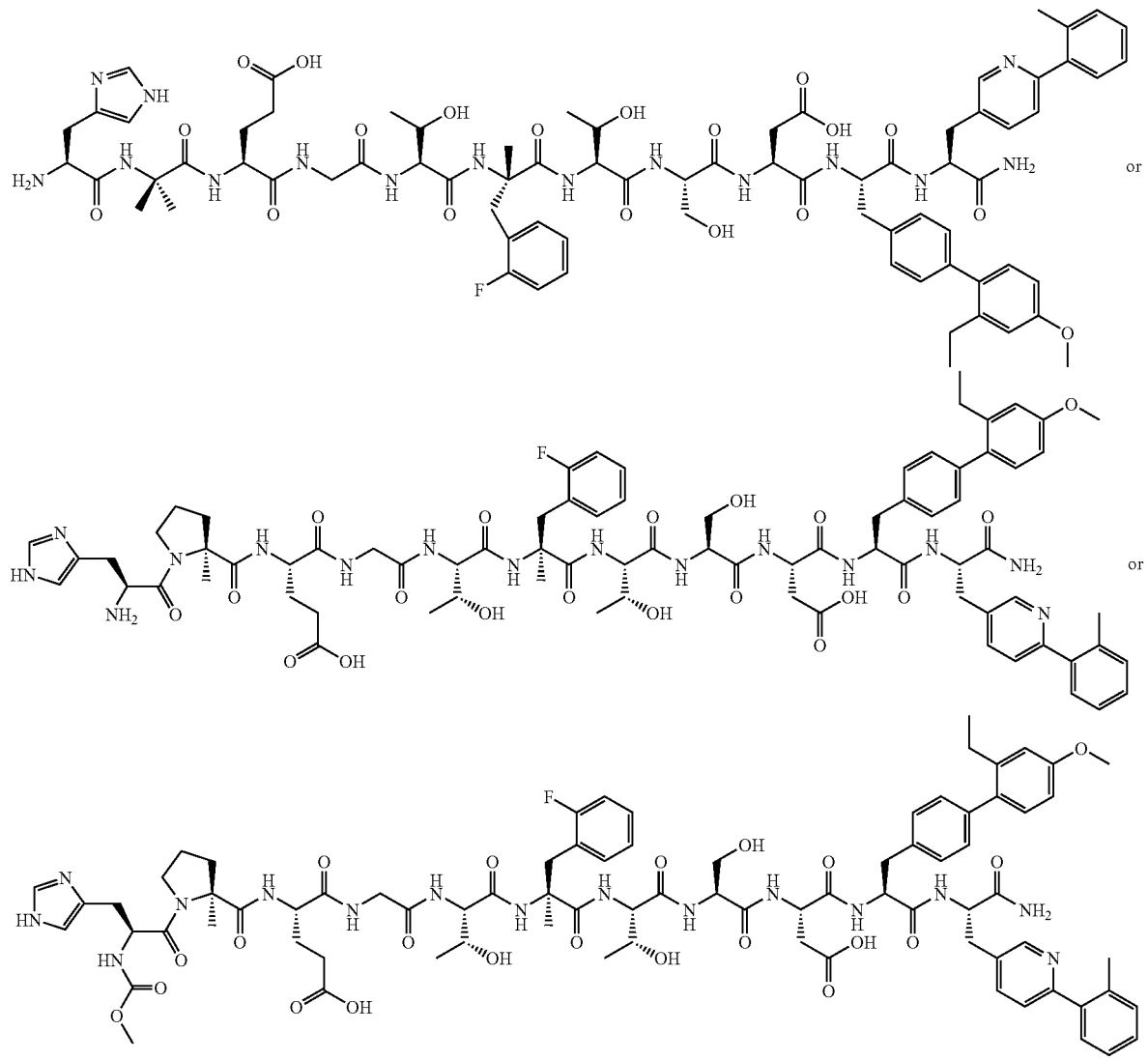
In another aspect, the isolated polypeptide is:
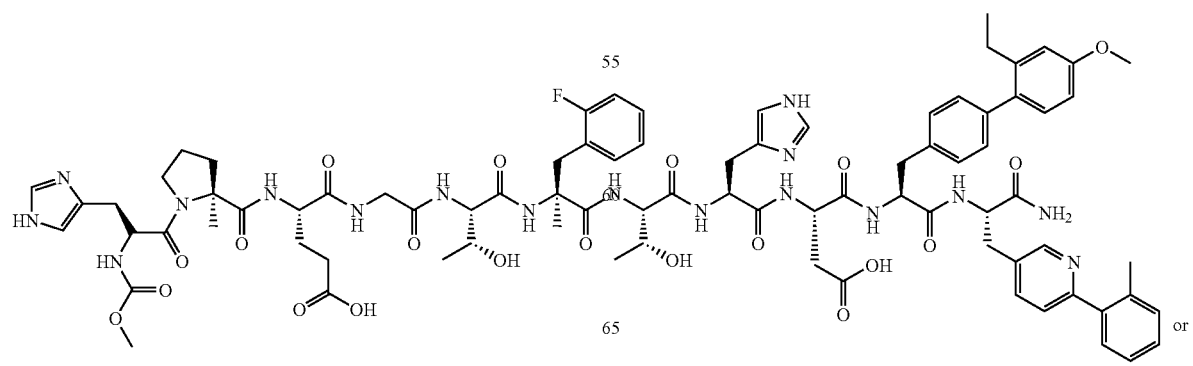

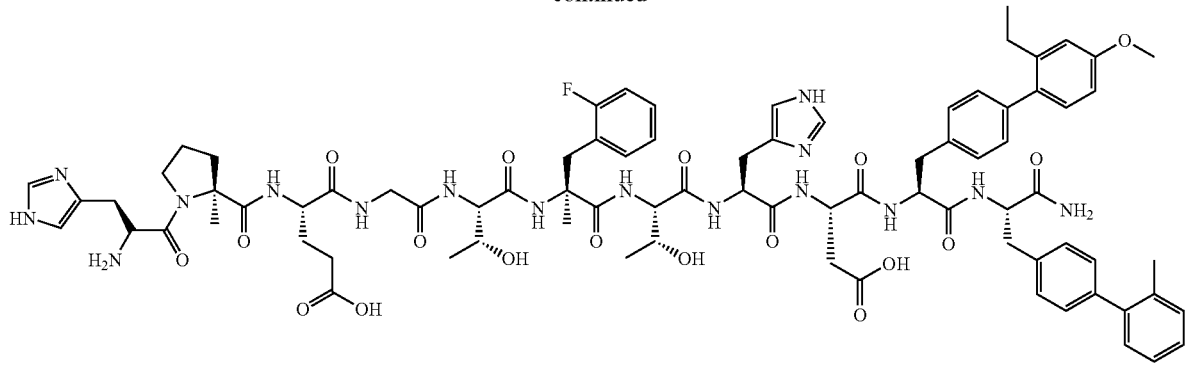

In another aspect, the present invention is directed to a compound of Formula VIa:

Formula VIa

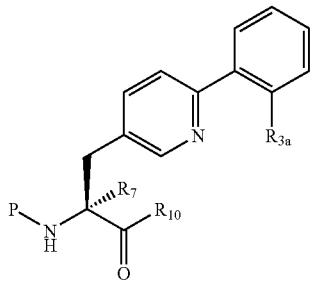

wherein P is hydrogen, fluorenylmethyloxycarbonyl (Fmoc) or t-butyloxycarbonyl (t-Boc); wherein $R_{3a}$ is selected from the group consisting of methyl, ethyl and fluoro; wherein $R_{10}$ is selected from the group consisting of OH and $NH_2$; and wherein $R_7$ is selected from the group consisting of hydrogen and methyl.

In another aspect, the present invention is directed to a compound of Formula VIIa:

Formula VIIa

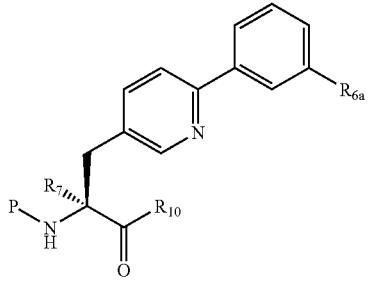

wherein P is hydrogen, fluorenylmethoxycarbonyl (Fmoc) or t-butyloxycarbonyl (t-Boc); wherein $R_{6a}$ is methoxy; wherein $R_{10}$ is selected from the group consisting of OH and $NH_2$; and wherein $R_7$ is selected from the group consisting of hydrogen and methyl.

In another aspect, the present invention is directed to a pharmaceutical composition, comprising an isolated polypeptide as described herein and a pharmaceutically acceptable carrier thereof.

In another aspect, the present invention is directed to a pharmaceutical composition comprising an isolated polypeptide as described herein and at least one therapeutic agent; wherein the therapeutic agent is selected from the group consisting of an antidiabetic agent, an anti-obesity agent, an anti-hypertensive agent, an anti-atherosclerotic agent and a lipid-lowering agent.

The antidiabetic agent may be selected from the group consisting of a biguanide, a sulfonyl urea, a glucosidase inhibitor, a PPAR γ agonist, a PPAR α/γ dual agonist, an aP2 inhibitor, a DPP4 inhibitor, an insulin sensitizer, a glucagon-like peptide-1 (GLP-1) analog, insulin and a meglitinide.

The antidiabetic agent may be selected from the group consisting of metformin, glyburide, glimepiride, glipyride, glipizide, chlorpropamide, gliclazide, acarbose, miglitol, pioglitazone, troglitazone, rosiglitazone, muraglitazar, insulin, G1-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, NVP-DPP-728A and saxagliptin.

The anti-obesity agent may be selected from the group consisting of a beta 3 adrenergic agonist, a lipase inhibitor, a serotonin (and dopamine) reuptake inhibitor, a thyroid receptor beta compound, a CB-1 antagonist, a NPY-Y2 or NPY-Y4 receptor agonist and an anorectic agent.

The anti-obesity agent may be selected from the group consisting of orlistat, ATL-962, AJ9677, L750355, CP331648, sibutramine, topiramate, axokine, dexamphetamine, phentermine, phenylpropanolamine rimonabant (SR141716A), PYY (3-36), Pancreatic Polypeptide (PP) and mazindol.

The lipid lowering agent may be selected from the group consisting of an MTP inhibitor, cholesterol ester transfer protein, an HMG CoA reductase inhibitor, a squalene synthetase inhibitor, a fibric acid derivative, an upregulator of LDL receptor activity, a lipoxygenase inhibitor, and an ACAT inhibitor.

The lipid lowering agent may be selected from the group consisting of pravastatin, lovastatin, simvastatin, atorvastatin, cerivastatin, fluvastatin, nisvastatin, visastatin, fenofibrate, gemfibrozil, clofibrate, avasimibe, TS-962, MD-700, CP-529414, and LY295427.

In another aspect, the present invention is directed to a method for treating or delaying the progression or onset of diabetes, diabetic retinopathy, diabetic neuropathy, diabetic nephropathy, wound healing, insulin resistance, hyperglycemia, hyperinsulinemia, Syndrome X, diabetic complications, elevated blood levels of free fatty acids or glycerol, hyperlipidemia, obesity, hypertriglyceridemia, atherosclerosis or hypertension, which comprises administering to a mammalian species in need of treatment a therapeutically effective amount of an isolated polypeptide described herein.

The method may further comprise the concurrent or sequential administration of a therapeutically effective amount of one or more therapeutic agents selected from the group consisting of an antidiabetic agent, an anti-obesity agent, a anti-hypertensive agent, and an anti-atherosclerotic agent and a lipid-lowering agent.

In another aspect, the present invention is directed to a method for treating or delaying the progression or onset of diabetes, diabetic retinopathy, diabetic neuropathy, diabetic nephropathy, wound healing, insulin resistance, hyperglycemia, hyperinsulinemia, Syndrome X, diabetic complications, elevated blood levels of free fatty acids or glycerol, hyperlipidemia, obesity, hypertriglyceridemia, atherosclerosis or hypertension, which comprises administering to a mammalian species in need of treatment a therapeutically effective amount of a pharmaceutical composition described herein.

In another aspect, the present invention is directed to a method for administering a polypeptide described herein, comprising the parenteral administration of a formulation comprising a polypeptide described herein.

In another aspect, the present invention is directed to a method for administering a polypeptide described herein, comprising the non-parenteral administration of a formulation comprising a polypeptide described herein.

The parenteral administration may be selected from the group consisting of intravenous (IV) bolus injection, IV infusion, subcutaneous administration, intramuscular administration, intranasal administration, buccal administration, pulmonary administration and ophthalmic delivery.

The subcutaneous administration may involve the use of an immediate or sustained release formulation.

The intramuscular administration may involve the use of an immediate or sustained release formulation.

The formulation may further comprise a pharmaceutically acceptable excipient selected from the group consisting of a solvent and co-solvent, a solubilizing agent, an emulsifying agent, a thickening agent, a chelating agent, an anti-oxidant, a reducing agent, an antimicrobial preservative, a buffer and pH adjusting agent, a bulking agent, a protectant and tonicity adjustor, and a special additive.

The formulation may further comprise an encapsulated delivery system.

DETAILED DESCRIPTION OF THE INVENTION

Figure 1:
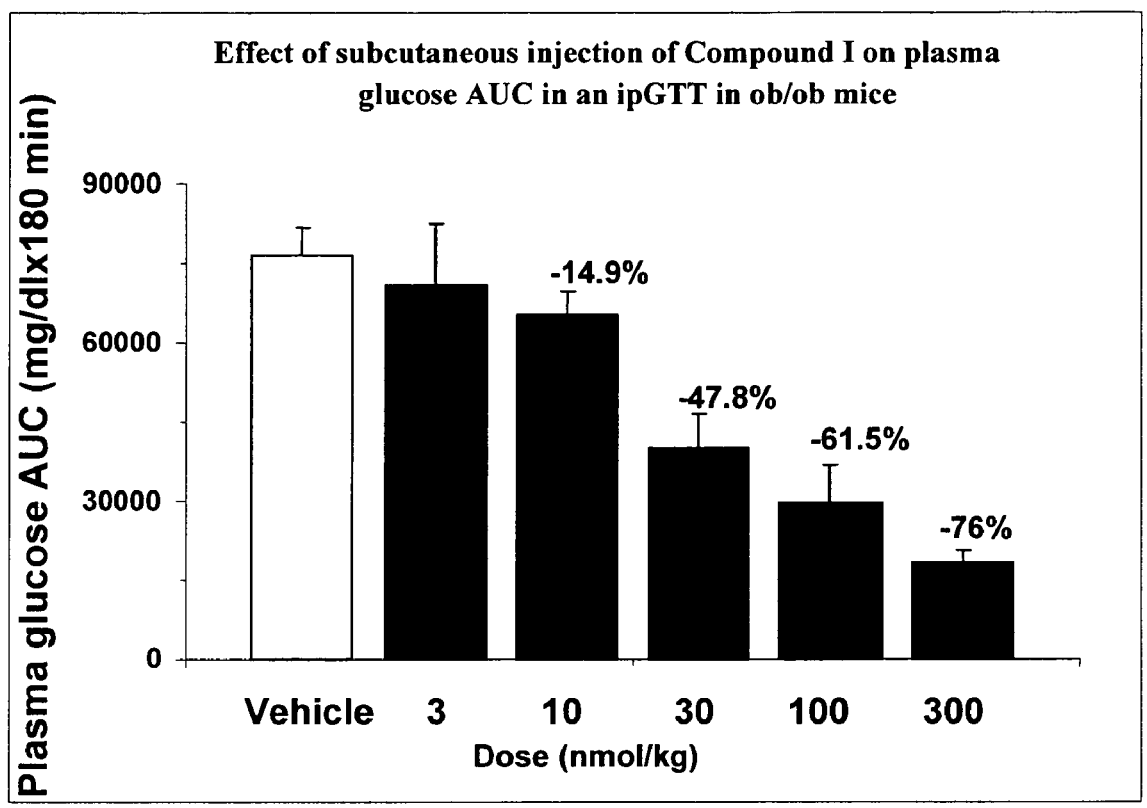
FIG. 1 illustrates the effects of subcutaneous injection of Compound I on plasma glucose in an intraperitoneal glucose tolerance test (ipGTT) in obese ob/ob mice.

The present invention provides novel human glucagon-like peptide-1 (GLP-1) peptide receptor modulators, agonists or partial agonists, which exhibit superior biological properties of the native peptide, GLP-1, and exhibit increased stability to proteolytic cleavage as compared to GLP-1 native sequences, and thus are useful for the amelioration of the diabetic condition.

The synthetic isolated peptides of the present invention and described herein are capable of modulating the GLP-1 receptor, desirably as agonists or partial agonists of the GLP-1 receptor. These synthetic peptide exhibit superior in-vivo efficacy and pharmacokinetic properties relative to GLP-1, including postprandial plasma glucose lowering and concomitant increase in plasma insulin levels, thus making them ideal therapeutic candidates for subcutaneous, pulmonary, nasal, buccal or sustained release administration.

The present invention includes, for example, an isolated polypeptide comprising a polypeptide having a sequence of Formula I:

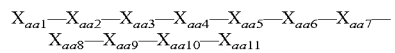

$$X_{aa1}-X_{aa2}-X_{aa3}-X_{aa4}-X_{aa5}-X_{aa6}-X_{aa7}-X_{aa8}-X_{aa9}-X_{aa10}-X_{aa11} \qquad I$$

wherein, $X_{aa1}$ is a naturally or nonnaturally occurring amino acid comprising an imidazole; wherein one or more carbon atoms of the amino acid are optionally substituted with one or more alkyl groups; wherein the amino acid optionally has a free amino group which is optionally substituted with alkyl, acyl, benzoyl, L-lactyl, alkyloxycarbonyl, aryloxycarbonyl, arylalkyloxycarbonyl, heterocyclyloxycarbonyl, heteroarylalkyloxycarbonyl, alkylcarbamoyl, arylcarbamoyl, arylalkylcarbamoyl, heterocyclylsulfonyl, alkylsulfonyl, arylsulfonyl, arylalkylsulfonyl, heteroarylalkylsulfonyl or heteroarylsulfonyl; and wherein when the free amino group is not present $X_{aa1}$ is the des-amino acid of histidine in which one or more carbon atoms of the amino acid are optionally substituted with one or more alkyl groups;

$X_{aa2}$ is a naturally or nonnaturally occurring amino acid selected from the group consisting of D-alanine, α-aminoisobutyric acid (Aib), N-methyl-D-alanine, N-ethyl-D-alanine, 2-methyl-azetidine-2-carboxylic acid, alpha-methyl-(L)-proline, 2-methylpiperidine-2-carboxylic acid and isovaline;

$X_{aa3}$ is a naturally or nonnaturally occurring amino acid having (1) an amino acid side chain comprising a carboxylic acid or (2) an imidazole side chain, and wherein one or more carbon atoms of the amino acid is optionally substituted with one or more alkyl groups;

$X_{aa4}$ is glycine;

$X_{aa5}$ is a naturally or nonnaturally occurring amino acid selected from the group consisting of (L)-threonine and (L)-norvaline; and wherein one or more carbon atoms of the amino acid is optionally substituted with one or more alkyl groups;

$X_{aa6}$ is a naturally or nonnaturally occurring amino acid having a disubstituted alpha carbon having two side chains; wherein at least one of the two side chains has an aromatic ring and at least one of the two chains has an alkyl group; and wherein one or more carbon atoms of the amino acid is optionally substituted with one or more alkyl groups or one or more halo groups.

$X_{aa7}$ is a naturally or nonnaturally occurring amino acid having an amino acid side chain which is substituted with a hydroxyl group; and wherein one or more carbon atoms of the amino acid is optionally substituted with one or more alkyl groups;

$X_{aa8}$ is a naturally or nonnaturally occurring amino acid selected from the group consisting of L-serine and L-histidine; and wherein one or more carbon atoms of the amino acid is optionally substituted with one or more alkyl groups;

$X_{aa9}$ is a naturally or nonnaturally occurring amino acid having an amino acid side chain comprising a carboxylic acid; and wherein one or more carbon atoms of the amino acid is optionally substituted with one or more alkyl groups;

$X_{aa10}$ is a naturally or nonnaturally occurring amino acid of Formula II:

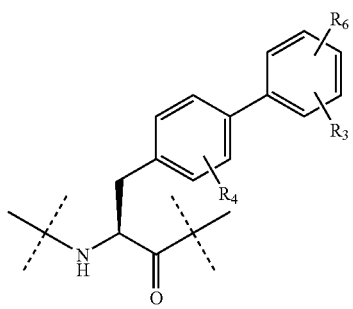

Formula II wherein $R_4$ is selected from the group consisting of hydrogen, alkyl, and halo;

wherein $R_3$ and $R_6$ are each independently selected from the group consisting of hydrogen, halo, methyl, ethyl, alkyl, hydroxyl, methoxy, and alkoxy;

wherein the phenyl ring proximal to the beta-carbon of the amino acid is additionally optionally substituted with hydrogen, alkyl or halo; and wherein the phenyl ring distal to the beta-carbon of the amino acid is additionally optionally substituted with hydrogen, halo, methyl, ethyl, alkyl, hydroxyl, methoxy, and alkoxy;

$X_{aa11}$ is a naturally or nonnaturally occurring amino acid of Formula IVa:

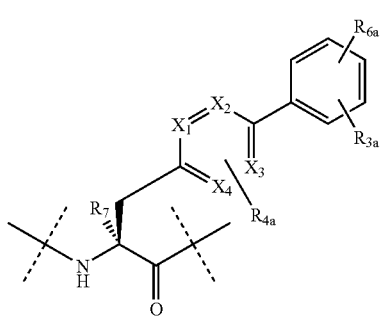

Formula IVa wherein the C-terminal carbonyl carbon of the amino acid is attached to a nitrogen to form a carboxamide ($NH_2$);

wherein $R_{4a}$ is selected from the group consisting of hydrogen, alkyl, and halo;

wherein $R_{3a}$ and $R_{6a}$ are each independently selected from the group consisting of hydrogen, halo, methyl, ethyl, alkyl, hydroxyl, methoxy, and alkoxy;

wherein $R_7$ is selected from the group consisting of hydrogen, methyl, and ethyl; and wherein $X_1$, $X_2$, $X_3$ and $X_4$ are each C or N, with the proviso that at least one of $X_1$, $X_2$, $X_3$ and $X_4$ is N;

wherein the phenyl ring proximal to the beta-carbon of the amino acid is additionally optionally substituted with hydrogen, alkyl or halo; and wherein the phenyl ring distal to the beta-carbon of the amino acid is additionally optionally substituted with hydrogen, halo, methyl, ethyl, alkyl, hydroxyl, methoxy, and alkoxy.

The definitions provided herein apply, without limitation, to the terms as used throughout this specification, unless otherwise limited in specific instances.

Those skilled in the art of amino acid and peptide chemistry are aware that an amino acid includes a compound represented by the general structure:

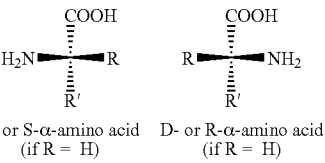

L- or S-α-amino acid (if R = H)   D- or R-α-amino acid (if R = H)

Where R and R' are as discussed herein. Unless otherwise indicated, the term "amino acid" as employed herein alone or as part of another group includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R substituents" equal hydrogen, the amino acid is glycine and is not chiral.

Unless otherwise indicated, the term "amino-alcohol" as employed herein alone or as part of another group includes, without limitation, a natural or un-natural amino acid in which the carboxy group is replaced (reduced) to a methyl alcohol such as valinol, glycinol, alaninol, arylalaninol, heteroarylalaninol.

Unless otherwise indicated, the term "alkyl" as employed herein alone or as part of another group includes, without limitation, both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxy, arylalkyl, cycloalkyl, cycloalkylalkyl, alkoxy, arylalkyloxy, heteroaryloxy, heteroarylalkyloxy, alkanoyl, halo, hydroxyl, thio, nitro, cyano, carboxyl, carbonyl

carboxamido, amino, alkylamino, dialkylamino, amido, alkylamino, arylamido, hetarylamido, azido, guanidino, amidino, phosphonic, phosphinic, sulfonic, sulfonamido, haloaryl, $CF_3$, $OCF_2$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "alkenyl" as employed herein alone or as part of another group includes, without limitation, both straight and branched chain hydrocarbons, containing 2 to 40 carbons with one or more double bonds, preferably 2 to 20 carbons with one to three double bonds, more preferably 2 to 8 carbons with one to two double bonds, in the normal chain, such that any carbon may be optionally substituted as described above for "alkyl".

Unless otherwise indicated, the term "alkynyl" as employed herein alone or as part of another group includes, without limitation, both straight and branched chain hydrocarbons, containing 2 to 40 carbons with one or more triple bonds, preferably 2 to 20 carbons with one to three triple bonds, more preferably 2 to 8 carbons with one to two triple bonds, in the normal chain, such that any carbon may be optionally substituted as described above for "alkyl".

Unless otherwise indicated, the term "cycloalkyl" as employed herein alone or as part of another group includes, without limitation, saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

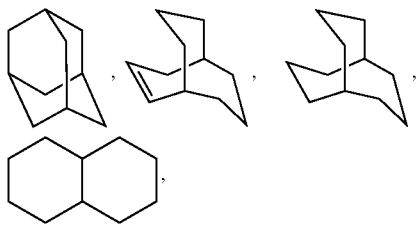

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl ($\overset{\text{O}}{\|}$) carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "aryl" as employed herein alone or as part of another group refers, without limitation, to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or heterocycloalkyl rings) and may be optionally substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, hetroarylalkyloxy, hetroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalyklaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers, without limitation, to alkyl groups as defined above having an aryl substituent, such as benzyl, phenethyl or naphthylpropyl, wherein said aryl and/or alkyl groups may optionally be substituted as defined above.

The term "alkoxy", "aryloxy", "heteroaryloxy" "arylalkyloxy", or "heteroarylalkyloxy" as employed herein alone or as part of another group includes, without limitation, an alkyl or aryl group as defined above linked through an oxygen atom.

The term "heterocyclo", "heterocycle" "heterocyclyl" or "heterocyclic", as used herein, represents, without limitation, an unsubstituted or substituted stable 4-, 5-, 6- or 7-membered monocyclic ring system which may be saturated or unsaturated, and which consists of carbon atoms and from one to four heteroatoms selected from nitrogen, sulfur, oxygen and/or a SO or $SO_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, tetrahydrofuranyl, tetrahydrothiophenyl pyrrolidinyl, piperidinyl, piperazinyl, oxopyrrolidinyl, oxopiperazinyl, oxopiperidinyl and oxadiazolyl. Optionally a heterocyclo group may be substituted with one or more functional groups, such as those described for "alkyl" or "aryl".

The term "heterocycloalkyl" as used herein alone or as part of another group refers, without limitation, to alkyl groups as defined above having a heterocycloalkyl substituent, wherein said "heterocyclo" and/or alkyl groups may optionally be substituted as defined above.

The term "heteroaryl" as used herein refers, without limitation, to a 5-, 6- or 7-membered aromatic heterocyclic ring which contains one or more heteroatoms selected from nitrogen, sulfur, oxygen and/or a SO or $SO_2$ group. Such rings may be fused to another aryl or heteroaryl ring and include possible N-oxides; Examples of such heteroaryl groups include, but are not limited to, furan, pyrrole, thiophene, pyridine, pyrimidine, pyrazine, pyridazine, isoxazole, oxazole, imidazole and the like. Optionally a heteroaryl group may be substituted with one or more functional groups commonly attached to such chains, such as those described for "alkyl" or "aryl".

The term "heteroarylalkyl" as used herein alone or as part of another group refers, without limitation, to alkyl groups as defined above having a heteroaryl substituent, wherein said heteroaryl and/or alkyl groups may optionally be substituted as defined above.

The term "alkyloxycarbonyl" as used herein alone or as part of another group refers, without limitation, to alkyl groups as defined above attached to the oxygen of an —OC(O)— group, for example $CH_3OC(O)$—, $CH_3CH_2OC(O)$— or $CH_2(OH)CH_2OC(O)$—.

The term "aryloxycarbonyl" as used herein alone or as part of another group refers, without limitation, to aryl groups as defined above attached to the oxygen of an —OC(O)— group.

The term "arylalkyloxycarbonyl" as used herein alone or as part of another group refers, without limitation, to aralkyl groups as defined above attached to the oxygen of an —OC(O)— group.

The term "heterocyclyloxycarbonyl" as used herein alone or as part of another group refers, without limitation, to heterocyclyl groups as defined above attached by any carbon atom of the heterocyclyl group to the oxygen of an —OC(O)— group.

The term "heterocyclyloxycarbonyl" as used herein alone or as part of another group refers, without limitation, to heterocyclyl groups as defined above attached by any carbon atom of the heterocyclyl group to the oxygen of an —OC(O)— group.

The term "heteroarylalkyloxycarbonyl" as used herein alone or as part of another group refers, without limitation, to heteroarylalkyl groups as defined above attached by any carbon atom of the heterocyclyl group to the oxygen of an —OC(O)— group.

The term "alkylcarbamoyl" as used herein alone or as part of another group refers, without limitation, to alkyl groups as defined above attached to the nitrogen of a —NC(O)— group, for example $CH_3NHC(O)$—, $CH_3CH_2NHC(O)$— or $(CH_3)_2NHC(O)$— and wherein when 2 alkyl groups are present, the alkyl groups can optionally be attached to form a 4, 5, 6 or 7 membered ring, for example,

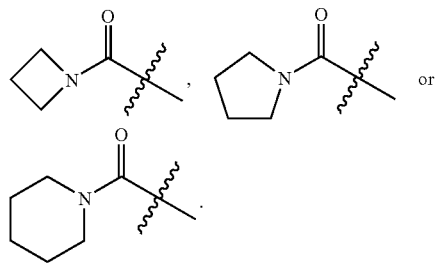

The term "arylalkylcarbamoyl" as used herein alone or as part of another group refers, without limitation, to arylalkyl groups as defined above attached to the nitrogen of a —NC(O)— group.

The term "heterocyclylcarbamoyl" as used herein alone or as part of another group refers, without limitation, to heterocylclyl groups as defined above attached to the nitrogen of an —NC(O)— group.

The term "alkylsulfonyl" as used herein alone or as part of another group refers, without limitation, to alkyl groups as defined above attached to the sulfur of an —S(O)$_2$— group for example $CH_3S(O)_2$—, $CH_3CH_2S(O)_2$— or $(CH_3)_2CH_2S(O)_2$—.

The term "arylsulfonyl" as used herein alone or as part of another group refers, without limitation, to aryl groups as defined above attached to the sulfur of an —S(O)$_2$— group.

The term "arylalkylsulfonyl" as used herein alone or as part of another group refers, without limitation, to arylalkyl groups as defined above attached to the sulfur of an —S(O)$_2$— group.

The term "heteroarylsulfonyl" as used herein alone or as part of another group refers, without limitation, to heteroaryl groups as defined above attached to the sulfur of an —S(O)$_2$— group.

The term "heteroarylalkylsulfonyl" as used herein alone or as part of another group refers, without limitation, to heteroarylalkyl groups as defined above attached to the sulfur of an —S(O)$_2$— group.

The term "receptor modulator" refers to a compound that acts at the GLP-1 receptor to alter its ability to regulate downstream signaling events. Examples of receptor modulators include agonists, antagonists, partial agonists, inverse agonists, allosteric antagonists and allosteric potentiators as defined in standard pharmacology textbooks (e.g. E. M. Ross and T. P. Kenakin in Goodman and Gilman's The Pharmacological Basis of Therapeutics, 10th edition (2001) McGraw Hill, Chapter 2, pp. 31-43).

One of skill in the art will readily appreciate the meaning of such terms as provided in the present case and in the art.

The term "diabetes and related diseases or related conditions" refers, without limitation, to Type II diabetes, Type I diabetes, impaired glucose tolerance, obesity, hyperglycemia, Syndrome X, dysmetabolic syndrome, diabetic complications, and hyperinsulinemia.

The term "lipid-modulating" or "lipid lowering" agent as employed herein refers, without limitation, to agents that lower LDL and/or raise HDL and/or lower triglycerides and/or lower total cholesterol and/or other known mechanisms for therapeutically treating lipid disorders.

An administration of a therapeutic agent of the invention includes, without limitation, administration of a therapeutically effective amount of the agent of the invention. The term "therapeutically effective amount" as used herein refers, without limitation, to an amount of a therapeutic agent to treat or prevent a condition treatable by administration of a composition of the invention. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Peptides of the present invention were evaluated in a glucose tolerance test in ob/ob mice to assess their relative in vivo efficacy as described in Example 22 below. Peptides of the present invention show superior potency in this efficacy model of glucose lowering and superior pharmacokinetics (as measured by subcutaneous injection in dogs, described in Example 25), relative to peptides exemplified by Compound I from WO 2003/033671, incorporated herein by reference in its entirety, as illustrated in Tables 1 and 2:

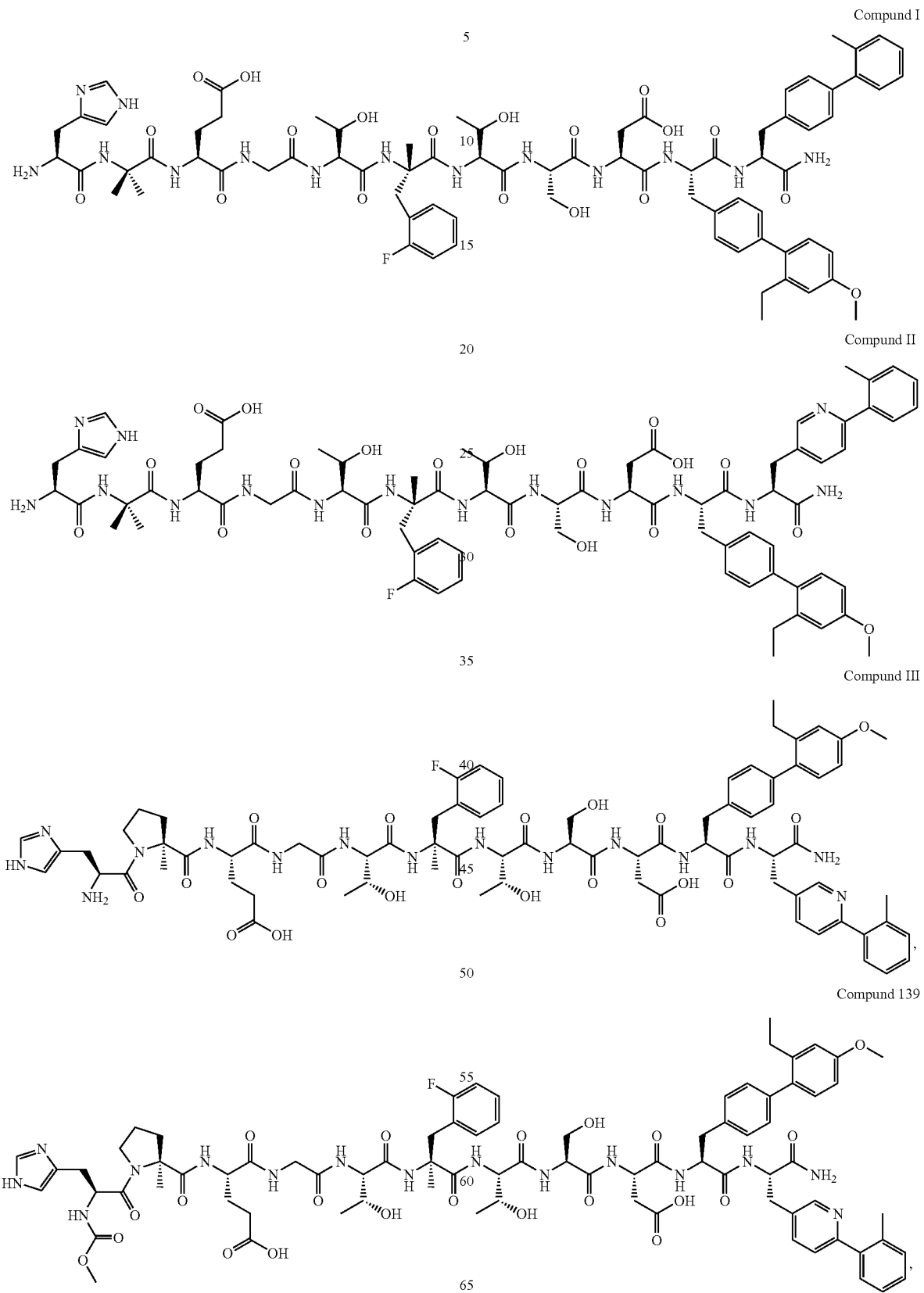

TABLE 1

| Test Agent | Potency in ob/ob mice | Exposure in dogs (sc@67 µg/kg) |
|---|---|---|
| Compound I | ED50 = 50 nmoles/kg | 89 nM * h |
| SEQ ID NO:1 | ED50 = 5 nmoles/kg | 1230 nM * h |
| SEQ ID NO:58 | ED50 = 2.5 nmoles/kg | 4020 nM * h |

TABLE 2

| Test Agent | Activity in ob/ob mice: % AUC Reduction in Plasma Glucose in an IP Glucose Tolerance Test after SC Injection of Compound* | Exposure in dogs (sc@67 µg/kg) |
|---|---|---|
| Compound I | −15% (p = 0.247, NS**) (10 nmol/kg) −48% (p < 0.01) (30 nmol/kg) | 89 nM * h |
| SEQ ID NO:1 | −68% (p < 0.0001) (10 nmol/kg) | 1230 nM * h |
| SEQ ID NO:58 | −70% (p < 0.001) (10 nmol/kg) | 4020 nM * h |
| SEQ ID NO:91 | −54% (p < 0.0001) (10 nmol/kg) | 940 nM * h |
| SEQ ID NO:82 | −73% (p < 0.001) (10 nmol/kg) | 283 nM * h |
| SEQ ID NO:60 | −68% (p < 0.0001) (10 nmol/kg) | 1116 nM * h |
| SEQ ID NO:61 | −50% (p < 0.05) (10 nmol/kg) | 1129 nM * h |
| SEQ ID NO:70 | −72% (p < 0.0001) (10 nmol/kg) | 541 nM * h |
| SEQ ID NO:81 | −63% (p < 0.01) (10 nmol/kg) | 1603 nM * h |
| SEQ ID NO:59 | −61% (p < 0.0001) (5 nmol/kg) | 1257 nM * h |
| SEQ ID NO:92 | −38% (p < 0.05) (10 nmol/kg) | 979 nM * h |

*AUC = area under the curve. AUC values are calculated using the fasting plasma glucose value as the baseline in each individual animal. The percentage change in the AUC is calculated relative to the AUC for the vehicle-treated group in the samestudy. The p values given are determined by comparison to the vehicle-treated group using analysis of variance (ANOVA) followed by Fisher's post-hoc test,
**NS = non-statistically significant.

The peptides and analogs thereof described herein may be produced by chemical synthesis using various solid-phase techniques such as those described in G. Barany and R. B. Merrifield, "The Peptides: Analysis, Synthesis, Biology"; Volume 2—"Special Methods in Peptide Synthesis, Part A", pp. 3-284, E. Gross and J. Meienhofer, Eds., Academic Press, New York, 1980; and in J. M. Stewart and J. D. Young, "Solid-Phase Peptide Synthesis", $2^{nd}$ Ed., Pierce Chemical Co., Rockford, Ill., 1984.

A desired strategy for use in this invention is based on the Fmoc (9-Fluorenylmethylmethyloxycarbonyl) group for temporary protection of the α-amino group, in combination with the tert-butyl group for temporary protection of the amino acid side chains (see for example E. Atherton and R. C. Sheppard, "The Fluorenylmethoxycarbonyl Amino Protecting Group", in "The Peptides: Analysis, Synthesis, Biology"; Volume 9—"Special Methods in Peptide Synthesis, Part C", pp. 1-38, S. Undenfriend and J. Meienhofer, Eds., Academic Press, San Diego, 1987.

Peptides of the present invention can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) as described herein and, after completion of the peptide sequence assembly, the resulting peptide alcohol is released with $LiBH_4$ in THF (see J. M. Stewart and J. D. Young, supra, p. 92).

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports for use in this invention are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBT or HOAT active esters produced from DIC/HOBT, HBTU/HOBT, BOP, PyBOP, or from DIC/HOAT, HATU/HOAT, respectively. Preferred solid supports for use in this invention are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the 11-mer peptide analogs described herein can be carried out by using a peptide synthesizer, such as an Advanced Chemtech Multiple Peptide Synthesizer (MPS396) or an Applied Biosystems Inc. peptide synthesizer (ABI 433A). If the MPS396 was used, up to 96 peptides were simultaneously synthesized. If the ABI 433A synthesizer was used, individual peptides were synthesized sequentially. In both cases the stepwise solid phase peptide synthesis was carried out utilizing the Fmoc/t-butyl protection strategy described herein.

The non-natural non-commercial amino acids present at position-$X_{aa11}$ and at position-$X_{aa10}$ were incorporated into the peptide chain in one of two methods. In the first approach, a Boc- or Fmoc-protected non-natural amino acid was prepared in solution using appropriate organic synthetic procedures. The resulting derivative was then used in the step-wise synthesis of the peptide. Alternatively the required non-natural amino acid was built on the resin directly using synthetic organic chemistry procedures. When a non-natural non-commercial amino acid was needed for incorporation at position $X_{aa6}$ or at any other $X_{aa}$ position, the required Fmoc-protected non-natural amino acid was synthesized in solution. Such a derivative was then used in stepwise solid phase peptide synthesis.

Desired for use in the present invention are the Fmoc amino acids derivatives shown below.

EXAMPLES OF ORTHOGONALLY PROTECTED AMINO ACIDS USED IN SOLID PHASE SYNTHESIS

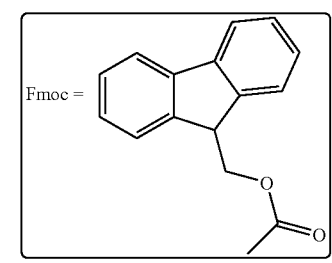

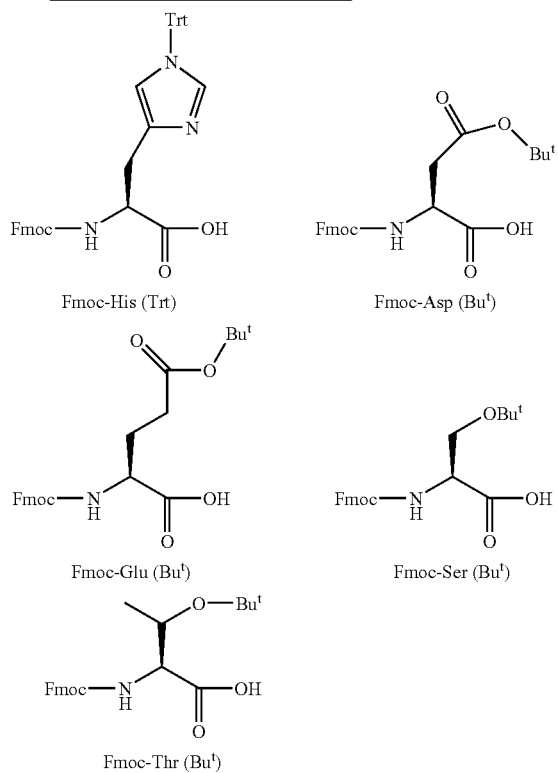

EXAMPLES OF PROTECTED AMINO ACIDS USED IN SOLID PHASE SYNTHESIS

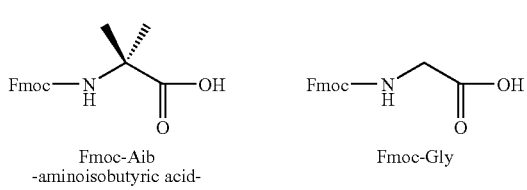

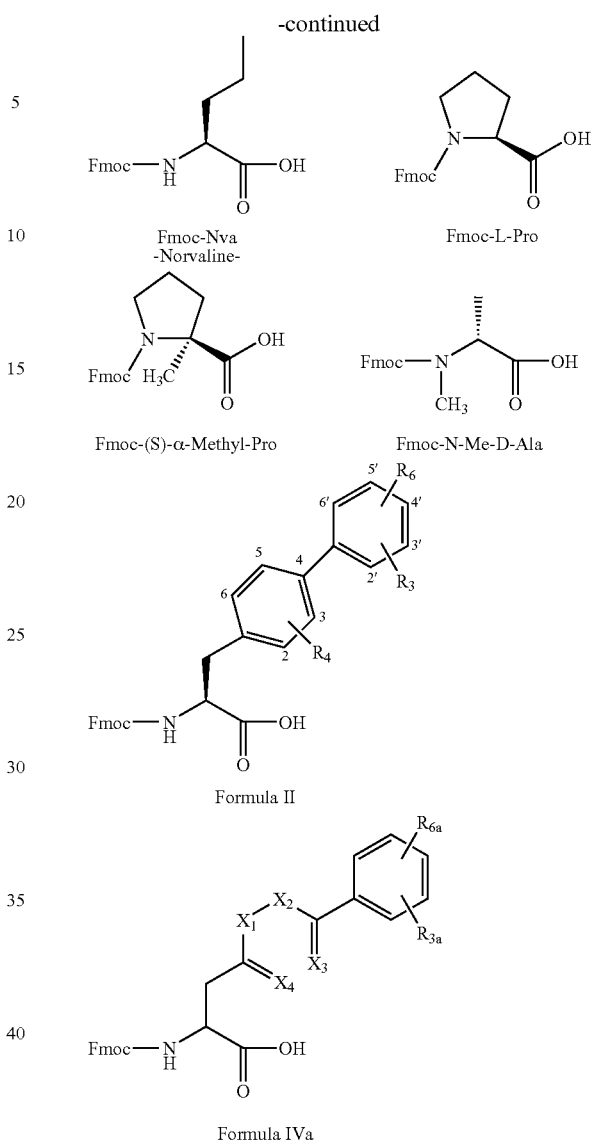

The peptidyl-resin precursors for their respective peptides may be cleaved and deprotected using any standard procedure (see, for example, D. S. King et al. *Int. J. Peptide Protein Res.* 36, 1990, 255-266). A desired method for use in this invention is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

The following abbreviations are employed in the Examples
Ph=phenyl
Bn=benzyl
i-Bu=iso-butyl
i-Pr=iso-propyl
Me=methyl
Et=ethyl
Pr=n-propyl
Bu=n-butyl
TMS=trimethylsilyl
TIS=Triisopropylsilane
$Et_2O$=diethyl ether
HOAc or AcOH=acetic acid
MeCN or $CH_3CN$=acetonitrile
DMF=N,N-dimethylformamide
EtOAc=ethyl acetate
THF=tetrahydrofuran
TFA=trifluoroacetic acid
TFE=α,α,α-trifluoroethanol
$Et_2NH$=diethylamine
NMM=N-methylmorpholine
NMP=N-methylpyrrolidone
DCM=dichloromethane
n-BuLi=n-butyllithium
Pd/C=palladium on carbon
$PtO_2$=platinum oxide
TEA=triethylamine
min=minute(s)
h or hr=hour(s)
L=liter
mL or ml=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
mp=melting point
Bip=biphenylalanine
$LiBH_4$=lithium borohydride
NBS=N-bromo-succinamide
BOP reagent=benzotriazol-1-yloxy-tris-dimethylamino-phosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyluronim hexafluorophosphate
HATU=O-(7-Azabenzotriazol-1-yl)-1,1,3,3-tetramethyluronim hexafluorophosphate
HCTU=2-(6-Chloro-1-H-benzotriazol-1-yl)-1,1,3,3-tetramethyluronium hexafluorophosphate
DMAP=4-(dimethylamino)pyridine
DIEA=Diisopropylethylamine
EDAC=3-ethyl-3'-(dimethylamino)propyl-carbodiimide hydrochloride (or 1-[(3-(dimethyl)amino)propyl])-3-ethylcarbodiimide hydrochloride)
Fmoc or FMOC=fluorenylmethyloxycarbonyl
Boc or BOC=tert-butyloxycarbonyl
Cbz=carbobenzyloxy or carbobenzoxy or benzyloxycarbonyl
HOBT or $HOBT.H_2O$=1-hydroxybenzotriazole hydrate
Cl—HOBt=6-Chloro-benzotriazole
HOAT=1-hydroxy-7-azabenzotriazole
TLC=thin layer chromatography
HPLC=high performance liquid chromatography
LC/MS=high performance liquid chromatography/mass spectrometry
MS or Mass Spec=mass spectrometry
NMR=nuclear magnetic resonance
Sc or SC=sub-cutaneous
IP or ip=intra-peritoneal
GTT=glucose tolerance test
NBS=N-Bromosuccinimide General Procedures for the Synthesis of Amino Acids of Formula IVa Protected amino acids of Formula IVa can be prepared by several methods. For example (Scheme A), iodobromo-heterocycle i (where $X_3$=N) can be coupled via palladium-mediated catalysis with a boronic acid by standard literature methods to provide aryl heterocyclic bromide ii, which by lithiation and reaction with a acylating such as dimethylformamide provides aldehyde iii. The aldehyde is reduced to alcohol iv by sodium borohydride or similar agent and the corresponding bromide v is prepared by extended refluxing of iv in 48% hydrobromic acid. Alkylation of tert-butyl 2-(diphenylmethyl-eneamino)acetate with v using a chiral catalyst after the method of O'Donnell (*Tetrahedron Letters* 39 8775 (1998)) leads to the chiral ester vi, which after deprotection with a strong non-aqueous acid and treatment with FmocCl provides Fmoc t-butyl ester vii of predominately one chiral form. Recrystallization of vii from common organic solvents provides viii with enantiomeric excess >95%. Removal of the ester using a strong non-aqueous acid provides compounds of Formula IVa.

Alternatively, compounds of Formula IVa can be prepared by radical-induced bromination of methyl heterocycle ix (Scheme B) to give bromomethylheterocycle x. Alkylation of x by the method of O'Donnell as described above and similar recrystallization leads to chiral ester xiii in high enantiomeric excess. Boronic acid coupling as described in Scheme A leads to compounds of Formula IVa.

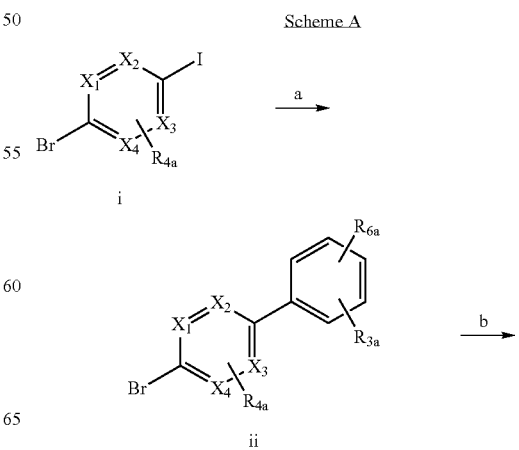

Scheme A

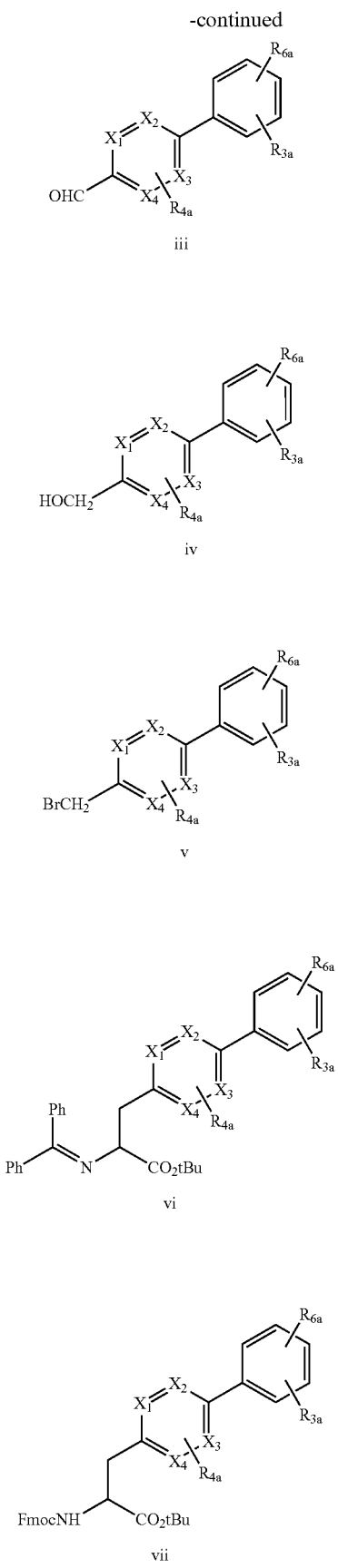
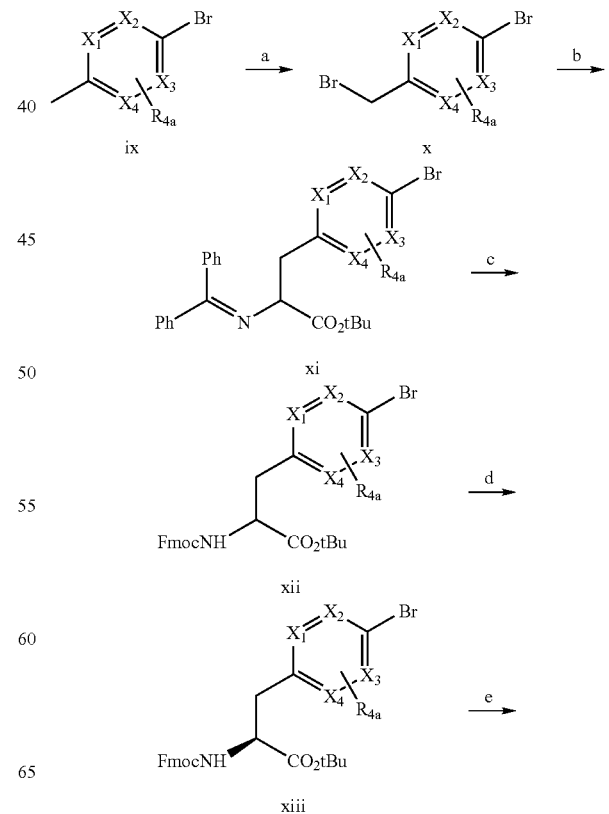
a) $R_3R_6C_6H_3B(OH)_2$, $Pd(Ph_3P)_4$, toluene/10% $Na_2CO_3$
b) s-BuLi, DMF/toluene
c) $NaBH_4$/MeOH
d) 48% HBr, reflux
e) PhC≡NCH$_2$CO$_2$tBu, chiral catalyst, 2-tert-Butylimino-2-diethylamino-1,3-dimethyl-perhydro-1,3,2-diazaphos-phorine/THF
f) i. 15% citric acid ii. FmocCl, $Na_2CO_3$/THF—$H_2O$
g) recrystallization
h) TFA
Scheme B -continued

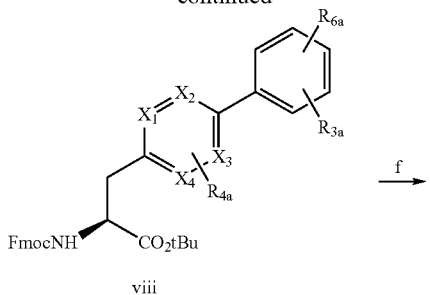

viii

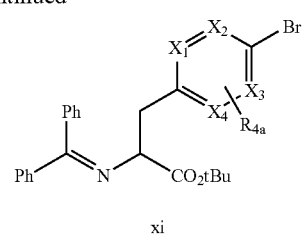

xi a) Zn—Cu(Ph₃P)₂PdCl₂, benezene, DMA

Arylpyrimidinylmethyl bromides xxiii (X₂, X₃=N, X₁, X₄=CR₄ₐ) can be prepared from aryl nitrites xv (Scheme E).

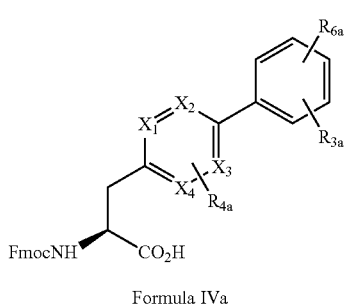

Formula IVa a) NBS, AIBN/CCl₄
b) PhC≡NCH₂CO₂tBu,
   chiral catalyst, 2-tert-Butylimino-2-diethylamino-1,3-dimethyl-perhydro-1,3,2-diazaphos-phorine/THF
c) i. 15% citric acid ii. FmocCl, Na₂CO₃/THF—H₂O
d) recrystallization
e) R₃R₆C₆H₃B(OH)₂, Pd(Ph₃P)₄, toluene/10% Na₂CO₃
f) TFA Compound ix can be prepared from hydroxyheterocycle xiv by treatment with phosphorousoxybromide (Scheme C).

Scheme C

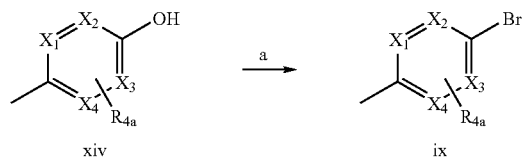

xiv          ix a) NBS, AIBN/CCl₄

An alternative synthesis of intermediate ix uses xv, methyl-3-iodo-alanate, and i by zinc-copper coupling (Scheme D).

Scheme D

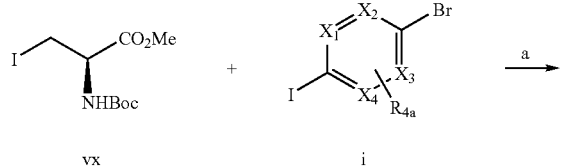

vx          i

Scheme E

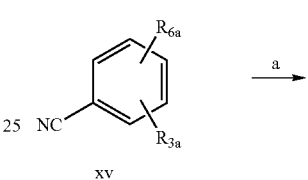

xv

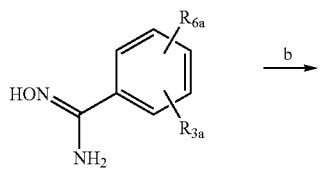

xvi

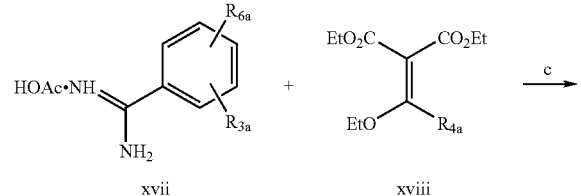

xvii          xviii

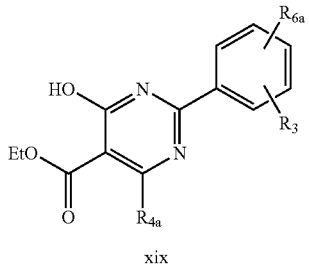

xix

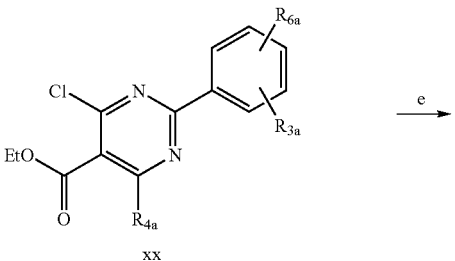

xx

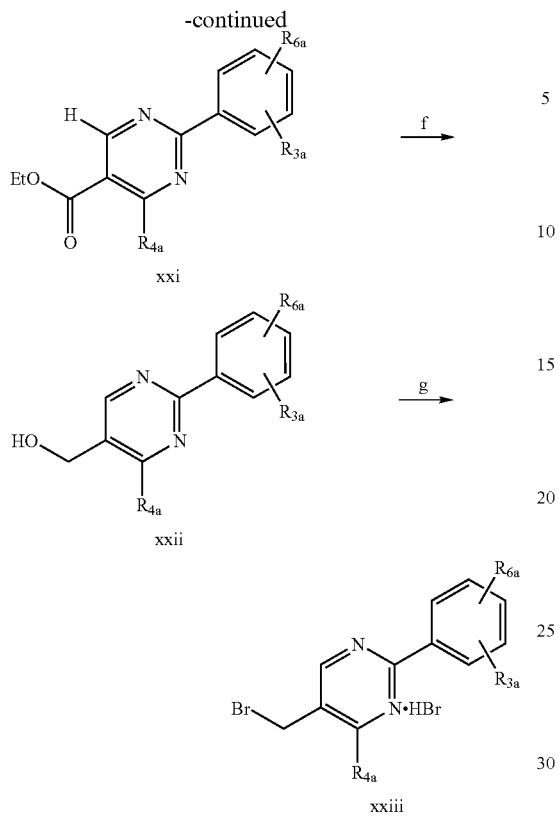

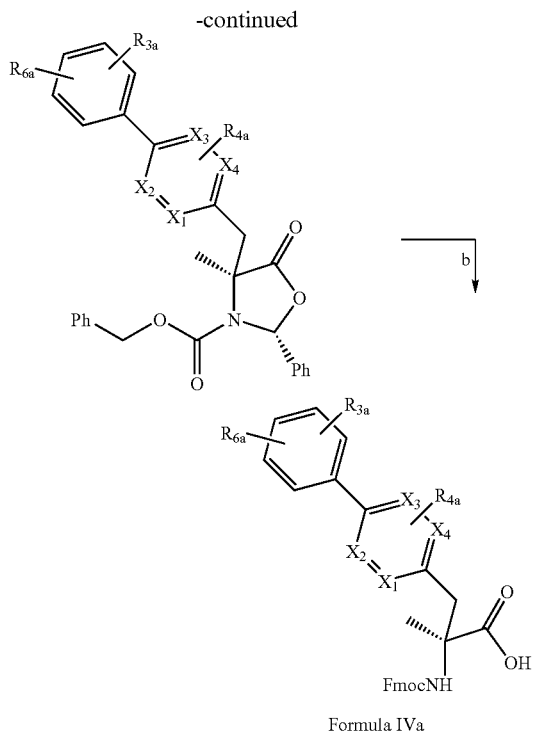

Hydroxypyrimidine xvi is prepared from xv by treatment of the nitrile with hydroxylamine hydrochloride. The pyrimidine xvii results from hydrogenation of xvi. Condensation of xvii with enolmethylene malonate xviii leads to pyrimidine xix which is chlorinated with phosphorous oxychloride to give xx. Dehalogenation via catalytic hydrogenation leads to xxi and reduction with DiBAl provides alcohol xxii. Treatment of the alcohol with phosphorous oxybromide leads to unstable bromide xxiii, which must be used immediately as in Scheme A to provide protected amino acid vi.

Compounds of Formula IVa ($R_7$=Me) are prepared from oxazolidine xxiv by the method of Kapadia, *J. Org. Chem.* 66 1903 (2001) (Scheme F). Thus alkylation of xxiv with v using potassium hexamethyldisilazide or other strong base provides xxv. Strong acid hydrolysis of xxv followed by protection (with FmocCl or FmocOSu or the like) of the amine gives compounds of the type of Formula IVa.

Scheme F

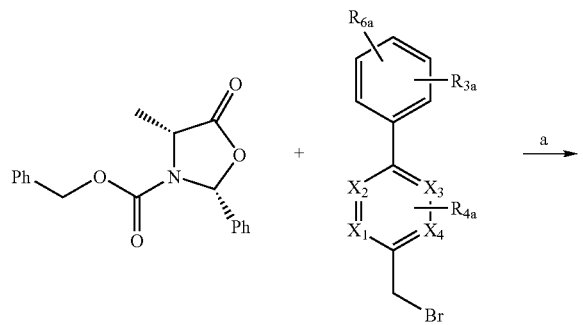

One of skill in the art of peptide chemistry is aware that amino acids occur as both D and L isomers, and that the present invention includes the use of either or a mixture of isomers for amino acids incorporated in the synthesis of the peptides described herein.

EXAMPLE 1

Simultaneous Solid Phase Peptide Synthesis of 11-mer Peptides

Dipeptidyl resin, containing, amino acid at positions $Xaa_{10}$ and $Xaa_{11}$, was prepared using the following manual procedure in a batchwise mode before continuing peptide chain elongation utilizing the automated simultaneous synthesis protocol on an MPS-396 peptide synthesizer. The synthesis of the N-α-Fmoc-protected biphenylalanine or phenyl-heteroaryl-alanine derivatives used in the manual couplings is described in the general experimental above, and as in Examples 10-16 and Examples 21-22.

An amount of 9-Fmoc-aminoxanthen-3-yloxy-Merrifield resin (Sieber amide resin; loading: 0.5 to 0.7 mmol/g) sufficient to synthesize several 11-mer analogs, was swelled by washing with DMF (4×10 mL/g, 5 minutes). The Fmoc group was then removed using two treatments, 5 and 15 minutes each respectively, with 20% piperidine in DMF (10 mL/g). The resin was washed with DMF (4×10 mL/g) and NMP (4×10 mL/g). A 0.5 M solution of Fmoc-L-4-(2'-Methylphenyl)-3-pyridylalanine-OH(HCl salt)(1.1 eq.), (or of any other amino acid represented by Formula IVa), PyBOP (1.1 eq.) and DIEA (3.3 eq.) in NMP was added to the resin. The resin was then shaken or vortexed for 16-24 hours. Coupling completion was monitored using a qualitative ninhydrin test. The resin was drained, washed with NMP (3×10 mL/g) and DMF (3×10 mL/g), and treated for 90 minutes with 10% acetic anhydride in DCM (10 mL/g). After DCM washes (4×10 mL/g), a second manual coupling cycle using a DIC/

HOAt mediated was then performed, starting from the removal of the Fmoc group with 20% piperidine in DMF, and using a Fmoc-protected biphenylalanine analog, as represented by Formula II, in the coupling step. This synthesis scheme produced the desired Fmoc-protected dipeptidyl-Sieber amide resin.

Such dipeptidyl-resins required for the synthesis of a set of designed analogs were then used in the automated MPS synthesis of up to 96 peptides per run in the following manner. The dipeptidyl-resins were loaded as suspensions in dichloromethane/DMF (60:40) into the 96-well reactor of an Advanced ChemTech MPS 396 synthesizer in volumes corresponding to 0.01-0.025 mmol (20-50 mg) of resin per reactor well. The reactor was placed on the instrument and drained. The wells were then washed with DMF (0.5-1.0 mL, 3×2 min) and subjected to the number of automated coupling cycles required to assemble the respective peptide sequences as determined by the pre-programmed sequence synthesis table.

The detailed stepwise synthesis protocol used for a typical 0.025 mmol/well simultaneous synthesis of 96 compounds is described below. This protocol was adapted for the simultaneous synthesis of arrays of analogs ranging from 12 to 96 per individual run. The general synthesis protocol is depicted in Scheme 1.

Scheme 1. Automated synthesis of GLP-1 receptor modulator peptide analogs

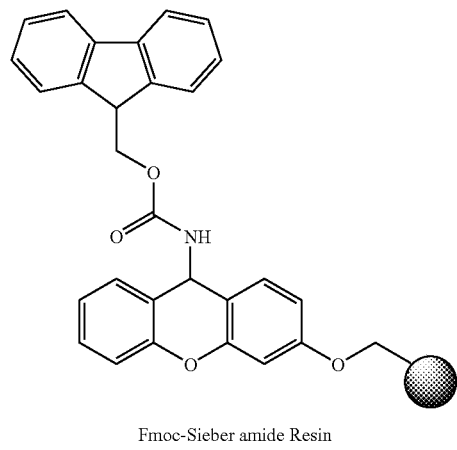

Fmoc-Sieber amide Resin

1) Piperidine/DMF (Removal of Fmoc)
2) 1.1 eq. Fmoc-(S)-4-(2'-methylphenyl)-3-pyridylIala/PyBOP/DIEA/NMP (16 h);
3) (a) repeat step1; (b) 2–4 eq. Fmoc-(S)-Bip(2'-Et-4'-OMe)/DIC/HOAt/NMP (16 hr);
4) (a) repeat step 1: (b) 5 eq. Fmoc-Xaa$_9$/DIC/HOBt (2 hr);
5) repeat step 4 using Fmoc-Xaa$_8$;
6) repeat step 4 using Fmoc-Xaa$_7$;
7) (a) repeat step 1; (b) Xaa$_6$/HOAt/DIC (2 hr);
8) (a) repeat step 1; (b) 10 eq. Fmoc-Xaa$_5$/HOAt/DIC (4 hr);
   (c) 10% Ac$_2$O/DCM (30 min) [unreacted amine capping step];
9) repeat step 1; (b) 10 eq. Fmoc-Xaa$_4$/HOAt/DIC (2 hr);
10) repeat step 9 using Fmoc-Xaa$_3$;
11) repeat step 1; (b) 5 eq. Fmoc-Xaa$_2$/HOAt/DIC (16 hr);
12) repeat step 11 using Fmoc-Xaa$_1$/HOAt/DIC;
13) (a) repeat step 1; (b) wash with NMP and DCM; (c) dry in vacuo;
14) TFA/Water/Triisopropylsilane (2 hr);
15) RP-HPLC purification Xaa1-Xaa2-Xaa3-Xaa4-Xaa5-Xaa6-Xaa7-Xaa8-Xaa9-Xaa10-Xaa11

Prior to starting the synthesis, the following reagent solutions were prepared and placed on the instrument as required: 1.5 M (15%) piperidine in DMF; 0.5 M DIEA in NMP; 0.36 M DIC in NMP; 1 M (10%) acetic anhydride in DMF. The required Fmoc-protected amino acids were prepared as 0.36 M solutions in 0.36 M HOAt/NMP and placed into the appropriate positions in the 32-position amino acid rack.

The Fmoc-protected dipeptidyl-resin prepared above was deprotected by treating with 20% piperidine in DMF (1.0 mL; 1×5 minutes; 1×15 minutes). The resin was then washed with NMP (8×1.0 mL).

Coupling of the next amino acid, typically Fmoc-Asp(OtBu)-OH or another Fmoc-amino acid with appropriate orthogonal protection if required, was carried out by manual addition of a solution of the appropriate Fmoc-amino acid (0.075 mmol, 3.0 eq.), HCTU (0.075 mmol, 3.0 eq.) and DIEA (0.15 mmol, 6.0 eq.) in NMP (1 mL) to all wells. The coupling was allowed to proceed for 3 hrs. After reactor draining by nitrogen pressure (3-5 psi) and washing the wells with NMP (4×1.0 mL).

The next coupling cycle started with the removal of the Fmoc group as described above, and involved the coupling of either Fmoc-Ser(tBu)-OH or of a different Fmoc-amino acid as required by the sequence substitutions desired at this position. The coupling was carried out in a manner identical to that described for Fmoc-Asp(OtBu)-OH. The next coupling step was carried out in the same way to incorporate either Fmoc-Thr(tBu)-OH or any of the other selected Fmoc-amino acids into this sequence position as required.

The next Fmoc-amino acid (for example Fmoc-α-methyl-Phe-OH or an analog thereof) was coupled as follows: after Fmoc deprotection in the usual manner, the Fmoc-amino acid (1-5 eq.), HOAt (1-5 eq.) and DIC (1-5 eq.) were added manually as a solution in NMP (1.0 mL) and the coupling was allowed to proceed for 16-24 hrs. The coupling was not repeated in this case. After the usual post-coupling washes, the peptidyl-resins were capped with acetic anhydride as described herein.

The next coupling step involved either Fmoc-Thr(tBu)-OH or substitution analogs as required by sequence replacements at this position. The coupling was performed as described for the initial MPS coupling of Fmoc-Asp(OtBu)-OH and its analogs, except that 10 eq. of Fmoc-Thr(tBu)-OH or substitution analogs was used and the coupling was allowed to proceed for 16 hrs and the coupling reagents used were DIC/HOAt in NMP. After the usual post-coupling washes, the peptidyl-resins were capped with 10% acetic anhydride in DCM (1×1 mL×60 mins.).

The identical coupling protocol described for the coupling of Fmoc-Asp(OtBu)-OH was used was repeated for the next three amino acid residues. Fmoc-His(Trt)-OH was coupled as the Fmoc-Thr(tBu)-OH residue described in the paragraph above in order to complete the sequence assembly of the desired 11-mer peptide analogs. For the coupling of commercially and non-commercially available non-natural amino acids needed at a certain sequence position, a single coupling protocol similar to that described above for the novel amino acid at position 6 ($X_{aa6}$) was used.

Finally, the Fmoc group was removed with 20% piperidine in DMF as described above, and the peptidyl-resins were washed with DMF (4×1.0 mL) and DCM (4×1.0 mL). They were then dried on the reactor block by applying a constant pressure of nitrogen gas (5 psi) for 10-15 min.

a. Cleavage/Deprotection.

The desired peptides were cleaved/deprotected from their respective peptidyl-resins by treatment with a TFA cleavage mixture as follows. A solution of TFA/DCM/tri-isopropylsilane (70:28:2) (1.0 mL) was added to each well in the reactor block, which was then vortexed for 10 mins. This was repeated twice more and the TFA solutions from the wells were collected by positive pressure into pre-tared vials located in a matching 96-vial block on the bottom of the reactor. The vials were capped and gently vortexed for an additional 90 minutes. The vials were uncapped and concentrated in a SpeedVac™ (Savant) to a volume of about 0.2 mL. The crude peptides were then precipitated by the addition of diisopropyl ether (3 mL) and being briefly vortexed. The precipitates were pelleted by centrifugation and the supernatants were decanted. The vials were dried in a SpeedVac™ (Savant) to yield the crude peptides, typically in >100% yields (20-40 mgs). The crude peptides dissolved directly in 2 mL of 0.6% ammonium hydroxide for purification by preparative HPLC as follows.

b. Preparative HPLC Purification of the Crude Peptides

Preparative HPLC was carried out either on a Waters Model 4000 or a Shimadzu Model LC-8A liquid chromatograph. Each solution of crude peptide was injected into a YMC S5 ODS (20×100 mm) column and eluted using a linear gradient of MeCN in water, both buffered with 0.1% TFA. A typical gradient used was from 20% to 50% 0.1% TFA/MeCN in 0.1% TFA/water over 15 min. at a flow rate of 14 mL/min with effluent UV detection at 220 nm. The desired product eluted well separated from impurities, typically after 10-11 min., and was usually collected in a single 10-15 mL fraction on a fraction collector. The desired peptides were obtained as amorphous white powders by lyophilization of their HPLC fractions.

c. HPLC Analysis of the Purified Peptides.

After purification by preparative HPLC as described above, each peptide was analyzed by analytical RP-HPLC on a Shimadzu LC-10AD or LC-10AT analytical HPLC system consisting of: a SCL-10A system controller, a SIL-10A autoinjector, a SPD10AV or SPD-M6A UV/VIS detector, or a SPD-M10A diode array detector. A YMC ODS S3 (4.6×50 mm) column was used and elution was performed using one of the following gradients: 10-70% B in A over 8 min, 2.5 mL/min. (method A); 5-80% B in A over 8 min, 2.5 mL/min. (method B); 5-70% B in A over 8 min., 2.5 mL/min. (method C); 25-75% B in A over 8 min, 2.5 mL/min (method D); 20-75% B in A over 8 min, 2.5 mL/min. (method E); 15-70% B in A over 8 min, 2.5 mL/min. (method F); 10-90% B in A over 8 min, 2.5 mL/min. (method G); 20-65% B in A over 8 min, 2.5 mL/min. (method H); 5-90% B in A over 8 min., 2.0 mL/min. (method I); 5-90% B in A over 8 min., 2.5 mL/min. (method J); 20-80% B in A over 8 min., 2.5 mL/min. (method K); 10-100% B in A over 8 min., 2.5 mL/min. (method L); 10-75% B in A over 8 min., 2.5 mL/min. (method M). Mobile phase A: 0.1% TFA/water; mobile phase B: 0.1% TFA/acetonitrile. The purity was typically >90%.

d. Characterization by Mass Spectrometry.

Each peptide was characterized by electrospray mass spectrometry (ES-MS) either in flow injection or LC/MS mode. Finnigan SSQ7000 single quadrupole mass spectrometers (ThermoFinnigan, San Jose, Calif.) were used in all analyses in positive and negative ion electrospray mode. Full scan data was acquired over the mass range of 300 to 2200 amu for a scan time of 1.0 second. The quadrupole was operated at unit resolution. For flow injection analyses, the mass spectrometer was interfaced to a Waters 616 HPLC pump (Waters Corp., Milford, Mass.) and equipped with an HTS PAL autosampler (CTC Analytics, Zwingen, Switzerland). Samples were injected into a mobile phase containing 50:50 water:acetonitrile with 0.1% ammonium hydroxide. The flow rate for the analyses was 0.42 mL/min. and the injection volume 6 μl. A ThermoSeparations Constametric 3500 liquid chromatograph (ThermoSeparation Products, San Jose, Calif.) and HTS PAL autosampler were used for LC/MS analyses. Chromatographic separations were achieved employing a Luna $C_{18}$, 5 micron column, 2×30 mm (Phenomenex, Torrance, Calif.). The flow rate for the analyses was 1.0 mL/min and column effluent was split, so that the flow into the electrospray interface was 400 μl/min. A linear gradient from 0% to 100% B in A over 4 minutes was run, where mobile phase A was 98:2 water:acetonitrile with 10 mM ammonium acetate and mobile phase B was 10:90 water:acetonitrile with 10 mM ammonium acetate. The UV response was monitored at 220 nm. The samples were dissolved in 200 μl 50:50 $H_2O$:MeCN (0.05% TFA). The injection volume was 5 μl.

In all cases, the experimentally measured molecular weight was within 0.5 Daltons of the calculated monoisotopic molecular weight.

EXAMPLE 2

A. General procedure for the Synthesis of N-Acylated 11-mer Peptide Analogs (Scheme 2)

The synthesis of the N-acylated 11-mer peptide analogs was started from the protected 11-mer peptidyl-resin intermediate (1) (0.015 mmol), prepared as described herein, as shown in Scheme 2. The Fmoc group was removed using the procedure described herein, and the resulting resin intermediate 2 was coupled with the relevant Fmoc-protected amino acid or carboxylic acid using the coupling protocol described in the general method described herein. In cases where the appropriate anhydride was available, the N-acylation was performed using 5 eq. of the anhydride in NMP. The resulting N-acylated 11-mer analogs (3) were cleaved/deprotected and purified by prep. HPLC by the general method described herein.

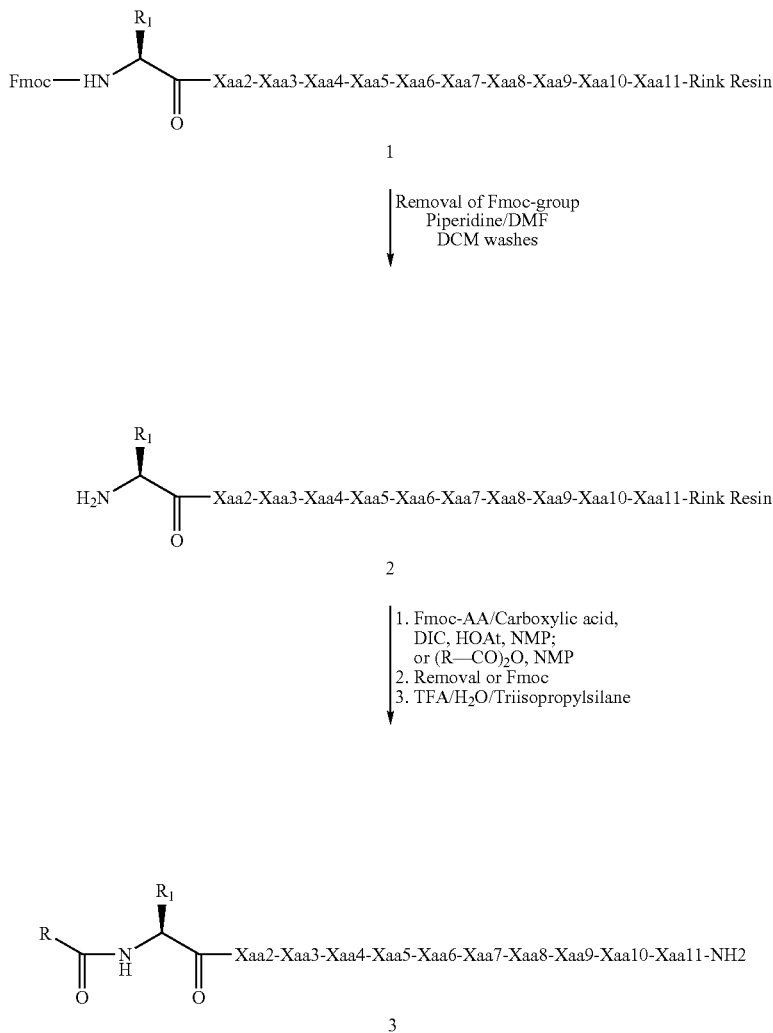

B. General Procedure for the Synthesis of N-Carbamate Derivatives of 11-mer Peptide Analogs.

The synthesis of N-carbamate derivatives of 11-mer peptide analogs may be started from the protected 11-mer peptidyl-resin intermediate (1) (0.015 mmol), prepared as described herein. The Fmoc group is removed using the procedure described herein, and the resulting resin intermediate 2 is allowed to react with the relevant chloroformate in the presence of an appropriate base such as a tertiary amine, or with a di-carbonate or an activated carbonate such as p-nitrophenyl or phenyl or hydroxy-succinimidyl carbonate.

C. General Procedure for the Synthesis of N-Urea Derivatives of 11-mer Peptide Analogs.

The synthesis of N-urea derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant isocyanate prepared, for example, as in K. Burgess et al., *J. Am. Chem. Soc.* 1997, 119, 1556-1564; alternatively, the resin intermediate 2 may be allowed to react with the relevant carbamoyl chloride. Similarly, N-urea derivatives of 10-mer peptide analogs may be prepared starting from a protected 10-mer peptidyl-resin intermediate, Fmoc removal and reaction of the resulting peptidyl-resin intermediate with the relevant isocyanate or carbamyl chloride.

D. General Procedure for the Synthesis of N-Sulfonamides of 11-mer Peptide Analogs.

The synthesis of N-sulfonamides of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant sulfonyl chloride. Similarly, N-sulfonamides of 10-mer peptide analogs may be prepared starting from a protected 10-mer peptidyl-resin intermediate, Fmoc removal and reaction of the resulting peptidyl-resin intermediate with the relevant sulfonyl chloride.

E. General Procedure for the Synthesis of N-Sulfonylurea Derivatives of 11-mer Peptide Analogs.

The synthesis of N-sulfonylurea derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant sulfamoyl chloride $R_4R_5N-SO_2-Cl$ to yield a sulfonyl urea intermediate (see, for example, P. Davern et al. J. Chem. Soc., Perkin Trans. 2, 1994 (2), 381-387). Similarly, N-sulfonyl urea derivatives of 10-mer peptide analogs may be prepared starting from a protected 10-mer peptidyl-resin intermediate, Fmoc removal and reaction of the resulting peptidyl-resin intermediate with the relevant sulfamoyl chloride $R_4R_5N-SO_2-Cl$.

EXAMPLE 3

Solid Phase Synthesis of 11-mer Peptide Analogs Using an Applied Biosystems Model 433A Peptide Synthesizer Following is the general description for the solid phase synthesis of typical 11-mer peptide analogs, using an upgraded Applied Biosystems Model 433A peptide synthesizer. The upgraded hardware and software of the synthesizer enabled conductivity monitoring of the Fmoc deprotection step with feedback control of coupling. The protocols allowed a range of synthesis scale from 0.05 to 1.0 mmol.

The incorporation of the two non-natural C-terminal amino acid was described above in connection with simultaneous synthesis of 11-mer analogs. Such a Fmoc-protected dipeptidyl resin was used in this ABI synthesis. The Fmoc-protected dipeptidyl-resin (0.1 mmol) was placed into a vessel of appropriate size on the instrument, washed 6 times with NMP and deprotected using two treatments with 22% piperidine/NMP (2 and 8 min. each). One or two additional monitored deprotection steps were performed until the conditions of the monitoring option were satisfied (<10% difference between the last two conductivity-based deprotection peaks). The total deprotection time was 10-12 min. The deprotected dipeptidyl-resin was washed 6 times with NMP and then coupled with the next amino acid. The procedure is illustrated by the example used in the next step.

Thus, Fmoc-Asp(OtBu)-OH was coupled next using the following method: Fmoc-Asp(OtBu)-OH (1 mmol, 10 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP, and subjected to 8 additional deprotection/coupling cycles as described above in order to complete the assembly of the desired sequence. The Fmoc-amino acids sequentially used were: Fmoc-Ser(tBu)-OH, Fmoc-Thr(tBu)-OH, Fmoc-α-methyl-Phe(2-Fluoro)-OH or analog thereof, Fmoc-Thr(tBu)-OH, Fmoc-Gly-OH, Fmoc-Glu(OtBu)-OH, Fmoc-Aib-OH and Fmoc-His(Trt)-OH. Finally, the Fmoc group was removed with 22% piperidine in NMP as described above, and the peptidyl-resin was washed 6 times with NMP and DCM, and dried in vacuo.

Alternatively, a modified coupling protocol was used in which the Fmoc-protected amino acid (0.26 mmol) was activated by subsequent addition of 0.5 M HOAt in DMF (0.52 mL) and DIC (40 µL), transferred to the reaction vessel manually and allowed to couple for 14-18 hrs.

A. Cleavage/Deprotection

The desired peptide was cleaved/deprotected from its respective peptidyl-resin by treatment with a solution of TFA/water/tri-isopropylsilane (96:2:2) (3.0 mL) for 2 hrs. The resin was filtered off, rinsed with TFA (1.0 mL), and the combined TFA filtrates were added to 35 mL of $Et_2O$. The resulting precipitate was collected by centrifugation and finally dried, to yield 232 mg of crude peptide product as a white solid. This was purified by preparative HPLC as described herein. The gradient used was from 15% to 45% 0.1% TFA/MeCN in 0.1% TFA/water over 40 min. The fractions containing pure product were pooled and lyophilized, to yield 28.4 mg (18% recovery) of pure product.

EXAMPLE 4

Synthesis of Biphenylalanine and Phenyl-Heteroaryl-Alanine Analogs at Position-Xaa10 and Position-Xaa11 Represented by Formulas II and IVa For those analogs wherein position-Xaa10 and position-Xaa11 residues were represented by substituted amino acid analogs represented by Formulas II and IVa, i.e. biphenylalanine analogs (Bip analogs) or phenyl-heteroaryl-alanine analogs, their incorporation into the peptide chain was carried out in one of the following two approaches.

A. Approach A: Solid Phase Suzuki Condensation.

In approach A, solid phase Suzuki condensation was practiced to prepare the required modified biphenylalanine or phenyl-heteroaryl-alanine residue in a manner suitable for carrying out subsequent solid phase peptide synthesis to obtain the target peptides. When the amino acid at position-Xaa11 in the target peptide was represented by a modified biphenylalanine or phenyl-heteroaryl-alanine residue, it was prepared as shown in Scheme 3. After removal of the Boc α-amine protecting group, chain elongation was continued using multiple peptide synthesis as described in the previous section to obtain the desired 11-mer peptides or its derivatives thereof. When the modified biphenylalanine analog was in position Xaa10 of the target peptides, the required amino acid was prepared using a suitable dipeptide precursor on solid support as shown in Scheme 4.

The resulting dipeptidyl segment containing the required modified biphenylalanine derivative was then used to carry out the synthesis of the target 11-mer peptide or its derivatives thereof. When both position-Xaa10 and position-Xaa1 required novel biphenylalanine or phenyl-heteroaryl-alanine residues, two sequential solid phase Suzuki reactions were carried out as shown in Scheme 5 (below).

1. General Procedure for Preparation of SynPhase™ Lanterns Containing Amino Acids Represented by Formula IVa at Position-Xaa11 (Suzuki Couplings).

Scheme 3

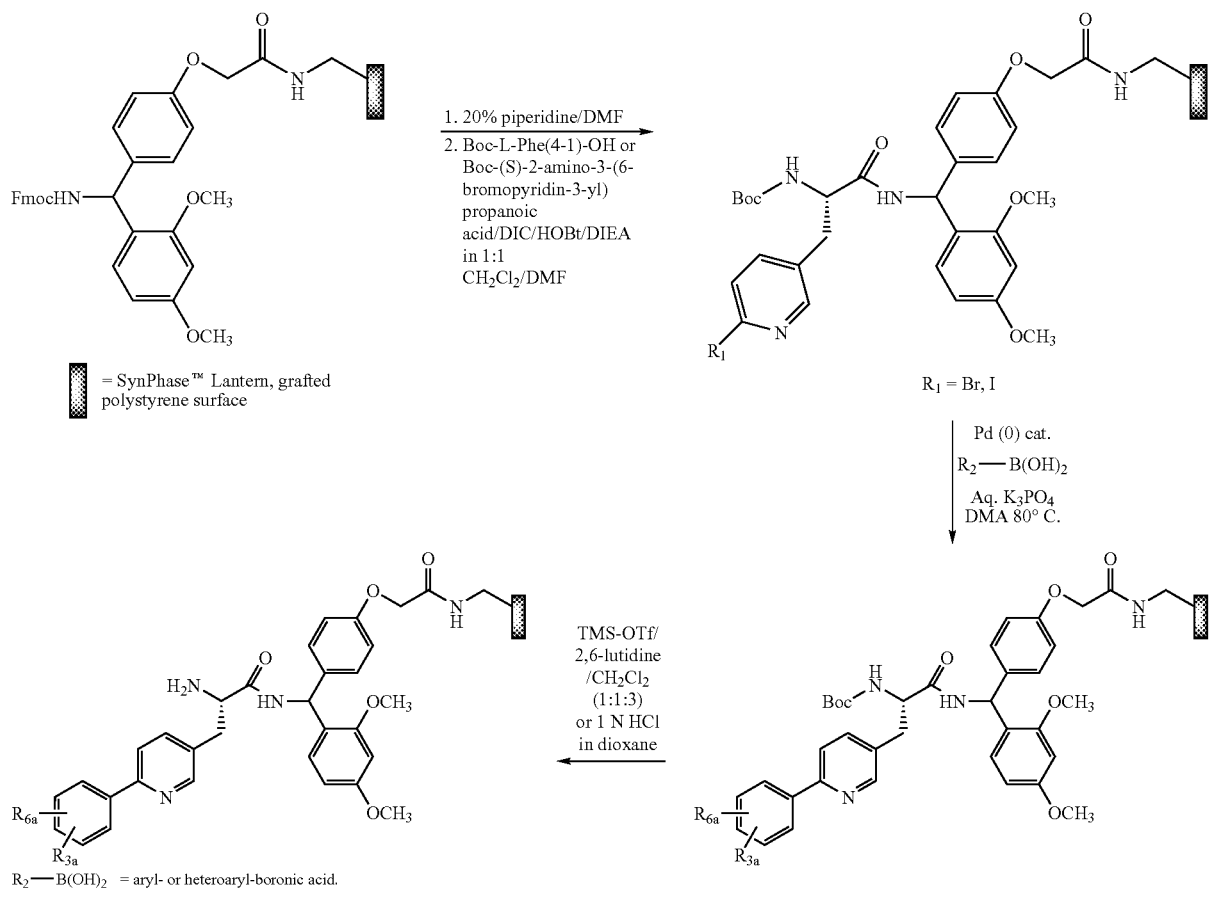

a. General Procedure A.

SynPhase™ Lanterns (A-series (0.075 mmole/lantern) or D-series (0.035 mmole/lantern), from Mimotopes) derivatized with an $N^\alpha$-Boc-(S)-2-amino-3-(6-bromopyridin-3-yl) propanoic acid residue or $N^\alpha$-Boc-L-4-iodophenylalanine residue either attached directly via a Knorr linkage (Boc-amino acid-resin) or via an amino acid-Knorr linkage (Boc-dipeptide-resin) were placed into 13×100 mm glass culture tubes with screw caps. (The following procedure was used for D-series lanterns. Similar ratios of reactants were used for reactions involving A-series lanterns.) Aryl- or heteroaryl-boronic acids (0.140 mmole, 4 equivalents) were dissolved in 0.30 ml of N,N-dimethylacetamide. The resulting solutions were added to the lanterns in the 13×100 mm glass culture tubes.

Potassium phosphate (0.280 mmole, 8 equivalents, 0.14 ml of a 2 M aqueous solution) was added to the aryl- or heteroaryl-boronic acid solution, followed by 0.10 ml of an N,N-dimethylacetamide solution containing 4.0 mg of tetrakis(triphenylphosphine)palladium(0) catalyst (ca. 10 mole %, 0.0035 mmol). The resulting mixtures were blanketed with nitrogen, and the reaction vessels were tightly capped and maintained at 80° C. for 17-20 hours while placed on an orbital shaker. The lanterns were transferred to a filter apparatus, and washed with 3×1 ml of N,N-dimethylacetamide and 3×1 ml of dichloromethane (per lantern, minimum of 3 minutes/wash cycle) prior to Boc group cleavage (see General Procedure below).

b. General Procedure B.

The reactions were performed as in General Procedure A except a different catalyst was employed. For this procedure, the dichlorobis(triphenylphosphine)palladium(II) was used as the catalyst. For the D-series lantern scale reactions, ca. 10 mol % (0.0035 mol) catalyst was used.

2. Procedures for Cleavage of the Boc Group a. Method A.

(The following procedure applies to D-series lanterns, 0.035 mmol/lantern. A similar, appropriately scaled procedure was used for A-series lanterns, 0.075 mmol/lantern.) The Boc-protected lanterns prepared as described in General Procedures A or B were treated with 0.5 ml of a reagent solution consisting of trimethylsilyl trifluoromethanesulfonate, 2,6-lutidine and dichloromethane (1:1:3 by volume). After 2 such reagent treatments for 1 hour each with mild agitation, the resins were washed with 4×1.0 ml of dichloromethane, 3×1.0 ml of N,N-dimethylformamide, and 3×1.0 ml dichloromethane. The lanterns were then subjected to the next acylation (coupling reaction) in the peptide synthesis sequence.

b. Method B.

The Boc-protected lanterns prepared as described in General Procedures A or B were treated with 0.5 ml of 1 N HCl in anhydrous 1,4-dioxane for 1 hour at room temperature with mild agitation. The lanterns were washed with 2×1.0 ml of 1,4-dioxane, 2×1.0 ml of 10% N,N-diisopropylethylamine in N,N-dimethylacetamide (vol:vol), 3×1.0 ml of N,N-dimethylacetamide, and 3×1.0 ml of dichloromethane to provide the free amino-lanterns ready for the next acylation (coupling reaction) step.

EXAMPLE 6

General Procedure for Preparation of a Lantern Containing a Modified Biphenylalanine Residue at Position-Xaa10

The General Procedures described above (A and B) for Suzuki coupling were utilized to obtain the required dipeptidyl lantern containing modified Phe at position-Xaa10 starting with the amino acid (at position-Xaa11) bound to SynPhase™ Lantern as shown in Scheme 4.

Scheme 4

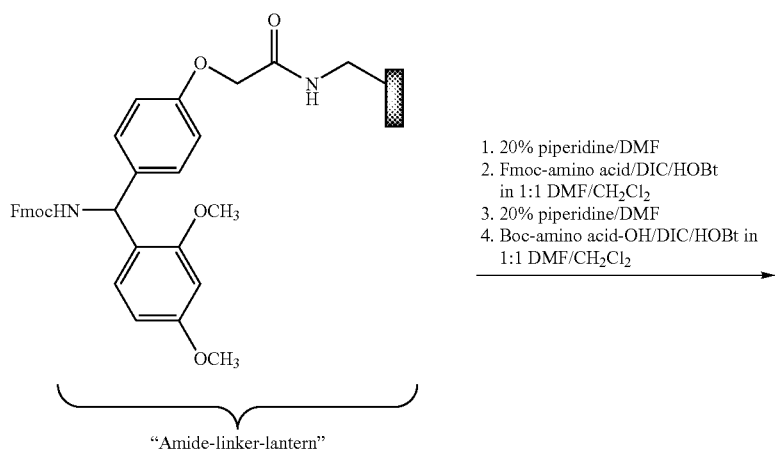

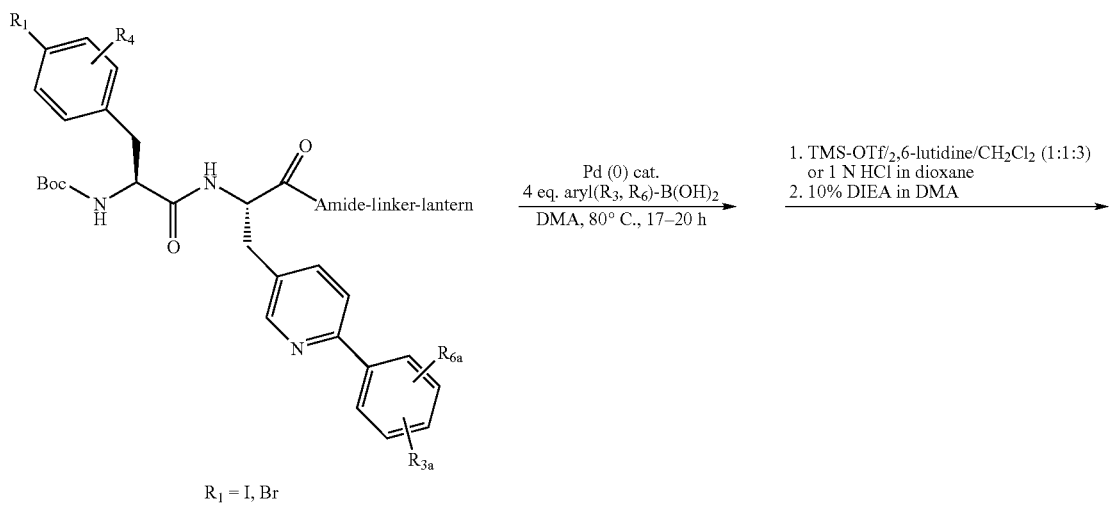

-continued

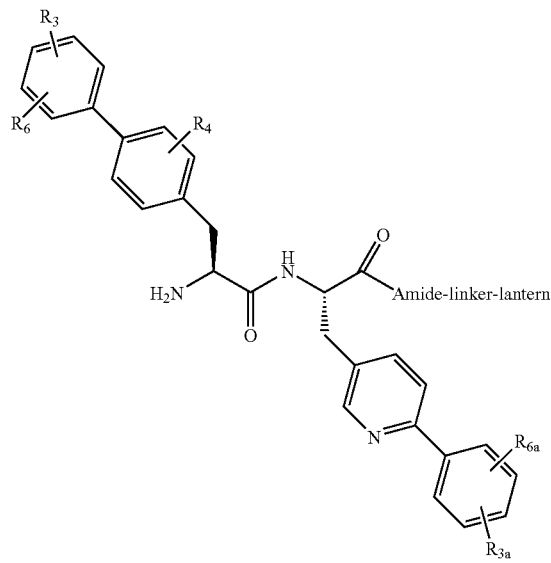

$R_3$, $R_4$, $R_6$, $R_{3a}$, and $R_{6a}$ are represented by the side chains described in Formulas II and IVa;

EXAMPLE 7

General Procedure for Preparation of Lantern Containing Amino Acids Represented by Formula II and Formula IVa at Both Positions-Xaa10 and -Xaa11

Utilizing the procedures described above for position-Xaa11 modified analogs (Scheme 1) and carrying out the Suzuki coupling procedure two successive times produced dipeptidyl lanterns containing modified phenylalanine and phenyl-heteroaryl alanine residues at both positions-Xaa10 and -Xaa11 as illustrated in Scheme 5, below.

EXAMPLE 8

General Procedures for Acylation/Elongation of Peptides on SynPhase™ Lanterns a. Procedure for Fmoc-Deprotection A D-series SynPhase™ Lantern (0.035 mmol/lantern loading) was added to 0.5 ml 8:2 N,N-dimethylformamide/piperidine (vol:vol). Mild agitation was applied. After 1 h, the lantern was washed with 3×1.0 ml N,N-dimethylformamide and 3×1.0 ml dichloromethane, allowing lantern to soak at least 3 min/wash.

b. Procedure for Acylation/Amino Acid Coupling (Scheme 6).

A side chain and α-amine protected amino acid (0.105 mmol) was dissolved in 0.5 ml 1:1 N,N-dimethylformamide/dichloromethane. To this solution was added N-hydroxybenzotriazole (0.105 mmol), N,N-diisopropylethylamine (0.315 mmol), and N,N'-diisopropylcarbodiimide (0.105 mmol). The amino acid solution was allowed to sit for 10 minutes, after which a D-series lantern containing α-amine deprotected peptide (0.035 mmol/lantern) was added to the solution. The vial was capped and gently agitated for 16-20 h. The lantern was then washed with 3×1.0 ml N,N-dimethylformamide and 3×1.0 ml dichloromethane, letting lantern soak for 3-5 min/wash cycle.

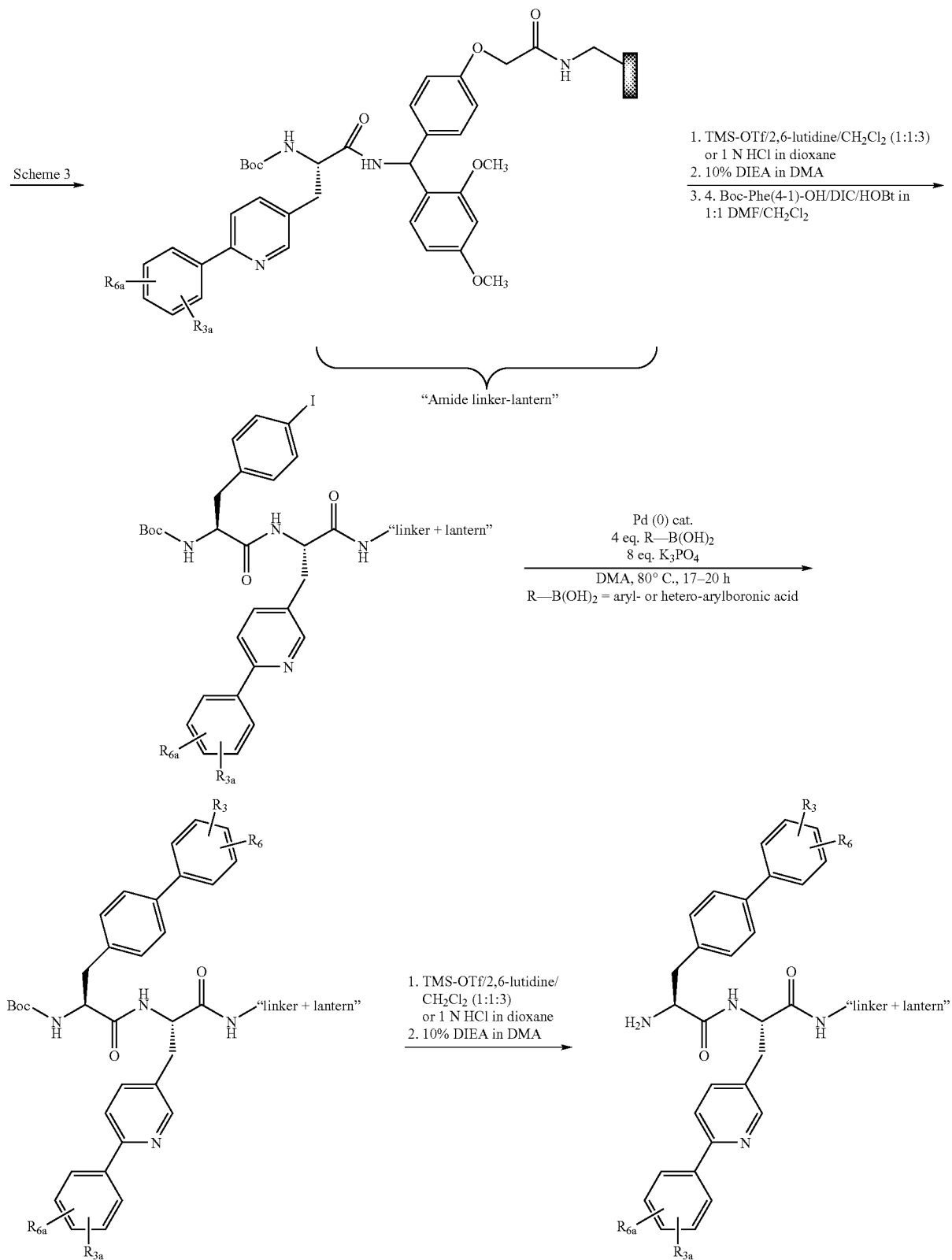
Scheme 5
$R_3$, $R_6$, $R_{3a}$, and $R_{6a}$ are represented by the side chains described in Formulas II and IVa.

Scheme 6
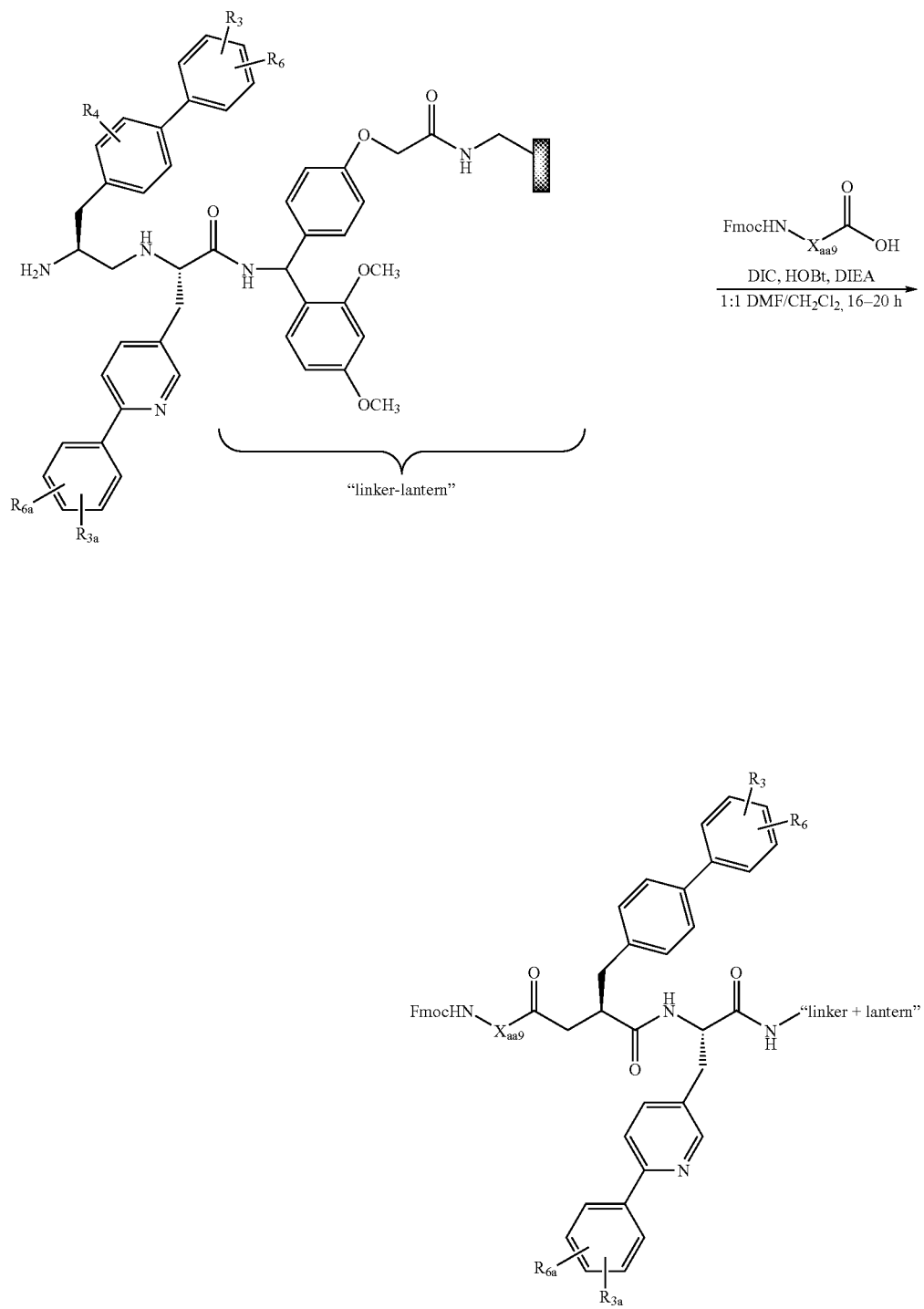
"linker-lantern"
R$_3$, R$_4$, R$_6$, R$_{3a}$, and R$_{6a}$ are represented by the side chains described in Formulas II and IVa.

EXAMPLE 9

General Procedure for Preparation of Peptides Via Fragment Condensation

In approach A, solid phase Suzuki condensation was practiced to prepare the required amino acids represented by Formula II Formula IVa at positions Xaa10 and Xaa11, as described in Example 7. The dipeptide was cleaved from support, with either simultaneous (procedure A) or subsequent (procedure B) removal of the N-terminal α-amine protecting group. The dipeptide was then coupled to a fully side chain-protected 9 amino acid peptide (vide infra). Subsequent deprotection of side chains and purification resulted in the desired 11-mer peptide products.

A. Approach A: Solution Phase Fragment Condensation.

In Approach A, solid phase Suzuki condensations and acylations were performed (as described in Example 7) to prepare the desired dipeptides bound to Synphase™ Lanterns, with the N-terminal α-amine either Boc-protected or Fmoc-protected. The dipeptides were cleaved from the Lantern support under acidic conditions. In the case of Boc-protected N-terminal α-amines, the acidic cleavage afforded simultaneous deprotection of the α-amine as shown in Scheme 7, and these were either purified or carried directly into the fragment coupling sequence.

The dipeptides containing Fmoc-protected N-terminal α-amines were cleaved under acidic conditions and the N-terminal α-amine was deprotected in solution, as shown in Scheme 8. These dipeptides were purified, then carried into the fragment coupling sequence.

1. Procedures for Cleavage of Dipeptides from SynPhase™ Lanterns.

a. Procedure A (Boc-Protected Dipeptides; see Scheme 7).

The D-series SynPhase™ Lantern was placed in a 1 dram glass vial. A solution of 1:1 trifluoroacetic acid/dichloromethane (0.5 ml) was added to the vial. The vial was capped, and mildly agitated on an orbital shaker (100 rpm) for 2 h. The cleavage solution was transferred to a fresh vial, and an additional 0.5 ml 1:1 trifluoroacetic acid/dichloromethane was added to the lantern. The vial was again capped, and mildly agitated on an orbital shaker (100 rpm) for 2 h. The second cleavage solution was added to the first, and the lantern was rinsed with dichloromethane. The rinse was added to the cleavage solutions, and solvent was evaporated to yield the dipeptide as the trifluoroacetic acid salt of the α-amine.

Scheme 7

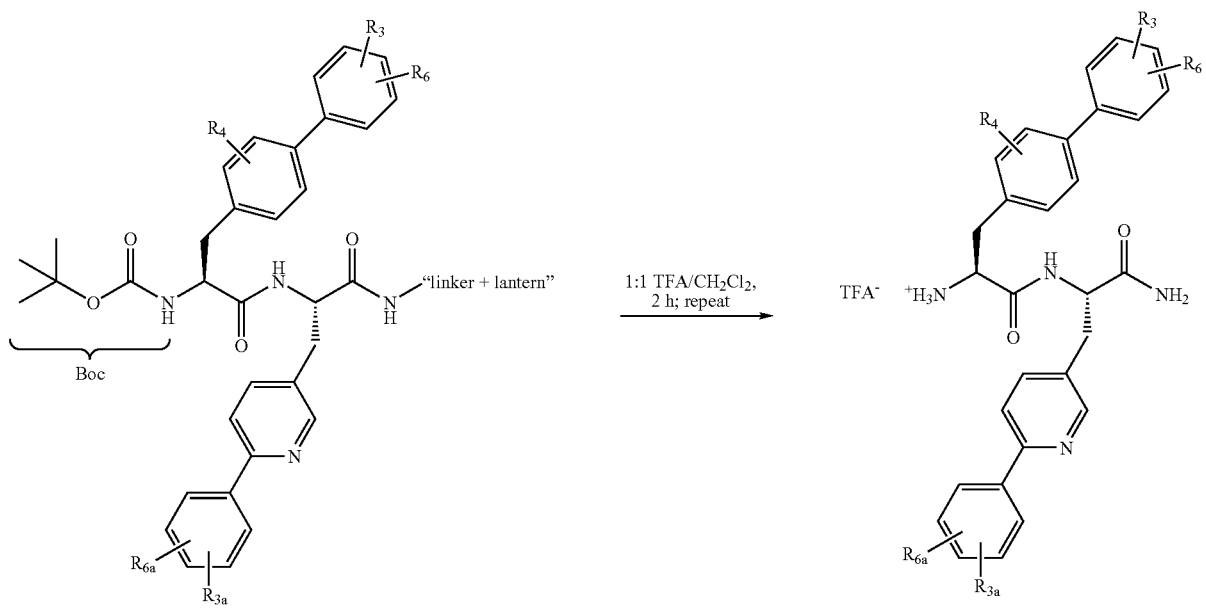

$R_3$, $R_4$, $R_6$, $R_{3a}$, and $R_{6a}$ are represented by the side chains described in Formulas IIa and IVa.

b. Procedure B (Fmoc-Protected Dipeptides; Scheme 8)

The Fmoc-protected dipeptide was cleaved from the SynPhase™ Lantern as described above in Procedure A. The lanterns were rinsed with dichloromethane, and solvent was evaporated from the combined rinse/cleavage solutions. To the resulting residue (in a 1 dram vial) was added 0.40 ml 8:2 dimethylformamide/piperidine (vol:vol). The vial was capped and allowed to react for 45 min. The remaining solvent was evaporated off, and the resulting product was purified by HPLC, using a C-18 column and $CH_3CN/H_2O/TFA$ solvent system to yield (after evaporation of solvent) the dipeptide as the trifluoroacetic acid salt of the α-amine.

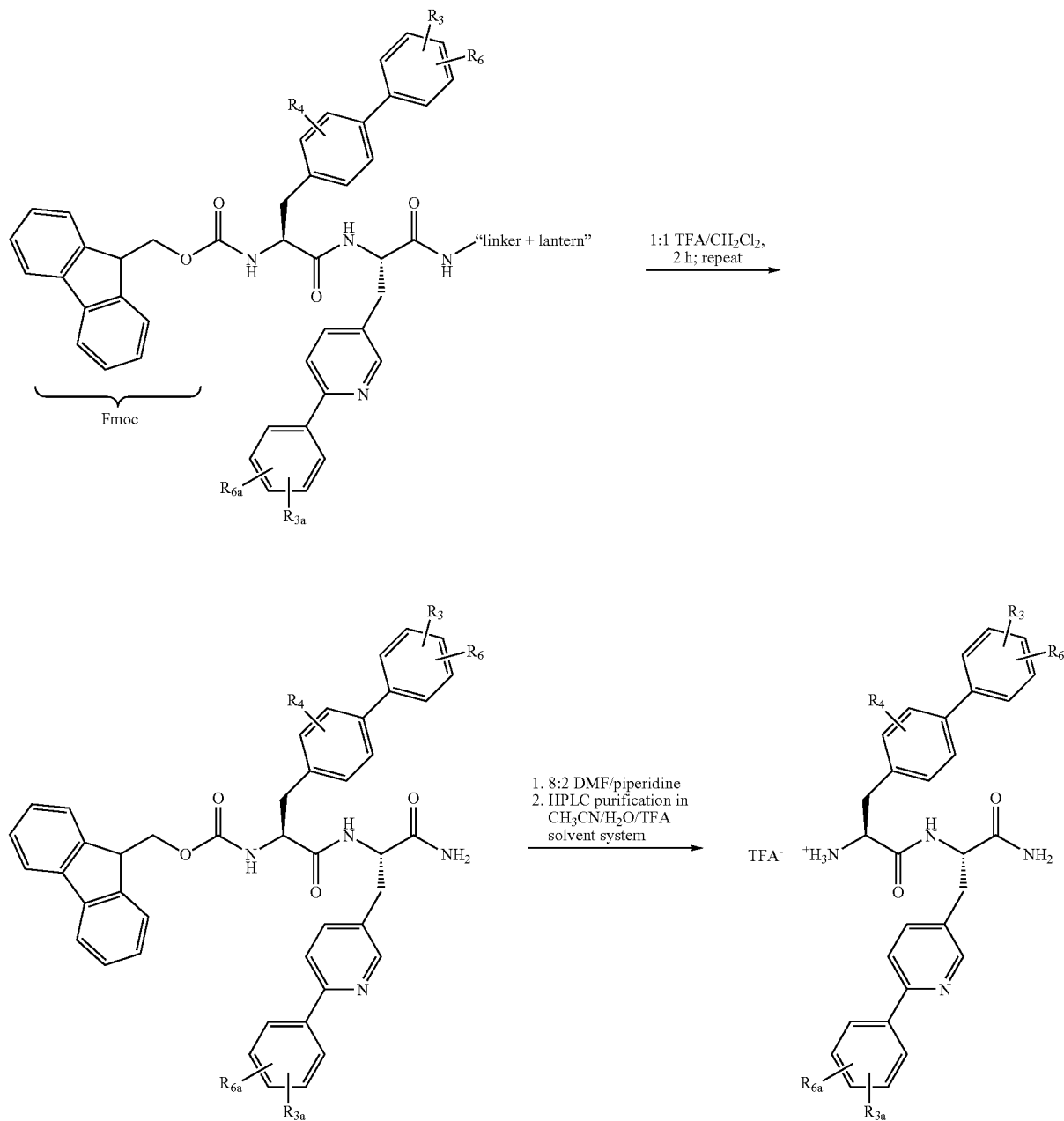

$R_3$, $R_4$, $R_6$, $R_{3a}$, and $R_{6a}$ are represented by the side chains described in Formulas II and IVa.

2. Procedure for Solid Phase Synthesis of Side Chain Protected 9-mer Peptide C-Terminal Carboxylic Acid (Scheme 9).

A solution of Fmoc-(L)-Ser(tBu)-OH (5 eq.), 0.5 M HOAt/DMF (5 eq.) and DIC (5 eq.) in NMP (5 mL) was vortexed with (L)-Asp(OtBu)-2-chloro chlorotrityl resin (3.0 g, 2.16 mmol) for 18 hrs at RT. After several washes with NMP, the Fmoc group was removed by treatment with 1.5 M piperidine/DMF twice (5 min and 10 min). These coupling and deprotection steps were repeated seven times to assemble the desired sequence, except that 1.1 eq. and 1.5 eq. of Fmoc-α-Me-Phe(2-R-6-R")—OH and Boc-(L)-His(Trt)-OH were used, respectively, for their couplings, and that HATU/HOAt and DIEA (4 eq.) were used for coupling Fmoc-Thr(tBu)-OH onto (S)-α-Me-Phe(2-R-6-R")-peptidyl-resin.

Upon assembly completion, the peptidyl-resin was washed with DCM and then the protected 9-mer peptide C-terminal carboxylic acid was released from the resin by treatment with DCM/AcOH/TFE (8:1:1, v:v:v) for 1 hr at RT. The resin was filtered off and the filtrate was evaporated to dryness, redissolved in AcCN/water (2:1) and lyophilized twice, to yield 2.777 g of 81% pure product, which was used in the subsequent fragment coupling step with no further purification.

Scheme 9

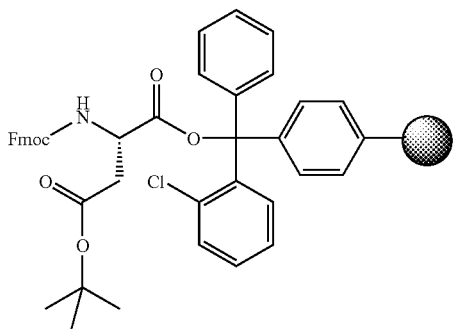

i) Piperidine/DMF (Removal of Fmoc)
ii) Fmoc-AA/DIC/HOAt/NMP/DMF (4–5 eq.)
iii) Repeat the above steps 2 times, changing the Fmoc-AA as required
iv) Piperidine/DMF
v) Fmoc-(S)-α-Me-Phe(2-R-6-R″)-OH, DIC/HOAt/NMP/DMF (1.1 eq.)
vi) Piperidine/DMF
vii) Fmoc-Thr(tBu)-OH/HATU/DIEA/HOAt/NMP/DMF (4 eq.)
viii) Piperidine/DMF
ix) Fmoc-Gly-OH/DIC/HOAt/NMP/DMF (4 eq.)
x) Repeat steps viii-ix 2 times changing the Fmoc-AA as needed
xi) Boc-His(Trt)-OH/DIC/HOAt/NMP/DMF (1.5 eq.)
xii) DCM/HOAc/TFE (8:1:1, v:v:v)
vi) Speed-vac/Lyophilize

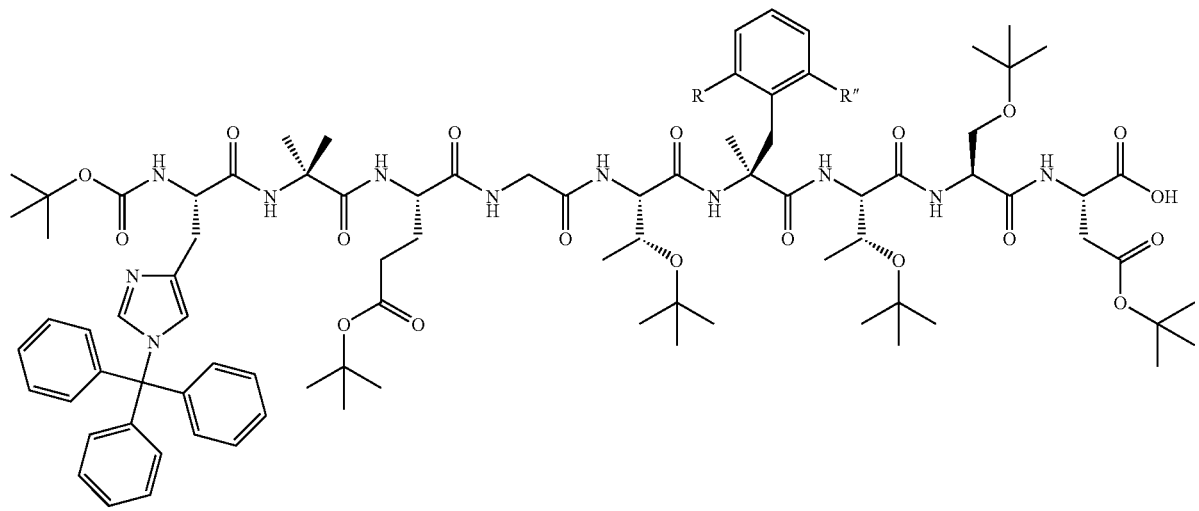

3. Procedure for Solution Phase Fragment Coupling Reaction.

These reactions were performed both in a single-compound format in 1 dram vials, and in a parallel array of compounds in a 2 ml 96-well plate. The following description (shown in Scheme 10) applies to the single-compound case, but is entirely analogous to the reactions performed in the 96-well plate.

The TFA-salt of the dipeptide (0.01 mmol) was dissolved in 0.25 ml THF containing 0.5% N,N-diisopropylethylamine in a 1.5 ml glass vial. Macroporous carbonate resin (MP-carbonate, 0.03 mmol, Argonaut Technologies) was added to the vial. The vial was capped and agitated for 2 h at room temperature. The solution was filtered, and excess solvent was removed by evaporation.

A solution of 0.15 ml of 9:1 chloroform/N,N-dimethylformamide containing the side chain protected 9-mer peptide C-terminal carboxylic acid (0.008 mmol) and N-hydroxybenzotriazole (HOBt, 0.008 mmol) was added to the vial containing the dipeptide amine. Diisopropylcarbodiimide (DIC, 0.08 mmol) was added in a solution of 0.05 ml 9:1 chloroform/N,N-dimethylformamide. The vial was capped, and the reaction was stirred on an orbital shaker at room temperature for 16 h. Remaining solvent was evaporated from the vial.

The 11-mer peptide side chains and N-terminal α-amine were deprotected with 0.40 ml 97.5:2.5 trifluoroacetic acid/triisopropylsilane (TFA/TIS) for 1 h. The remaining solvent was evaporated away, and the 11-mer peptide products were then purified by HPLC, using a $CH_3CN/H_2O$/TFA solvent system, and triggering effluent collection by the detection of desired product mass.

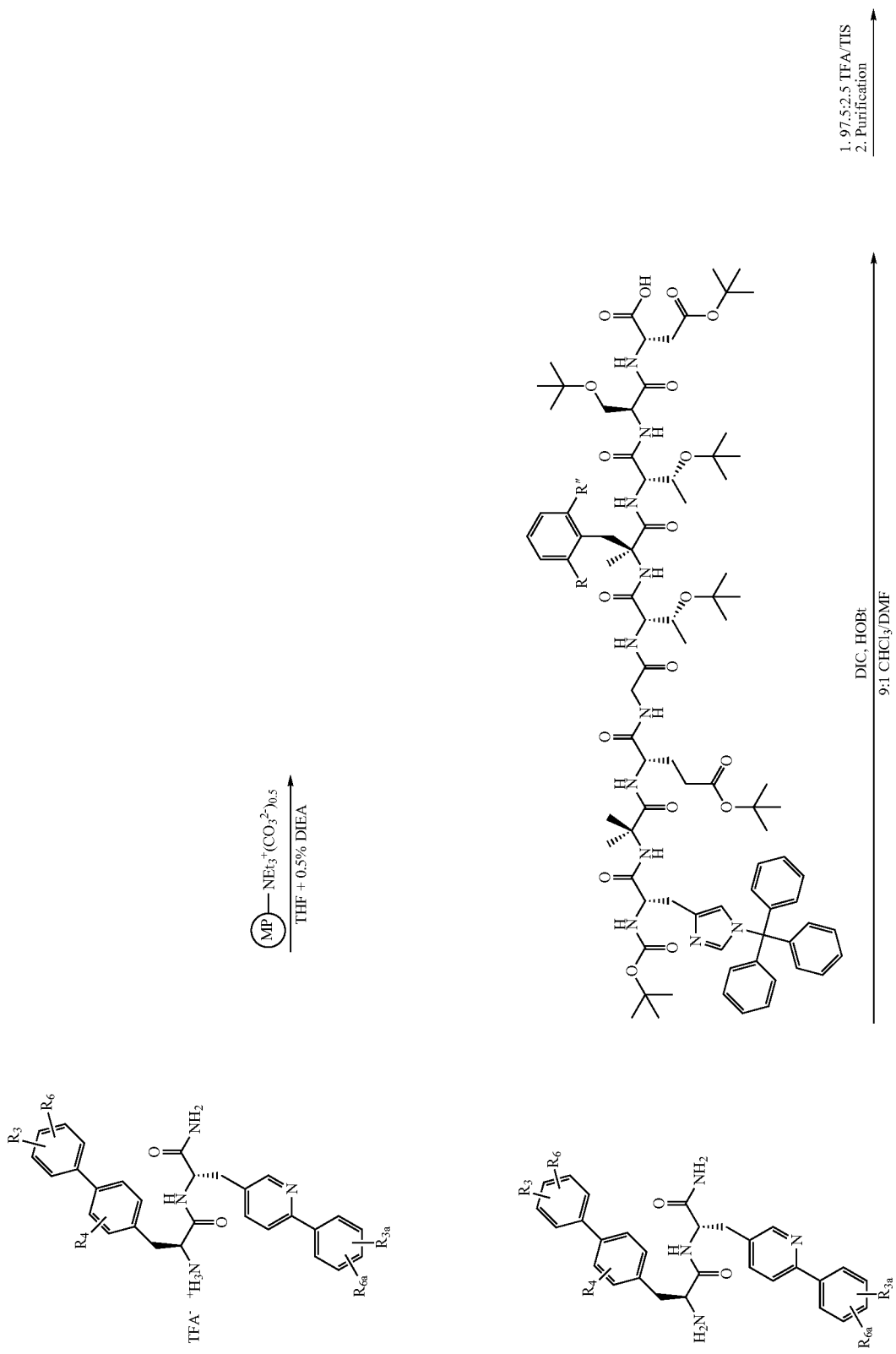
Scheme 10

-continued
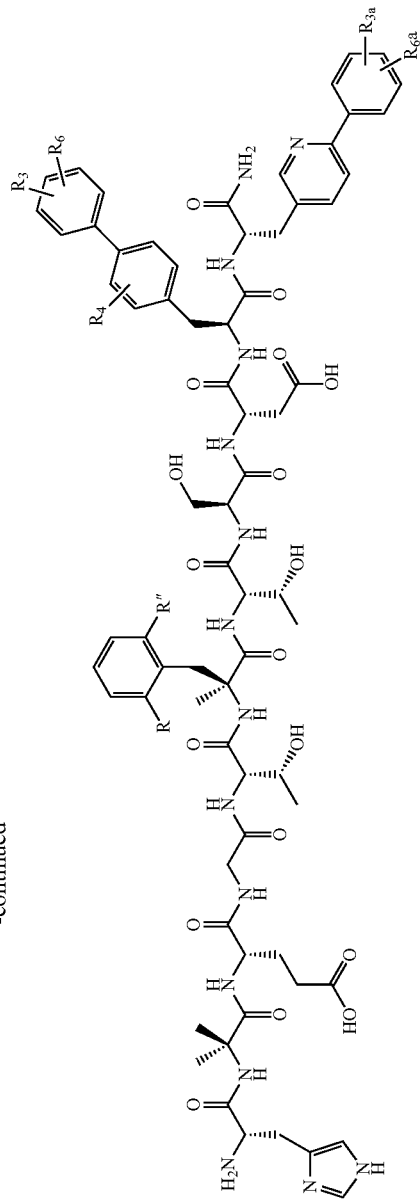
R, R" = H, or F
$R_3$, $R_4$, $R_6$, $R_{3a}$ and $R_{6a}$ are represented by the side chains described in Formulas II and IVa.

B. Approach B: Synthesis of Fmoc-Amino Acids Analogs Represented by Formulas II and IVa Using Suzuki Coupling in Solution.

The below examples illustrate the synthesis of several Fmoc-amino acids analogs represented by Formulas II and IVa, which were then utilized for the solid phase synthesis of 11-mers and other peptide analogs as described in Example 1.

EXAMPLE 10

Synthesis of Fmoc-(S)-2'-ethyl-4'-methoxy-biphenylalanine [Fmoc-(S)-Bip(2'-Et-4'-OMe)]

The following Scheme 11 describes the synthesis of Fmoc-(S)-2'-ethyl-4'-methoxy-biphenylalanine.

Scheme 11

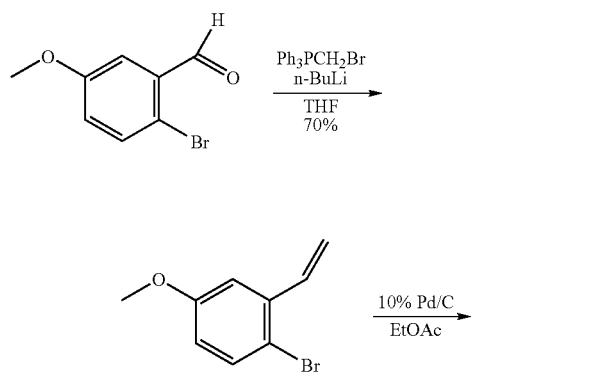

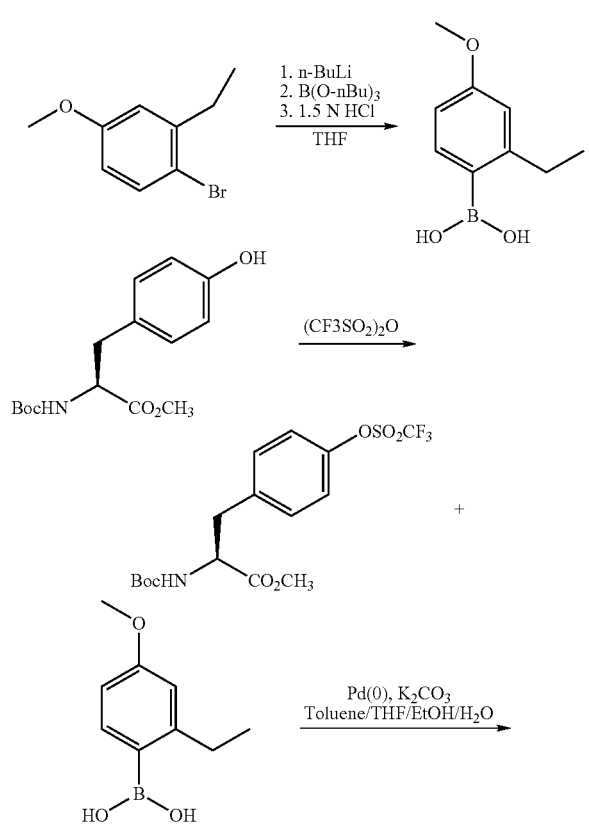

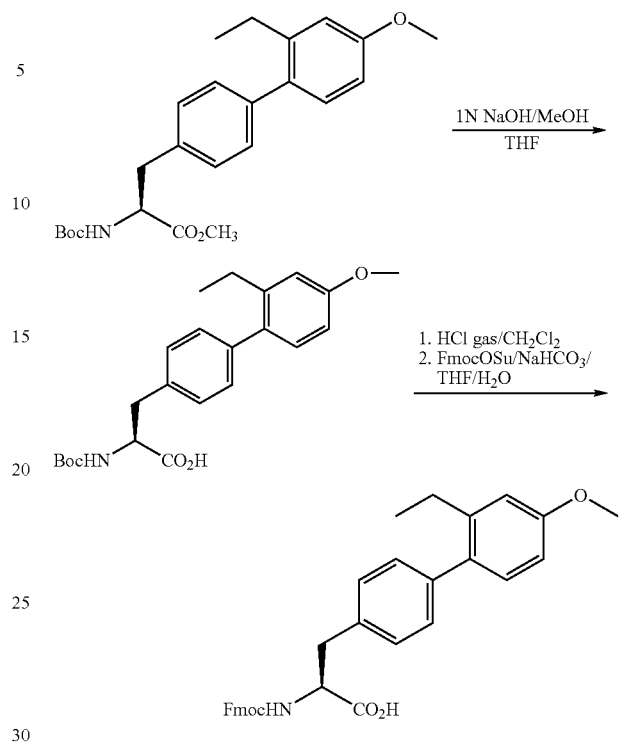

1. Boc-L-Tyrosine-O-triflate.

To a solution of 25 g (85 mmol) of Boc-L-tyrosine methyl ester, and 36.25 g (339 mmol, 4 eq.) of 2,6-lutidine in 200 mL of dry DCM, kept at −40° C. under $N_2$, was added slowly 47.74 mg (169.5 mmol, 2 eq.) of triflic anhydride in DCM (100 ml) over 30 minutes. The solution was stirred at −40° C. for an additional 2 hours. HPLC analysis indicated that the reaction was complete. The reaction was quenched by addition of 20 mL of water. The layers were separated, and the organic layer was washed with 3×200 ml of 1N HCl, 200 ml of saturated Na2CO3, 200 ml of water and 200 mL of brine. The organic layer was dried over magnesium sulfate, filtered and dried in vacuo to give the crude product as a red oil. It was subjected to silica gel flash chromatography (300 g silica gel, 0 to 50% EtOAc in hexanes gradient). The product-containing fractions were concentrated in vacuo to give the desired compound (27 g, 75% yield) as a white solid.

2. 2-Ethyl-4-Methoxy-Phenylboronic Acid.

a. Method A.

A suspension of methyl triphenylphosphoniumbromide (199.5 g, 0.465 mol) in dry THF (800 ml) was purged for 10 min. and cooled to 10° C. n-Butyl lithium (169 ml, 0.465 mol, 2.75 M solution) was added slowly over 30 min. and stirred for 1 hr. 2-Bromo-5-methoxy benzaldehyde (100 g, 0.465 mol) in dry THF (300 ml) was added slowly over a period of 30 min. After the addition, the reaction mixture was stirred for 1 hr. Petroleum ether (2 L) was added and the reaction mixture was stirred for an additional 30 min. The reaction mixture was filtered over a silica gel pad. The pad was washed with diethyl ether. The combined organic washes were concentrated below 30° C. and the crude product was purified by 60-120 silica gel chromatography using 100% pet ether as eluent. Yield: 92 g, 90%, as pale yellow liquid.

2,2'-Bipyridyl (24.3 g, 0.15 mol) and 2-bromo-5-methoxystyrene (65 g, 0.31 mol) in ethyl acetate (650 ml) were cooled to 0° C. The solution was purged and 10% palladium on carbon (16.25 g, 25%) was added under a stream of nitrogen. The reaction mixture was stirred under 2 kg pressure in a Parr shaker for 3 days under hydrogen. The reaction progress was monitored by HPLC. The reaction mixture was filtered through Celite and the filtrate was washed with 5% solution of potassium bisulfate, dried over sodium sulfate and concentrated below 30° C. Yield: 60 g, 91%, as pale yellow liquid.

A solution of 4-bromo-3-ethyl anisole (94 g, 0.437 mol) in THF (900 ml) was cooled to −78° C. n-Butyl lithium (249 ml, 0.55 mol) was added dropwise at the same temperature. Stirring was continued for 1 hr at −78° C. Tri-n-butyl borate (177 ml, 0.655 mol) was added slowly at −78° C. The cooling bath was removed, the reaction mixture was allowed to warm to 0° C. and was quenched with 1.5 N hydrochloric acid at 0° C. The organic layer was separated. The aqueous layer was extracted with ethylacetate and the combined organic layers were washed with brine and concentrated. The residue obtained was stirred in pet-ether for 30 min. The solid obtained was filtered and dried under vacuum. Yield: 65 g, 82%, as a white solid.

b. Method B (see Scheme 12).

To a mixture of 3-Ethylphenol (50 g, 0.4 mol, 98% pure, Fluka) and $K_2CO_3$ (283 g, 2.05 mol) in dry acetone (500 ml) was added methyliodide (290 g, 2.05 mol). The reaction mixture was transferred to an autoclave and refluxed at 70° C. overnight. The reaction mixture was filtered through a Celite pad. The pad was washed with acetone and the combined filtrate and washes were concentrated. The product was dissolved in DCM, filtered and evaporated to dryness. Yield: 50 g, 90%, as a brown liquid.

3-Ethylanisole (50 g, 0.3676 mol) and N-bromosuccinimide (72 g, 0.4 mol) in acetonitrile (1 L) were stirred for 8 hr under dark at RT. The reaction mixture was concentrated below 40° C. and the residue obtained was redissolved in $CCl_4$ and filtered. The filtrate was concentrated and the product was purified by fractional distillation. Yield: 35 g, 43%, as pale yellow liquid. The 4-bromo-3-ethyl anisole was converted to the corresponding boronic acid as described in Method A.

For the purpose of reaction scale up, the conversion of 4-bromo-3-ethyl anisole to 2-ethyl-4-methoxy-boronic acid may be accomplished using a Grignard method. Such method involves formation of the Grignard reagent by reaction of 4-bromo-3-ethyl anisole with Mg (1.1 eq.) in THF, followed by reaction of the resulting Grignard intermediate with tri-n-butyl- or trimethylborate as described in Method A.

Scheme 12

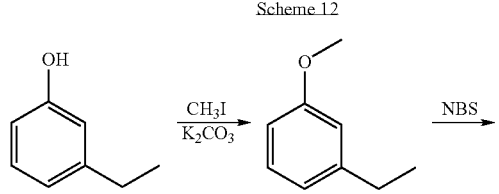

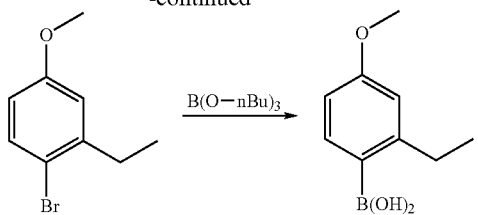

3. Fmoc-(S)-2'-ethyl-4'-methoxy-biphenylalanine.

Boc-L-Tyrosine-O-triflate (81 g, 0.19 mol) in dry toluene (600 ml) was purged for 10 min with nitrogen. $K_2CO_3$ (36 g, 0.26 mol) in 200 ml of water was added followed by 2-Ethyl-4-Methoxy-phenylboronic acid (36 g, 0.2 mol) and the reaction mixture was purged for 10 min using nitrogen. $Pd(PPh_3)_4$ (16.18 g, 0.014 mol), ethanol (200 ml) and THF (400 ml) were added and the reaction mixture was heated to 100° C. with stirring for 4 hr. The reaction mixture was concentrated under vacuum and the residue was dissolved in DCM (1.0 L). The organic layer was washed with 10% sodium hydroxide solution, 15% of citric acid solution, dried over sodium sulfate and concentrated. The crude product was purified by 60-120-mesh silica gel column chromatography with 10% of ethyl acetate in pet-ether. Yield: 50 g, 65%, as a yellow liquid.

To a mixture of the methyl ester of Boc-(S)-2'-ethyl-4'-methoxy-biphenylalanine (60 g, 0.146 mol) in THF (450 ml) and methanol (85 ml) was added sodium hydroxide (24 g, 0.58 mol) in 85 ml of water. The reaction mixture was stirred at RT overnight, concentrated and the residue was dissolved in water (100 ml) and washed with diethyl ether. The aqueous layer was acidified to pH 1 using 20% citric acid and extracted with ethyl acetate. The extract was washed with brine, dried over sodium sulfate and evaporated to dryness. Yield: 55 g, 94%, as colorless liquid.

Boc-(S)-2'-ethyl-4'-methoxy-biphenylalanine (55 g, 0.138 mol) was dissolved in dry DCM (1 lit) and dry HCl gas was purged at RT for 6 hr. The solid product obtained was filtered and dried under vacuum. Yield: 46 g, 100%. To the free amino acid hydrochloride salt (30 g, 0.089 mol) in THF (700 ml) was added $NaHCO_3$ (29 g, 0.358 mol) in water (240 ml). Fmoc-OSu (30 g, 0.089 mol) was added portionwise over a period of 30 min. The reaction mixture was stirred overnight at RT. The THF was removed under vacuum and water (2.0 L) was added. The clear solution was extracted with ether to remove any impurities. The aqueous solution was acidified to pH 1 and extracted with ethyl acetate. The organic layer was washed with water and brine, and was evaporated to dryness. Yield: 37 g, 80%.

EXAMPLE 11

Synthesis of (2S)-2-(((9H-Fluoren-9-yl)methoxy)carbonylamino)-3-(6-o-tolylpyridin-3-yl)propanoic acid hydrochloride [Fmoc(S)-4-(2'-methylphenyl)-3-pyridylalanine hydrochloride]

The following Scheme 13 describes the synthesis of (2S)-2-(((9H-fluoren-9-yl)methoxy)carbonylamino)-3-(6-o-tolylpyridin-3-yl)propanoic acid hydrochloride:

Scheme 13

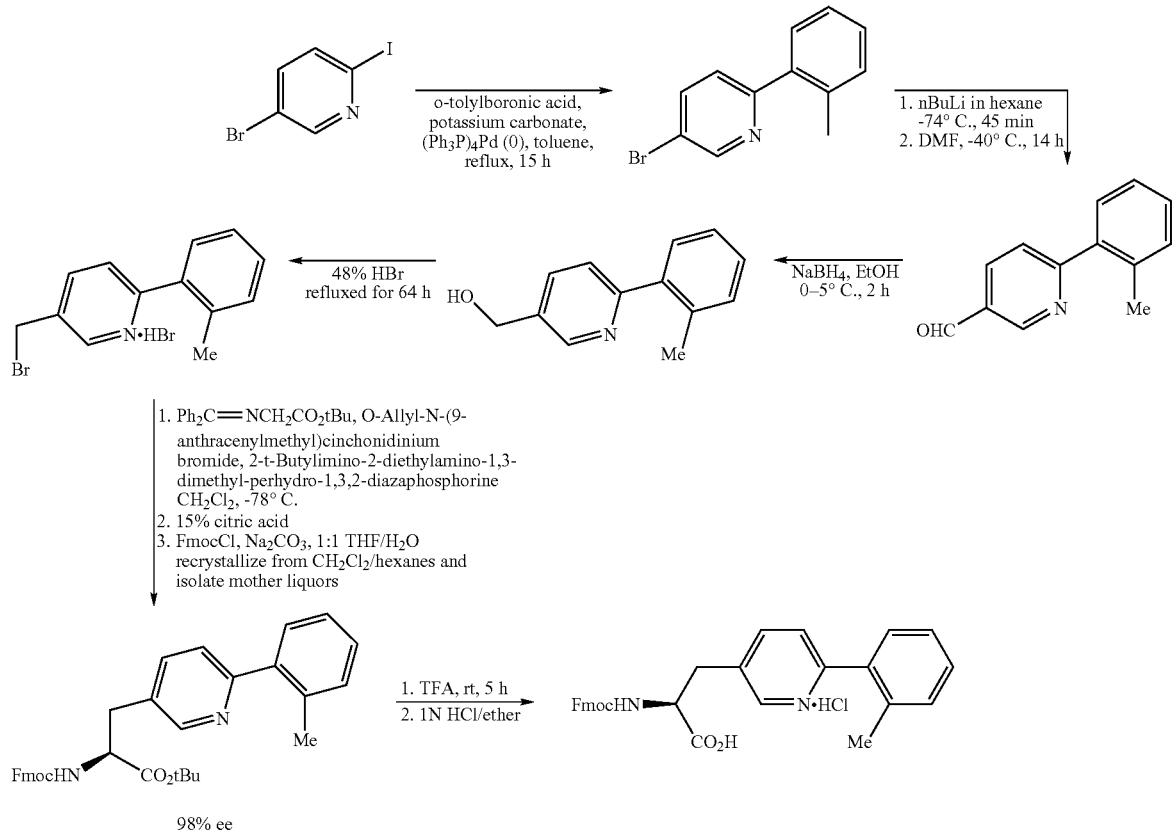

98% ee

1. 5-Bromo-2-o-tolylpyridine

To an argon-purged and evacuated slurry of 910 mg (3.21 mmol) of 5-bromo-2-iodopyridine and 436 mg (3.21 mmol, 1.0 eq.) of 2-o-tolylboronic acid in 8 mL of toluene and 3.2 mL of 2 M aqueous sodium carbonate, was added 36 mg (0.032 mmol, 0.01 eq) of tetrakis(triphenylphosphine) palladium. The reaction mixture was purged and evacuated with argon twice more and then set to reflux under argon for 15 h. The reaction was cooled and partitioned between water and EtOAc. The layers were separated, and the aqueous layer extracted once more with EtOAc. The organic extracts were combined, dried over magnesium sulfate, filtered, concentrated and dried in vacuo to give the crude product as an orange oil. Purification by silica gel chromatography (7:3 $CH_2Cl_2$/hexanes) provided the title compound as a yellow oil, 666 mg, 84% yield.

2. 6-o-Tolylnicotinaldehyde

To a stirred solution of 125 mg of the above compound (0.50 mmol) in THF (2.0 mL) under argon at −74° C. was added 220 μL of nBuLi solution in hexane (2.5 M, 0.55 mmol, 1.1 eq) over 5 min, the temperature not allowed to rise above −71° C. A light green solution formed, which became dark green after 30 min. After 45 min, 49.4 μL (0.61 mmol, 1.2 eq) of DMF was added and the reaction allowed to warm to −40° C. After 14 h, a bright orange solution had formed. The reaction was quenched with 10% citric acid and the mixture stirred rapidly for 20 min at room temperature. The resulting bright yellow solution was extracted twice with EtOAc. The organic extracts were combined, dried over $MgSO_4$, filtered and concentrated to give a yellow oil. The crude mixture thus obtained was purified by silica gel chromatography using ethyl acetate/dichloromethane (1:24) as eluant, (2.5×10 cm column), to give white solid, mp 82-84° C., 90.3 mg, 91% yield.

3. (6-o-Tolylpyridin-3-yl)methanol

To a solution of 1.070 g (5.43 mmol) of 6-o-tolylnicotinaldehyde in 19 mL of ethanol at 0-5° C., was added 287 mg (7.5 mmol, 1.4 eq.) of sodium borohydride. After 2 h, the reaction mixture was quenched with saturated sodium bicarbonate solution and, after 30 min, partitioned between dichloromethane and brine. The organic extract was dried over magnesium sulfate and concentrated to give the indicated product as a colorless oil, 1.08 g, 100% yield.

4. 5-(Bromomethyl)-2-o-tolylpyridine hydrobromide

A solution of 4.49 g (22.5 mmol) of (6-o-tolylpyridin-3-yl)methanol in 75 mL of 48% hydrobromic acid was heated to reflux for 64 h. The reaction mixture was partially cooled and excess hydrobromic acid was removed by vacuum distillation (110° C. @ 2 Torr) until a tan solid residue remained in the flask. Distillation was carried out using a large KOH pellet trap placed between the distillation apparatus and the vacuum pump. The solid residue was slurried in diethyl ether, filtered and dried under a nitrogen stream to give 7.38 g of product, 95% yield.

5. (2S)-tert-butyl 2-(diphenylmethyleneamino)-3-(6-o-tolylpyridin-3-yl)propanoate To a stirred mixture of 800 mg (2.33 mmol) of 5-(bromomethyl)-2-o-tolylpyridine hydrobromide, 689 mg (2.33 mmol, 1.0 equivalent) of tert-butyl 2-(diphenylmethyleneamino)acetate and 141 mg (0.233 mmol, 0.1 equivalent) of O-allyl-N-(9-anthracenylmethyl)cinchonidinium bromide in 14 mL of dichloromethane at −78° C. under argon was added 1.687 mL (5.83 mmol, 2.5 eq) of 2-t-butylimino-2-diethylamino-1,3-dimethyl-perhydro-1,3,2-diazaphosphorine over 5 min. The reaction mixture was stirred at −78° C. for 10 h and then allowed to warm to room temperature in situ. The mixture was directly purified by silica gel chromatography using ethyl acetate/dichloro-methane (1:4) as eluant (5×10 cm column), to give tan oil, 1.10 g, 100% yield.

6. (2S)-tert-Butyl 2-(((9H-fluoren-9-yl)methoxy)carbonylamino)-3-(6-o-tolylpyridin-3-yl)propanoate To a stirred solution of 1.10 g (2.33 mmol) of (2S)-tert-butyl 2-(diphenylmethyleneamino)-3-(6-o-tolylpyridin-3-yl)propanoate in 9 mL of THF at room temperature under argon was added 2.795 g (14.54 mmol, 6.5 equivalents) of citric acid in 9 mL of water. After 20 h, the reaction mixture was diluted with water (5 mL) and washed twice with ether (10 mL). The aqueous phase was then brought to pH 9 with solid sodium carbonate and extracted twice with dichloromethane.

The dichloromethane extracts were combined, dried with sodium sulfate and concentrated. The resulting oil was dissolved in 10 mL of THF and treated with 7.2 mL of 10% sodium carbonate solution and then 703 mg (2.56 mmol, 1.1 equi-valents) of 9-fluorenylmethyloxycarbonylchloride at room temperature. After 14 h, the reaction mixture was extracted twice with dichloromethane, dried with sodium sulfate, filtered, concentrated and purified by chromatography on silica gel using ethyl acetate/dichloromethane (1:19) as eluant (2.5×10 cm column), to give colorless oil, 1.082 g, 91% yield. Recrystallization from 20 mL of 7:1 hexanes/dichloromethane provided a white solid, 287 mg. The mother liquors were concentrated to provide an amorphous white solid, the title compound, 779 mg, 63% yield. Chiral HPLC analysis (4.6×250 mm AD column, 38:1:1 heptane:methanol:ethanol as eluant 1 mL/min flow rate) indicated 98% ee.

7. (2S)-2-(((9H-Fluoren-9-yl)methoxy)carbonylamino)-3-(6-o-tolylpyridin-3-yl)propanoic acid hydrochloride A solution of 1.75 g (3.19 mmol) of (2S)-tert-butyl 2-(((9H-fluoren-9-yl)methoxy)carbonylamino)-3-(6-o-tolylpyridin-3-yl)propanoate in TFA (5.0 mL), protected from the atmosphere by a calcium chloride-filled drying tube was stirred at room temperature for two hours. The reaction mixture was concentrated in vacuo at less than 40° C. and the resulting orange oil was dissolved in 10 mL of ether to which a solution of 5 mL of 1 M HCl/ether was added. The resulting white solid was filtered and washed with ether to give the desired compound as a white powder, 1.65 g, 100% yield.

EXAMPLE 12

Synthesis of (2S)-2-(((9H-Fluoren-9-yl)methoxy)carbonylamino)-4-(6-bromopyridin-3-yl)propanoic acid hydrochloride The following Scheme 14 describes the synthesis of 3-(((9H-fluoren-9-yl)methoxy)carbonylamino)-3-(6-bromopyridin-3-yl)propanoic acid hydrochloride:

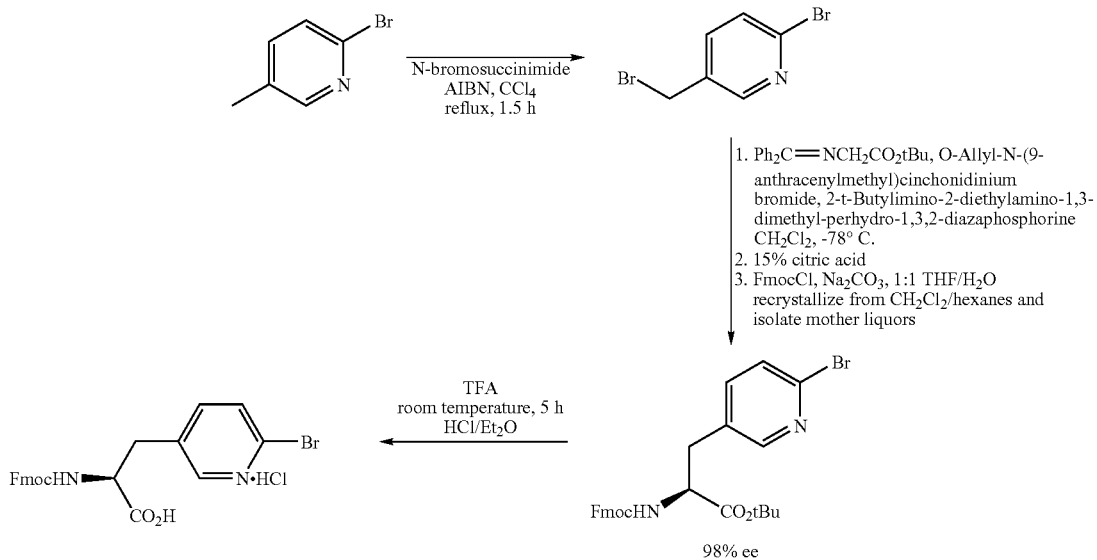

1. 2-Bromo-5-(bromomethyl)pyridine

To a stirred slurry of 10.320 g (60.0 mmol) of 5-methyl-2-bromopyridine and 5.339 g (30.0 mmol, 0.5 eq) of recrystallized N-bromosuccinimide in 150 mL of carbon tetrachloride was added 200 mg of AIBN. The reaction mixture was purged twice with argon and evacuated and set to reflux under argon. After 90 min, the reaction mixture was cooled to room temperature, filtered and the filtrate concentrated to give a yellow oil. Proton NMR indicated that the mixture contains 53% (mol) unreacted 5-methyl-2-bromopyridine, 43% of the title product and 4% of 2-bromo-5-(dibromomethyl)pyridine. The mixture was used immediately without further purification for the following procedure.

2. (S)-tert-Butyl 2-(((9H-fluoren-9-yl)methoxy)carbonylamino)-3-(6-bromopyridin-3-yl)propanoate To a stirred mixture of 2-bromo-5-(bromomethyl)pyridine (nominally 26.4 mmol), 7.798 g (26.4 mmol, 1.0 equivalents) of tert-butyl 2-(diphenyl methyleneamino)acetate and 1.60 g (2.64 mmol, 0.1 equivalent) of O-allyl-N-(9-anthracenylmethyl) cinchonidinium bromide in 100 mL of dichloromethane at −78° C. under argon was added 11.46 mL (39.6 mmol, 1.5 eq) of 2-t-butylimino-2-diethylamino-1,3-dimethyl-perhydro-1,3,2-diazaphosphorine over 5 min. The reaction mixture was stirred at −78° C. for 7 h and then allowed to warm to room temperature in situ. The reaction mixture was then concentrated, redissolved in 75 mL of THF and treated with citric acid (22 g) in 75 mL of water. After stirring vigorously for 7 h, the mixture was extracted twice with ether (75 mL). The organic extracts were combined and washed once with water (25 mL). The aqueous extracts were combined and brought to pH 8 with solid sodium carbonate. The aqueous solution was used without further treatment for the next reaction.

3. (S)-tert-Butyl 2-(((9H-fluoren-9-yl)methoxy)carbonylamino)-3-(6-bromopyridin-3-yl)propanoate The aqueous solution from above was added to a solution of 7.545 g. (27.5 mmol, 1.04 equivalents) of 9-fluorenylmethyloxycarbonylchloride in 75 mL of THF at room temperature. After 14 h, the reaction mixture was extracted twice with ethyl acetate, dried with magnesium sulfate, filtered, concentrated and purified by chromatography on silica gel using ethyl acetate/dichloro-methane (1:24) as eluant (12×25 cm column), to give colorless oil, 7.25 g, 91% yield. Recrystallization from 120 mL of 5:1 hexanes/dichloromethane gave a small amount of a white solid, which was filtered off. The mother liquors were concentrated to provide an amorphous white solid, the title compound, 4.96 g, 62% yield. Chiral HPLC analysis (4.6×250 mm AD column, 38:1:1 heptane: methanol:ethanol as eluant 1 mL/min flow rate) indicated 97.2% ee.

4. 2-(((9H-Fluoren-9-yl)methoxy)carbonylamino)-3-(6-bromopyridin-3-yl)propanoic acid hydrochloride A solution of 1.02 g (1.95 mmol) of (2S)-tert-butyl 2-(((9H-fluoren-9-yl)methoxy)carbonylamino)-3-(6-bromopyridin-3-yl)propanoate in TFA (3.0 mL), protected from the atmosphere by a calcium chloride-filled drying tube was stirred at room temperature for two hours. The reaction mixture was concentrated in vacuo at less than 35° C. and the resulting orange oil was dissolved in 3 mL of dichloromethane to which a solution of 6 mL of 1 M HCl/ether was added. The resulting white solid was filtered and washed with ether to give the title compound as a white powder, 845 mg, 86% yield.

EXAMPLE 13

Synthesis of (2S) 2-(((9H-Fluoren-9-yl)methoxy)carbonylamino)-3-(6-(2-ethylphenyl)pyridin-3-yl)propanoic acid hydrochloride [Fmoc-(S)-4-(2'-ethylphenyl)-3-pyridylalanine]

The following Scheme 15 describes the synthesis of (2S)-2-(((9H-fluoren-9-yl)methoxy)carbonylamino)-3-(6-(2-ethylphenyl)pyridine-3-yl)propanoic acid hydrochloride:

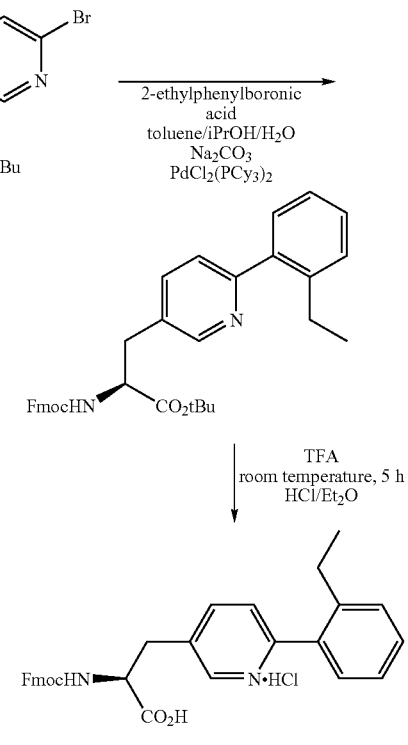

Scheme 15

1. ((S)-tert-Butyl 2-(((9H-fluoren-9-yl)methoxy)carbonylamino)-3-(6-(2-ethylphenyl)pyridine-3-yl)propanoate To a stirred slurry of 1.75 g (3.35 mmol) of (S)-tert-butyl 2-(((9H-fluoren-9-yl)methoxy)carbonylamino)-3-(6-bromo-pyridin-3-yl)propanoate and 1.005 g (6.70 mmol, 2 eq.) of 2-ethylphenylboronic acid in 50 mL of 1:1 isopropanol/toluene was added 25.0 mL of 2 M aqueous sodium carbonate solution. The reaction mixture was purged twice with argon and evacuated and then 124 mg (0.167 mmol, 0.05 equivalents) of bis(tricyclohexylphosphine)palladium (II) chloride was added and the mixture was again purged with argon and evacuated. The rapidly stirred mixture was heated at 80° C. under argon. After 20 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (1:9) as eluant (5×15 cm column), gave the desired compound as a colorless oil, 1.25 g, 77% yield.

2. (2S) 2-(((9H-Fluoren-9-yl)methoxy)carbonylamino)-3-(6-(2-ethylphenyl)pyridine-3-yl)propanoic acid hydrochloride A solution of 1.53 g (2.79 mmol) of (2S)-tert-butyl 2-(((9H-fluoren-9-yl)methoxy)carbonylamino)-4-(6-(2-ethylphenyl)pyridine-3-yl)propanoate in TFA (5.0 mL), protected from the atmosphere by a calcium chloride-filled drying tube was stirred at room temperature for two hours. The reaction mixture was concentrated in vacuo at less than 35° C. and the resulting orange oil was dissolved in ether to which a solution of 6 mL of 1 M HCl/ether was added. The resulting white solid was filtered and washed with ether to give the desired product as a white powder, 1.38 g, 93% yield.

EXAMPLE 14

Synthesis of (2S) 2-(((9H-Fluoren-9-yl)methoxy)carbonylamino)-3-(6-(2-ethyl-4-methoxy)phenyl)pyridin-3-yl)propanoic acid hydrochloride [Fmoc-(S)-4-[(2'-ethyl-4'-methoxy)phenyl]-3-pyridylalanine]

The following Scheme 16 describes the synthesis of (2S)-2-(((9H-fluoren-9-yl)methoxy)carbonylamino)-3-(6-(2-ethyl-4-methoxy)phenyl)pyridine-3-yl)propanoic acid hydrochloride:

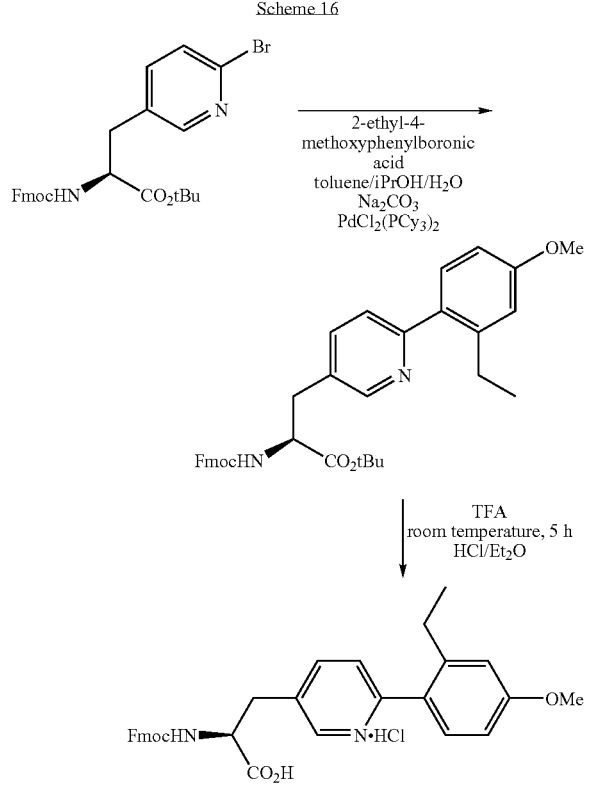

1. (S)-tert-Butyl 2-(((9H-fluoren-9-yl)methoxy)carbonylamino)-3-(6-(2-ethyl-4-methoxyphenyl)pyridine-3-yl)propanoate To a stirred slurry of 613 mg (1.17 mmol) of (S)-tert-butyl 2-(((9H-fluoren-9-yl)methoxy)carbonylamino)-3-(6-bromopyridin-3-yl)propanoate and 422 mg (2.34 mmol, 2 eq.) of 2-ethylphenylboronic acid in 20 mL of 1:1 isopropanol/toluene was added 10.0 mL of 2 M aqueous sodium carbonate solution. The reaction mixture was purged twice with argon and evacuated and then 43.2 mg (0.059 mmol, 0.05 equivalents) of bis(tricyclohexylphosphine)palladium (II) chloride was added and the mixture was again purged with argon and evacuated. The rapidly stirred mixture was heated at 80° C. under argon. After 9 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (3:17) as eluant (5×15 cm column), gave the expected compound as a colorless oil, 401 mg, 59% yield.

2. (2S)2-(((9H-Fluoren-9-yl)methoxy)carbonylamino)-3-(6-(2-ethyl-4-methoxyphenyl)pyridine-3-yl)propanoic acid hydrochloride:

A solution of 401 mg (0.69 mmol) of (2S)-tert-butyl 2-(((9H-fluoren-9-yl)methoxy)carbonylamino)-3-(6-(2-ethyl-4-methoxyphenyl)pyridine-3-yl)propanoate in TFA (2.0 mL), protected from the atmosphere by a calcium chloride-filled drying tube was stirred at room temperature for two hours. The reaction mixture was concentrated in vacuo at less than 30° C. and the resulting orange oil was dissolved in ether to which a solution of 2 mL of 1 M HCl/ether was added. The resulting white solid was filtered and washed with ether to give the desired product as a white powder, 336 mg, 84% yield.

EXAMPLE 15

Alternative synthesis of (S)-tert-Butyl 2-(((9H-fluoren-9-yl)methoxy)carbonylamino)-3-(6-(2-methylphenyl)pyridin-3-yl)propanoate [Fmoc-(S)-4-(2'-methylphenyl)-3-pyridylalanine tert-Butyl ester]

The following Scheme 17 describes the alternate synthesis of (S)-tert-Butyl 2-(((9H-fluoren-9-yl)methoxy)carbonylamino)-3-(6-(2-methylphenyl)pyridin-3-yl)propanoate:

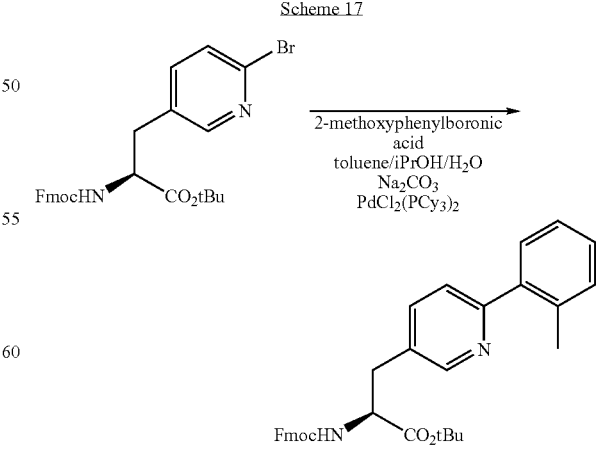

1. (S)-tert-Butyl 2-(((9H-fluoren-9-yl)methoxy)carbonylamino)-3-(6-(2-methylphenyl)pyridin-3-yl)propanoate: To a stirred slurry of 1.75 g (3.35 mmol) of (S)-tert-butyl 2-(((9H-fluoren-9-yl)methoxy)carbonylamino)-3-(6-bromo-pyridin-3-yl)propanoate and 913 mg (6.70 mmol, 2 eq.) of 2-methylphenylboronic acid in 50 mL of 1:1 isopropanol/toluene was added 25.0 mL of 2 M aqueous sodium carbonate solution. The reaction mixture was purged twice with argon and evacuated and then 124 mg (0.167 mmol, 0.05 equivalents) of bis(tricyclohexylphosphine)palladium (II) chloride was added and the mixture again purged with argon and evacuated.

The rapidly stirred mixture was set to heating at 80° C. under argon. After 20 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (1:9) as eluant (5×15 cm column), gave the desired compound as a colorless oil, 1.81 g, 90% yield.

EXAMPLE 16

The following Scheme 18 describes the general synthesis of analogs of (2S)-2-(((9H-fluoren-9-yl)methoxy)carbonylamino)-3-(6-phenyl)pyridin-3-yl)propanoate.

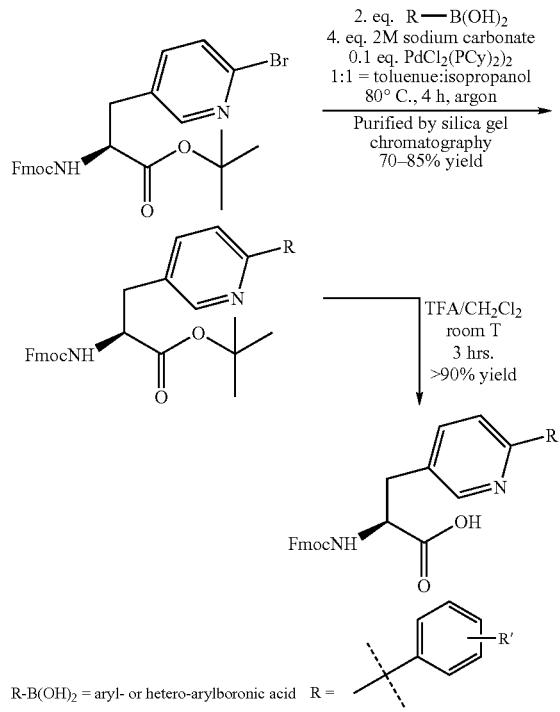

Scheme 18

R-B(OH)₂ = aryl- or hetero-arylboronic acid 1. (2S)-tert-Butyl 2-(((9H-fluoren-9-yl)methoxy) carbonylamino)-3-[6-(3-Chloro-4-fluoro)phenyl) pyridin-3-yl)]propanoate To a round bottom flask was added 300 mg Fmoc-L-bromo-3-pyridylalanine (0.573 mmol), 200 mg 3-chloro-4-fluorophenylboronic acid (1.145 mmol, 2 eq.), 1.145 mL 2M sodium carbonate solution (2.29 mmol, 4 eq.), 5 mL toluene, 5 mL isopropylnol and 42 mg PdCl2(PCy)3)2 (0.0573 mmol, 0.1 eq.). The reaction solution was purged with argon before it was brought to 80° C. for 5 hrs. The reaction was cooled to room temperature and diluted with 50 mL EtOAc. The solution was washed with water (30 mL) and brine (20 mL), dried over magnesium sulfate, filtered and concentrated. The crude oil was subjected to silica gel chromatography (12 gm silica gel, 0-40% EtOAc/Hexanes gradient) to give 245 mg of the desired compound (75% yield) as an oil.

2. (2S)-2-(((9H-fluoren-9-yl)methoxy)carbonylamino)-3-(6-[(3-chloro-4-fluoro)phenyl)pyridin-3-yl)propanoic acid To a solution of (2S)-tert-butyl 2-(((9H-fluoren-9-yl)methoxy)carbonylamino)-3-(6-[(3-chloro-4-fluoro)phenyl)pyridin-3-yl)propanoate (240 mg, 0.429 mmol) and 3 mL dichloromethane was added TFA (3 mL). The reaction was stirred at room temperature for 5 hrs. The solvent was evaporated to dryness and the residue was subjected to prep-HPLC (methanol-water gradient, 0.1% TFA). Concentration of the fractions containing the product yielded 200 mg (93% yield) of the desired compound as the TFA salt.

EXAMPLE 17

Synthesis of a Peptide of SEQ ID NO:1

The desired dipeptidyl resin containing (S)-4-(2'-Methylphenyl)-3-pyridylalanine as the $Xaa_{11}$ amino acid and (S)-(2'-Ethyl-4'-Methoxy)biphenylalanine as the $Xaa_{10}$ amino acid was prepared as described in Example 1. Peptide chain elongation was then completed utilizing the coupling protocols described in Example 1 for amino acids $Xaa_1$-$Xaa_9$. The resulting peptidyl-resin was dried and treated with 2 mL of TFA/TIS/water (96:2:2) for 1.5 hrs. The resin was filtered off and washed with TFA (1×1 ml). The combined filtrates were added to diethyl ether (30 mL), briefly vortexed and then held at −15° C. for 1 hour. The precipitated solid was collected by centrifugation and dried in a speed-vac. The crude product was purified by preparative HPLC as follows: the crude peptide was dissolved in 1 mL of 0.1 M sodium bicarbonate, 2 mL of water and 1 mL of acetonitrile. The peptide was loaded onto a YMC column (SH-343-10P), 250×20 mm I.D., containing ODS-A 10 μm packing material. The column was equipped with a guard column, YMC (G-340-10P), 50×20 mm I.D., containing ODS 10 μm packing. The peptide was eluted with a gradient of 0.1% TFA/MeCN in 0.1% TFA/water, 20% to 45% over 50 minutes, at a flow rate of 15 ml/min. The appropriate fractions collected were pooled and lyophilized to give a 98.6% pure peptide with a HPLC retention time of 14.4 minutes under the following conditions: gradient, 10% to 70% solvent B in A over 20 minutes at 1 mL/min. Solvent A: 0.1% TFA in water, Solvent B: 0.1% TFA in acetonitrile. Column: YMC ODS-A 100×4.6 mm, 3 μm particle size, 12 nm pore size. Mass spectroscopy: ESI $(M+H)^+$=1528.9 and $(M+2H)/2$=765.3.

Synthesis of a Peptide of SEQ ID NO:58

A sample of the $Xaa_4$-$X_{aa11}$ peptidyl-resin (0.067 mmole) described above was vortexed with a solution of Fmoc-L-Glu(OtBu)-OH (5 eq.), residue $Xaa_3$, and 0.5M HOAt (5 eq.) in DMF, pre-vortexed for 5 minutes, and DIC (5 eq.) for 18 hours. The resin was drained, washed with DMF (4×3 mL).

The resin bound peptide (0.034 mmole) was deprotected and coupled with Fmoc-[(S)-α-Me-Pro]-OH (5 eq.) as described previously for residue $X_{aa3}$ to afford the resin bound Fmoc-$[X_{aa2}—X_{aa11}]$-peptide.

The resin (0.017 mmole) was deprotected and coupled with Boc-L-His(Trt)-OH (5eq.) as described for residue $X_{aa2}$. The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated to yield 39 mg of crude peptide product as an oily solid. This was purified by preparative HPLC using a gradient of 0.1% TFA/AcCN in 0.1% TFA/water, from 5% to 65% over 20 min. The fractions containing pure product were pooled and lyophilized, to yield 5.4 mg (18.9% recovery) of 92% pure polypeptide of SEQ ID NO:58; HPLC retention time, 5.65 min, under the following conditions: gradient, from 5-80% 0.1% TFA/MeCN in 0.1% TFA/water over 10 min, flow rate 2.5 mL/min; column: YMC S5 ODS (4.6×50 mm); ESI: $(M+H)^+$=1554.8 amu.

Synthesis of a Peptide of SEQ ID NO:59

A sample of the Fmoc-$[X_{aa3}$-$X_{aa11}]$-peptidyl-Sieber resin (0.015 mmole), described in the previous synthesis, was vortexed with a solution of Fmoc-[N-methyl-(D)-Ala]-OH (5 eq.) and 0.5M HOAt (5 eq.) in DMF, pre-vortexed for 5 minutes, and DIG (5 eq.) for 4 hours. The resin was drained and washed with DMF (4×3 mL). The Fmoc group was removed by treating with 20% piperidine in DMF (3 mL) for 5 and 15 minutes. The resin was washed with DMF (8×3 mL) and then coupled with Boc-L-His(Trt)-OH (5 eq.) as described in the previous synthesis. The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated. The resulting oily solid was dissolved in (1:1) acetonitrile/water (2 mL) and purified by preparative HPLC using a gradient used of 0.1% TFA/MeCN in 0.1% TFA/water, from 5% to 65% over 20 min. The fractions containing pure product were pooled and lyophilized, to yield 5.2 mg (18.5% recovery) 99% of pure polypeptide of SEQ ID NO:59; HPLC retention time, 5.65 min, under the following conditions: gradient, from 5-80% 0.1% TFA/MeCN in 0.1% TFA/water over 10 min, flow rate 2.5 mL/min; column: YMC S5 ODS (4.6×50 mm); ESI: $(M+H)^+$=1528.9 amu.

Synthesis of a Peptide of SEQ ID NO:60

A sample of Fmoc-deprotected $[X_{aa10}—X_{aa11}]$-dipeptidyl-Sieber resin (0.05 mmol), prepared as described previously, was subjected to 9 additional coupling cycles using the FastMoc™ protocol of an Applied Biosystems 433A Peptide Synthesizer as described in Example 3. The Fmoc-protected dipeptidyl-resin (0.05 mmol) was placed into a vessel of appropriate size on the instrument, washed 6 times with NMP and deprotected using two treatments with 20% piperidine/NMP (2 and 8 min. each). One additional monitored deprotection step was performed until the conditions of the monitoring option were satisfied. The total deprotection time was 10-12 min. The deprotected dipeptidyl-resin was washed 6 times with NMP and then coupled with the next amino acid. The procedure is illustrated by the example used in the next step.

Fmoc-L-Asp(OtBu)-OH was coupled next using the following method: Fmoc-L -Asp(OtBu)-OH (1 mmol, 20 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP and the coupling protocol was repeated. This was subjected to 5 additional deprotection/coupling cycles as described above in order to complete the assembly of the desired $X_{aa4}$-$X_{aa11}$ sequence. The Fmoc -amino acids sequentially coupled were: Fmoc-(L)-His(Trt)-OH, Fmoc-(L) -Thr(tBu)-OH, Fmoc-(S)-2-fluoro-α-Me-Phe-OH, Fmoc-(L)-Thr(tBu)-OH and Fmoc-Gly-OH. Finally, the peptidyl-resin was washed 6 times with NMP and DCM. The Emoc-protected dipeptidyl-resin (0.025 mmole) was added to a ACT 396 multiple peptide synthesizer in a slurry of N,N -dimethylformamide/dichloromethane (55:45). The resin was washed 2 times with DMF and deprotected using two treatments with 1.5 M piperidine/DMF as described in Example 1. Fmoc-L-Glu(OtBu)-OH (4.0 eq.) was activated by subsequent addition of 0.5 M HOAt in DMF (4.0 eq.) and DIG (4.0 eq.), transferred to the reaction vessel manually and allowed to couple for 2 hrs. The resin was rinsed with NMP (4×0.5 mL) with vortexing for 1 min. After deprotection of the Fmoc group as described for the previous coupling, Fmoc -[(S)-α-Me-Pro]-OH was coupled as follows: Fmoc-[(S)-α-Me-Pro]-OH (2.4 eq.) was activated by subsequent addition of 0.5 M HOAt in DMF (2.4 eq.), diluted with NMP (0.12 mL), and of DIC (2.4 eq.). The solution was transferred to the reaction vessel manually and allowed to couple for 18 hrs. The resin was rinsed with NMP. After deprotection of the Fmoc group, Fmoc-(L)-His(Trt)-OH was coupled by adding manually a solution of the amino acid (4 eq.) in 0.5 M HOAt in DMF (4 eq.), diluted with NMP (0.2 mL), and DIC (4 eq.) to the reaction vessel. The coupling reaction was allowed to couple for 18 hrs. The resin was rinsed with NMP. The Fmoc group was removed as described for the previous coupling. The TFA cleavage/deprotection of the peptide was performed as described in Example 1. This was purified by preparative HPLC using a gradient of 0.1% TFN/MeCN in 0.1% TFA/water, from 10% to 60% over 20 min. The fractions containing a pure product were pooled and lyophilized, to yield 21.7 mg (42% recovery) of 94% pure polypeptide of SEQ ID NO:60; HPLC retention time, 4.88 min, under the following conditions: gradient, from 5-80% 0.1% TFA/MeCN in 0.1% TFA/water over 10 min, flow rate 2.5 mL/min; column: YMC S5 ODS (4.6×50 mm); ESI: $(M+H)^+$=1604.9 amu.

Synthesis of a Peptide of SEQ ID NO:73

A sample of the Fmoc-deprotected $[X_{aa2}$-$X_{aa11}]$-peptidyl-Sieber resin (0.017 mmole), described in the previous synthesis, was vortexed with a solution of des -amino-His(Trt)-OH (5 eq) and HATU (5 eq.) in 0.5 HOAt in DMF (5 eq.), and a solution of 2M DIEA in NMP (5 eq.) for 18 hours. The resin was drained and washed with DMF (6×2 mL) and DCM (3×2 mL). The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated. The resulting oily solid (32 mg) was dissolved in (1:1) acetonitrile/water (2 mL) and purified by preparative HPLC using a gradient of 0.1% TFA/MeCN in 0.1% TFA/water, from 5% to 65% over 20 min. The fractions containing pure product were pooled and lyophilized, to yield 7.4 mg (24.6% recovery) of 99% pure SEQ ID NO:73; HPLC retention time, 6.01 min, under the following conditions: gradient, from 5-80% 0.1% TFA/

MeCN in 0.1% TFA/water over 10 min, flow rate 2.5 mL/min; column: YMC S5 ODS (4.6×50 mm); ESI: (M+H)$^+$=1539.8 amu.

Synthesis of a Peptide of SEQ ID NO:61

A sample of Fmoc-deprotected [X$_{aa2}$-X$_{aa11}$]-dipeptidyl-Sieber resin (0.05 mmol), prepared as described previously, was subjected to 9 additional coupling cycles using the Fast-Moc™ protocol of an Applied Biosystems 433A Peptide Synthesizer as described in Example 3. The Fmoc-protected dipeptidyl-resin (0.05 mmol) was placed into a vessel of appropriate size on the instrument, washed 6 times with NMP and deprotected using two treatments with 20% piperidine/NMP (2 and 8 min. each). One additional monitored deprotection step was performed until the conditions of the monitoring option were satisfied. The total deprotection time was 10-12 min. The deprotected dipeptidyl-resin was washed 6 times with NMP and then coupled with the next amino acid. The procedure is illustrated by the example used in the next step.

Fmoc-L-Asp(OtBu)-OH was coupled next using the following method: Fmoc-L -Asp(OtBu)-OH (1 mmol, 20 eq.) was dissolved in 2 mL of NMP and activated by subsequent addition of 0.45 M HBTU/HOBt in DMF (2.2 mL) and 2 M DIA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP and the coupling protocol was repeated. This was subjected to 5 additional deprotection/coupling cycles as described above in order to complete the assembly of the desired X$_{aa4}$-X$_{aa11}$ sequence. The Fmoc -amino acids sequentially coupled were: Fmoc-(L)-His(Trt)-OH, Fmoc-(L) -Thr(tBu)-OH, Fmoc-(S)-2-fluoro-α-Me-Phe-OH, Fmoc-(L)-Thr(tBu)-OH and Fmoc-Gly-OH. Finally, the peptidyl-resin was washed 6 times with NMP and DCM. The Fmoc-protected dipeptidyl-resin (0.025 mmole) was added to a ACT 396 multiple peptide synthesizer in a slurry of N,N -dimethylformamide/dichloromethane (55: 45). The resin was washed 2 times with DMF and deprotected using two treatments with 1.5 M piperidine/DMF as described in Example 1. Fmoc-L-Glu(OtBu)-OH (4.0 eq.) was activated by subsequent addition of 0.5 M HOAt in DMF (4.0 eq.) and DIC (4.0 eq.), transferred to the reaction vessel manually and allowed to couple for 2 hrs. The resin was rinsed with NMP (4×0.5 mL) with vortexing for 1 min. After deprotection of the Fmoc group as described for the previous coupling, Fmoc -[(S)-α-Me-Pro]-OH was coupled as follows: Fmoc-[(S)-α-Me-Pro]-OH (2.4 eq.) was activated by subsequent addition of 0.5 M HOAt in DMF (2.4 eq.), diluted with NMP (0.12 mL), and of DIC (2.4 eq.). The solution was transferred to the reaction vessel manually and allowed to couple for 18 hrs. The resin was rinsed with NMP. After deprotection of the Fmoc group, Fmoc-(L)-His(Trt)-OH was coupled by adding manually a solution of the amino acid (4 eq.) in 0.5 M HOAt in DMF (4 eq.), diluted with NMP (0.2 mL), and DIC (4 eq.) to the reaction vessel. The coupling reaction was allowed to couple for 18 hrs. The resin was rinsed with NMP. The Fmoc group was removed as described for the previous coupling. The TFA cleavage/deprotection of the peptide was performed as described in Example 1. This was purified by preparative HPLC using a gradient of 0.1% TFA/MeCN in 0.1% TFA/water, from 10% to 60% over 20 min. The fractions containing a pure product were pooled and lyophilized, to yield 21.7 mg (42% recovery) of 91% pure polypeptide of SEQ ID NO:61, as determined by HPLC; retention time 20.8 minutes, using the following conditions: gradient, 10% to 60% solvent B in A over 25 minutes at 1 mL/min. Solvent A: 0.1% TFA in water, Solvent B: 0.1% TFA in acetonitrile. Column: YMC ODS-A 150×4.6 mm, 3 μm particle size, 12 nm pore size. Mass spectroscopy: ESI (M+H)$^+$=1568.9 and (M+2H)/2=785.2.

EXAMPLE 18

Synthesis of (R,S)-3-(1-(2,4-dinitrophenyl)-imidazol-4-yl)-2-methylpropionic acid [α-Methyl-β-[1-(2, 4-dinitrophenyl)-imidazol-4-yl]propionic acid] [3-(1H-imidazol-4-yl)-2-methylpropionic acid may be Abbreviated as Imp, see "Amino Acid Abbreviations and Structures", below]

1-Tosyl-4(5)-hydroxymethylimidazole

The following procedure was adapted from Agr. Biol. Chem., 38 (5), 1097-1099, 1974. To a solution of Na$_2$CO$_3$ (8.4 g., 0.08 mole) in water (40 mL) was added 4-(hydroxymethyl)imidazole hydrochloride (2.7 g, 0.02 mole). Upon complete dissolution, a solution of p-toluenesulfonyl chloride (4.58 g, 0.024 mole) in ethyl acetate (30 mL) was added dropwise over a 5 minute period. The reaction mixture was allowed to stir for 5 hours. The layers were separated and more ethyl acetate was added (20 mLs). The organic phase was washed with 0.1 M Na$_2$CO$_3$ (2×20 mL), water (1×20 mL) and then saturated NaCl (1×20 mL). The ethyl acetate was treated with 2 g of MgSO$_4$ and 1 g of activated charcoal for 10 minutes. The solids were removed by filtration through a celite pad and the solvent removed on a rotavap. The residue began to crystallize. Fresh ethyl acetate was added (10 mL) and the solution was warmed with a heat gun to redissolve the solids. The product crystallized overnight at room temperature. The crystalline material was collected, washed with ethyl acetate (5 mL) and then ethyl ether (10 mL), and dried in vacuo to a constant weight of 3.59 g.

1-Tosyl-4(5)-acetoxymethylimidazole

1-Tosyl-4(5)-hydroxymethylimidazole (2.52 g, 10 mmole) was dissolved in chloroform (10 ml). To this was added triethylamine (2.02 g, 20 mmole) dropwise at room temperature, followed by dropwise addition of acetic anhydride (1.33 g, 13 mmole) over 15 minutes. The mixture was stirred at room temperature and monitored by LC/MS for four days. The chloroform was removed by reduced pressure and the residue was dissolved in ethyl acetate (60 ml). The organic layer was washed successively with 0.1 M sodium bicarbonate, water and then saturated sodium chloride, all 1×40 ml each. The organic layer was treated with activated charcoal and magnesium sulfate simultaneously and then filtered through a celite pad. The solvent was removed by reduced pressure and the resultant residue was dissolved in warm ethyl acetate (10 ml). To this solution was slowly added 20 ml of diethyl ether. The solution was left to crystallize overnight at room temperature. The crystals were collected, washed with diethyl ether (2×10 ml) and dried in vacuo overnight to yield 1.55 g.

Methyl-α-carbomethoxy-α-methyl-β-4-(1-tosylimidazole)-propionate

The following procedure was adapted from Synthetic Communications, 19(7&8), 1157-1165, 1989. A solution of 1-Tosyl-4(5)-acetoxymethylimidazole (0.3516 g, 1.2 mmole)

and dimethyl methylmalonate (0.1485 g, 1.0 mmole) in acetonitrile (2 ml) was added to a stirred suspension of powdered KOH (0.1694 g, 3.0 mmole) and tetrabutylammonium bromide (0.0496 g, 0.15 mmole) in acetonitrile (1 ml). The reaction was complete after 40 mins, as determined by HPLC analysis. The reaction mixture was poured into ethyl ether (100 ml), filtered through a celite pad and the solvents were removed by evaporation under reduced pressure. The residual oil was dissolved in 30 ml of ethyl acetate and washed with 0.1 M $NaHCO_3$ (1×15 ml), saturated NaCl (1×15 ml) and dried over $MgSO_4$. The solvent was removed under reduced pressure and the resultant oil was left in a desiccator in vacuum for 3 days to yield 0.207 g.

α-Methyl-β-4-imidazole propionic acid

Methyl-α-carbomethoxy-α-methyl-β-4-(1-tosylimidazole)propionate (0.186 g, 0.5 mmole) was dissolved in 2 ml of methanol. To this was added 1.5 ml of 1.0 N NaOH and the reaction was allowed to stir overnight. After purification by preparative HPLC, the product obtained by lyophilization (0.1366 g) was dissolved with 5 ml of 1.0 N NaOH and heated at 100° C. for 2 hours in a 16×100 mm screw-cap tube sealed with a PTFE lined cap, followed by addition of 2 ml of concentrated HCl and heating at 145° C. for 6 hours. The desired decarboxylated product was formed. The entire solution was filtered and loaded onto a YMC G-340-10P ODS 50×20 mm preparative HPLC column. The product was eluted with a gradient of 0% to 60% 0.1% TFA/MeCN in 0.1% TFA/water over 60 minutes. The fractions corresponding to 11 to 13 minutes in the gradient were pooled, frozen and lyophilized to give 32 mg of product.

α-Methyl-β-[1-(2,4-dinitrophenyl)-imidazol-4-yl] propionic acid

To a solution of α-Methyl-β-4-imidazole propionic acid (0.0305 g, 0.114 mmoles) and sodium bicarbonate (0.0617 g, 0.734 mmole) in water (1 mL) (pH 8.04) was added a solution of 2,4-dinitrofluorobenzene (0.0323 g, 0.174 mmole) in MeCN (1.0 mL). The reaction mixture was vortexed overnight. The MeCN was removed under reduced pressure and the residue was redissolved in 2 mL of water, filtered and loaded onto a Phenomenex Luna C18(2) 5 μm 100×21.2 mm preparative HPLC column in two aliquots of 1.5 and 0.5 mL each. The product was eluted with a gradient of 0% to 80% 0.1% TFA/MeCN in 0.1% TFA/water over 40 minutes. The fractions corresponding to 12.5 to 14.5 minutes in the gradient were pooled and dried in a Savant SpeedVac™ overnight. Additional product was recovered by dissolving the water-insoluble crude product in DMSO, followed by preparative HPLC as described above. The combined fractions produced 31 mg of pure product after lyophilization.

EXAMPLE 19

Synthesis of Peptides of SEQ ID NO's:77, 78, 79, and 80

(R,S)-3-(1-(2,4-dinitrophenyl)-imidazol-4-yl)-2-methyl-propionic acid was coupled to the relevant Xaa2-Xaa11-peptidyl-Sieber resin as follows:
To a solution of (R,S)-3-(1-(2,4-dinitrophenyl)-imidazol-4-yl)-2-methylpropionic acid (0.0267 g, 0.083 mmoles), 6-Cl—HOBt (0.0151 g, 0.089 mmoles) and HCTU (0.0360 g, 0.087 mmoles) in 1 mL of NMP/DCM (3:1) was added DIEA (0.0315 g, 0.244 mmole); the solution was briefly vortexed and then added to the relevant Fmoc deprotected Xaa2-Xaa11-peptidyl-Sieber resin prepared as described in Example 19. The coupling was allowed to proceed for 16 hours. The peptidyl-resin was washed with NMP then DCM (3×1.5 mL×1 min) and then treated with 10% acetic anhydride in DCM, 1×2 mL×90 minutes, followed by DCM then DMF washes (3×1.5 mL×1 min). The peptidyl-resin was treated with 10% thiophenol in DMF (1.5 mL) for 1 hr and washed with DMF and DCM (4×1.5 mL×1 min). The peptidyl-resin was then treated with TFA/DCM/TIS (3:1.9:0.1) (1 mL) for 10 min and filtered. The filtrates were collected and gently vortexed for another hr. The TFA mixture was concentrated in a speed-vac to about 0.5 mL and added to 4 mL of MTBE. After 1 hr the precipitated product was collected by centrifugation, washed and then dried to give 0.0841 g of crude product. This was purified by preparative HPLC as follows: the crude peptide was dissolved and injected into a Phenomenex Luna C18(2) (5 μm, 250×30 mm) column and eluted using a linear gradient from 20% to 50% 0.1% TFA/MeCN in 0.1% TFA/water over 40 min at a flow rate of 15 mL/min with effluent UV detection at 217 nm. The fractions containing the desired product pooled and lyophilized to give 26.7 mg of 97.5% pure peptide; HPLC retention time, 21.2 min. under the following conditions: gradient, 10% to 60% solvent B in A over 25 minutes at 1 mL/min. Solvent A: 0.1% TFA in water, Solvent B: 0.1% TFA in MeCN. Column: YMC ODS-A 150×4.6 mm, 3 μm particle size, 12 nm pore size. Mass spectroscopy: ESI $(M+H)^+=1527.9$ and $(M+2H)/2=764.9$.

Preparative chiral HPLC purification of the peptide: The diastereomeric peptide mixture (10 mg) was dissolved in MeCN/MeOH. The solution was loaded onto a Chirobiotic V 2.2×50 cm, 5 μm column and eluted with MeCN/MeOH/N$(CH_2CH_3)_3$/$CH_3COOH$: 65/35/0.5/0.5 at 20 mL/min. Isomer A was collected between 29 and 35 minutes. Isomer B was collected between 36 and 44 min. A second run was made as described above. The fractions containing Isomer A were combined, concentrated to about 5 mL, diluted with water/MeCN (4:1) and the solution was lyophilized. Isomer B was processed in the same manner. The resultant residues were converted to TFA salts by preparative HPLC. Each peptide was injected into a Phenomenex Luna C18(2) 5 μm 100×21.2 mm column and eluted using a linear gradient from 20% to 50% 0.1% TFA/MeCN in 0.1% TFA/water over 40 min. at a flow rate of 10 mL/min with effluent UV detection at 217 nm. The fractions containing the desired product were pooled, frozen and lyophilized to give 6.0 mg 100% pure Isomer A, HPLC retention time 21.28 min. under the following conditions: gradient, 10% to 60% solvent B in A over 25 minutes at 1 mL/min. Solvent A: 0.1% TFA in water, Solvent B: 0.1% TFA in MeCN. Column: YMC ODS-A 150×4.6 mm, 3 μm particle size, 12 nm pore size. Mass spectroscopy: ESI $(M+H)^+=1527.6$ and $(M+2H)/2=764.7$. In a similar manner 4.9 mg of 100% pure peptide Isomer B was obtained; HPLC retention time, 21.3 min. under the following conditions: gradient, 10% to 60% solvent B in A over 25 minutes at 1 mL/min. Solvent A: 0.1% TFA in water, Solvent B: 0.1% TFA in MeCN. Column: YMC ODS-A 150×4.6 mm, 3 μm particle size, 12 nm pore size. Mass spectroscopy: ESI $(M+H)^+=1527.5$ and $(M+2H)/2=764.6$

EXAMPLE 20

Utilizing the synthetic methods described herein the 11-mer peptides set forth in Table I were prepared. $X_{aa1}$-$X_{aa11}$ set forth in Table 3 for each compound refer to the following Formula I:

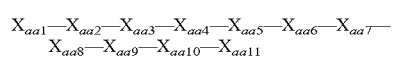

TABLE 3

| SEQ ID NO: | Xaa1 | Xaa2 | Xaa3 | Xaa4 | Xaa5 | Xaa6 | Xaa7 | Xaa8 | Xaa9 | Xaa10 | Xaa11-NH2 |
|---|---|---|---|---|---|---|---|---|---|---|---|
| 1 | H | Aib | E | G | T | L-α-Me-Phe(2-Fluoro) | T | S | D | Bip(2'-Et-4'-OMe) | 4-(2'-Methylphenyl)-3-pyridylalanine-NH2 |
| 2 | H | Aib | E | G | T | L-α-Me-Phe(2,6-di-Fluoro) | T | S | D | Bip(2'-Et-4'-OMe) | 4-(2'-Methylphenyl)-3-pyridylalanine-NH2 |
| 3 | Des-NH2-His | Aib | E | G | T | L-α-Me-Phe(2-Fluoro) | T | S | D | Bip(2'-Et-4'-OMe) | 4-(2'-Methylphenyl)-3-pyridylalanine-NH2 |
| 4 | Des-NH2-His | Aib | E | G | T | L-α-Me-Phe(2,6-di-Fluoro) | T | S | D | Bip(2'-Et-4'-OMe) | 4-(2'-Methylphenyl)-3-pyridylalanine-NH2 |
| 5 | H | Aib | E | G | T | L-α-Me-Phe(2-Fluoro) | T | S | D | Bip(2'-Et-4'-OMe) | 4-(2'-trifluoromethylphenyl)-3-pyridylalanine-NH2 |
| 6 | H | Aib | E | G | T | L-α-Me-Phe(2-Fluoro) | T | S | D | Bip(2'-Et-4'-OMe) | 4-(2'-trifluoromethylphenyl)-3-pyridylalanine-NH2 |
| 7 | H | Aib | E | G | T | L-α-Me-Phe(2-Fluoro) | T | S | D | Bip(2'-Et-4'-OMe) | 4-[(2'-Methyl-5'-fluoro)phenyl)]-3-pyridylalanine-NH2 |
| 8 | H | Aib | E | G | T | L-α-Me-Phe(2-Fluoro) | T | S | D | Bip(2'-Et-4'-OMe) | 4-(4'-methanesulfonylphenyl)-3-pyridylalanine-NH2 |
| 9 | H | Aib | E | G | T | L-α-Me-Phe | T | S | D | Bip(2'-Et-4'-OMe) | 4-(2'-Methylphenyl)-3-pyridylalanine-NH2 |
| 10 | H | Aib | E | G | T | L-α-Me-Phe(2-Fluoro) | T | S | D | Bip(2'-Et-) | 4-(2'-Methylphenyl)-3-pyridylalanine-NH2 |
| 11 | H | Aib | E | G | Nle | L-α-Me-Phe(2-Fluoro) | T | S | D | Bip(2'-Et-4'-OMe) | 4-(2'-Methylphenyl)-3-pyridylalanine-NH2 |
| 12 | H | Aib | E | G | T | L-α-Me-Phe(2,6-di-Fluoro) | T | S | D | Bip(2'-Cl) | 4-(2'-Methylphenyl)-3-pyridylalanine-NH2 |
| 13 | H | Aib | E | G | T | L-α-Me-Phe(2,6-di-Fluoro) | T | S | D | Bip(2',4'-di-OMe) | 4-(2'-Methylphenyl)-3-pyridylalanine-NH2 |
| 15 | H | Aib | E | G | T | L-α-Me-Phe(2,6-di-Fluoro) | T | S | D | Bip(2-Me-3-F) | 4-(2'-Methylphenyl)-3-pyridylalanine-NH2 |
| 16 | H | Aib | E | G | T | L-α-Me-Phe(2-Fluoro) | T | S | D | Bip(2'-F) | 4-(2'-Methylphenyl)-3-pyridylalanine-NH2 |
| 17 | H | Aib | E | G | T | L-α-Me-Phe(2,6-di-Fluoro) | T | S | D | 4-[(2'-Cl-4'-CF3)-3'-pyridyl]-phenylalanine | 4-(2'-Methylphenyl)-3-pyridylalanine-NH2 |
| 18 | H | Aib | E | G | Nva | L-α-Me-Phe(2-Fluoro) | T | S | D | Bip(2'-Et-4'-OMe) | 4-(2'-Methylphenyl)-3-pyridylalanine-NH2 |
| 19 | H | Aib | E | G | T | L-α-Me-Phe(2-Fluoro) | T | S | D | Bip(2'-Et-4'-OMe) | 4-(2'-ethylphenyl)-3-pyridylalanine-NH2 |
| 20 | H | Aib | E | G | T | L-α-Me-Phe(2,6-di-Fluoro) | T | S | D | Bip(2'-Et) | 4-(2'-Ethylphenyl)-3-pyridylalanine-NH2 |
| 21 | H | Aib | E | G | T | L-α-Me-Phe(2,6-di-Fluoro) | T | S | D | Bip(2'-Et-4'-OMe) | 4-(4'-pyridyl)-phenylalanine-NH2 |
| 22 | H | Aib | E | G | T | L-α-Me-Phe(2-Fluoro) | T | S | D | Bip(2'-Et-4'-OMe) | 4-[(2'-Methoxy)-3'-pyridyl)phenylalanine-NH2 |
| 23 | H | Aib | E | G | T | L-α-Me-Phe(2-Fluoro) | T | S | D | Bip(2'-Et-4'-OMe) | 4-phenyl-3-pyridylalanine-NH2 |
| 24 | H | Aib | E | G | T | L-α-Me-Phe(2-Fluoro) | T | S | D | Bip(2'-Et-4'-OMe) | 4-(3',5'-dimethylphenyl)-3-pyridylalanine-NH2 |
| 25 | H | Aib | E | G | T | L-α-Me-Phe(2-Fluoro) | T | S | D | Bip(2'-Et-4'-OMe) | 4-[(3'-chloro-4'-fluoro)phenyl]-3-pyridylalanine-NH2 |
| 26 | H | Aib | E | G | T | L-α-Me-Phe(2-Fluoro) | T | S | D | Bip(2'-Et-4'-OMe) | 4-[(3',4'-dimethoxy)phenyl]-3-pyridylalanine-NH2 |
| 27 | H | Aib | E | G | T | L-α-Me-Phe(2-Fluoro) | T | S | D | Bip(2'-Et-4'-OMe) | 4-[(2'-ethyl-4'-methoxy)phenyl)]-3-pyridylalanine-NH2 |
| 28 | L-β-Imidazolelactyl | Aib | E | G | T | L-α-Me-Phe(2-Fluoro) | T | S | D | Bip(2'-Et-4'-OMe) | 4-(2'-Methylphenyl)-3-pyridylalanine-NH2 |
| 29 | H | Aib | E | G | T | L-α-Me-Phe(2-Fluoro) | T | S | D | Bip(2'-Et-4'-OMe) | 4-(2'-Isopropoxyphenyl)-3-pyridylalanine-NH2 |
| 30 | H | Aib | E | G | T | L-α-Me-Phe(2-Fluoro) | T | S | D | Bip(2'-Et-4'-OMe) | 4-(2'-Methyl, 5'-Fluoro)phenyl)-3-pyridylalanine-NH2 |

TABLE 3-continued

| SEQ ID NO: | Xaa1 | Xaa2 | Xaa3 | Xaa4 | Xaa5 | Xaa6 | Xaa7 | Xaa8 | Xaa9 | Xaa10 | Xaa11-NH2 |
|---|---|---|---|---|---|---|---|---|---|---|---|
| 31 | H | Aib | E | G | T | L-α-Me-Phe(2-Fluoro) | T | S | D | Bip(2'-Et-4'-OMe) | 4-(2'-Isopropoxyphenyl)-3-pyridylalanine-NH2 |
| 32 | H | Aib | E | G | T | L-α-Me-Phe(2-Fluoro) | T | S | D | Bip(2'-Et-4'-OMe) | 4-(4'-Methoxyphenyl)-3-pyridylalanine-NH2 |
| 33 | H | Aib | E | G | T | L-α-Me-Phe(2-Fluoro) | T | S | D | Bip(2'-Et-4'-OMe) | 4-(2'-Methyl, 4'-Fluoro)phenyl)-3-pyridylalanine-NH2 |
| 34 | H | Aib | E | G | T | L-α-Me-Phe(2-Fluoro) | T | S | D | Bip(2'-Et) | 4-(2'-Methylphenyl)-3-pyridylalanine-NH2 |
| 35 | H | Aib | E | G | T | L-α-Me-Phe(2-Fluoro) | T | S | D | Bip(2'-Et-4'-OMe) | 4-(2'-Trifluoromethoxyphenyl)-3-pyridylalanine-NH2 |
| 36 | H | Aib | E | G | T | L-α-Me-Phe(2-Fluoro) | T | S | D | Bip(2'-Et-4'-OMe) | 4-(4'-Trifluoromethoxyphenyl)-3-pyridylalanine-NH2 |
| 37 | H | Aib | E | G | T | L-α-Me-Phe(2-Fluoro) | T | S | D | Bip(2'-Et-4'-OMe) | 4-(2'-Methyl, 4'-Chloro)phenyl)-3-pyridylalanine-NH2 |
| 38 | H | Aib | E | G | T | L-α-Me-Phe(2-Fluoro) | T | S | D | Bip(2'-Me-4'-OMe) | 4-(2'-Methylphenyl)-3-pyridylalanine-NH2 |
| 39 | H | Aib | E | G | T | L-α-Me-Phe(2-Fluoro) | T | S | D | Bip(2'-Et-4'-OMe) | 4-(3'-Trifluoromethylphenyl)-3-pyridylalanine-NH2 |
| 40 | H | Aib | E | G | T | L-α-Me-Phe(2-Fluoro) | T | S | D | Bip(2'-Et-4'-OMe) | 4-(4'-Fluorophenyl)-3-pyridylalanrne-NH2 |
| 41 | H | Aib | E | G | T | L-α-Me-Phe(2-Fluoro) | T | S | D | Bip(2'-Et-4'-OMe) | 4-(2'-Trifluoromethylphenyl)-3-pyridylalanine-NH2 |
| 42 | H | Aib | E | G | T | L-α-Me-Phe(2-Fluoro) | T | S | D | Bip(2'-Et-4'-OMe) | 4-(2'-Chlorophenyl)-3-pyridylalanine-NH2 |
| 43 | H | Aib | E | G | T | L-α-Me-Phe(2-Fluoro) | T | S | D | Bip(2'-Et-4'-OMe) | 4-(3'-Chlorophenyl)-3-pyridylalanine-NH2 |
| 44 | H | Aib | E | G | T | L-α-Me-Phe(2-Fluoro) | T | S | D | Bip(2'-Et-4'-OMe) | 4-(4'-Isopropylphenyl)-3-pyridylalanine-NH2 |
| 45 | H | Aib | E | G | T | L-α-Me-Phe(2-Fluoro) | T | S | D | Bip(2'-Et-4'-OMe) | 4-[(2'-Methyl-4'-methoxy)phenyl]-3-pyridylalanine-NH2 |
| 46 | H | Aib | E | G | T | L-α-Me-Phe(2-Fluoro) | T | S | D | Bip(2'-Et-4'-OMe) | 4-(4'-Trifluoromethylphenyl)-3-pyridylalanine-NH2 |
| 47 | H | Aib | E | G | T | L-α-Me-Phe(2-Fluoro) | T | S | D | Bip(2'-Et-4'-OMe) | 4-(4'-Chlorophenyl)-3-pyridylalanine-NH2 |
| 48 | H | Aib | E | G | T | L-α-Me-Phe(2-Fluoro) | T | S | D | Bip(2'-Et-4'-OMe) | 4-(4'-Pyridyl)-3-pyridylalanine-NH2 |
| 49 | H | Aib | E | G | T | L-α-Me-Phe(2-Fluoro) | T | S | D | Bip(2'-Et-4'-OMe) | 4-(3'-Methoxyphenyl)-3-pyridylalanine-NH2 |
| 50 | H | Aib | E | G | T | L-α-Me-Phe(2-Fluoro) | T | S | D | Bip(2'-Et-4'-OMe) | 4-(6'-Methoxypyridin-3'-yl)-3-pyridylalanine-NH2 |
| 51 | H | Aib | E | G | T | L-α-Me-Phe(2-Fluoro) | T | S | D | Bip(2'-Et-4'-OMe) | 4-(2'-Isopropylphenyl)-3-pyridylalanine-NH2 |
| 52 | H | Aib | E | G | T | L-α-Me-Phe(2-Fluoro) | T | S | D | Bip(2'-Et-4'-OMe) | 4-(2'-Methoxyphenyl)-3-pyridylalanine-NH2 |
| 53 | H | Aib | E | G | T | L-α-Me-Phe(2-Fluoro) | T | S | D | Bip(2'-Et-4'-OMe) | 4-[(3',5'-di-Fluoro-2'-methoxy)phenyl]-3-pyridylalanine-NH2 |
| 54 | H | Aib | E | G | T | L-α-Me-Phe(2-Fluoro) | T | S | D | Bip(2'-Et-4'-OMe) | 4-(3'-methylphenyl)-3-pyridylalanine-NH2 |
| 55 | H | Aib | E | G | T | L-α-Me-Phe(2-Fluoro) | T | S | D | Bip(2'-Et-4'-OMe) | 4-(2'-fluorophenyl)-3-pyridylalanine-NH2 |
| 56 | H | Aib | E | G | T | L-α-Me-Phe(2,6-di-Fluoro) | T | S | D | Bip(2'-Et-4'-OMe) | 4-(2'-fluorophenyl)-3-pyridylalanine-NH2 |
| 57 | H | Aib | E | G | T | L-α-Me-Phe(2,6-di-Fluoro) | T | S | D | Bip(2'-Et-4'-OMe) | 4-(3'-Methoxyphenyl)-3-pyridylalanine-NH2 |
| 58 | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 59 | H | N—Me-(D)-Ala | E | G | T | L-α-Me-Phe(2-Fluoro) | T | S | D | Bip(2'-Et-4'-OMe) | 4-(2'-Methylphenyl)-3-pyridylalanine-NH2 |
| 60 | H | (S)-α-Me-Pro | E | G | T | L-α-Me-Phe(2-Fluoro) | T | H | D | Bip(2'-Et-4'-OMe) | 4-(2'-Methylphenyl)-3-pyridylalanine-NH2 |
| 61 | H | (S)-α- | E | G | T | L-α-Me-Phe(2-Fluoro) | T | S | D | Bip(2'-Et-4'-OMe) | (S)-4-(2'-Methylphenyl)-α-Me-3-pyridylalanine- |

TABLE 3-continued

| SEQ ID NO: | Xaa1 | Xaa2 | Xaa3 | Xaa4 | Xaa5 | Xaa6 | Xaa7 | Xaa8 | Xaa9 | Xaa10 | Xaa11-NH2 |
|---|---|---|---|---|---|---|---|---|---|---|---|
| | | Me-Pro | | | | | | | | | NH2 |
| 62 | H | Aib | E | G | T | L-α-Me-Phe(2-Fluoro) | T | S | D | Bip(2'-Et-4'-OMe) | (S)-4-(2'-Methylphenyl)-α-Me-3-pyridylalanine-NH2 |
| 63 | H | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 64 | H | (S)-α-Me-Pro | E | G | T | L-α-Me-Phe(2,6-di-Fluoro) | T | H | D | Bip(2'-Et-4'-OMe) | 4-(2'-Methylphenyl)-3-pyridylalanine-NH2 |
| 65 | H | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH2 |
| 66 | H | (S)-α-Me-Pro | E | G | T | L-α-Me-Phe(2,6-di-Fluoro) | T | S | D | Bip(2'-Et-4'-OMe) | 4-(3'-Methoxyphenyl)-3-pyridylalanine-NH2 |
| 67 | H | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH2 |
| 68 | H | (S)-α-Me-Pro | E | G | T | L-α-Me-Phe(2,6-di-Fluoro) | T | S | D | Bip(2'-Et-4'-OMe) | 4-(2'-Fluorophenyl)-3-pyridylalanine-NH2 |
| 69 | H | N—Me-(L)-Ala | E | G | T | L-α-Me-Phe(2-Fluoro) | T | S | D | Bip(2'-Et-4'-OMe) | 4-(2'-Methylphenyl)-3-pyridylalanine-NH2 |
| 70 | H | Aib | E | G | T | L-α-Me-Phe(2-Fluoro) | T | S | D | Bip(2'-Et-4'-OMe) | 4-(2'-Methylphenyl)-3,5-pyrimidylalanine-NH2 |
| 71 | H | (S)-α-Me-Pro | D | G | T | L-α-Me-Phe(2-Fluoro) | T | S | D | Bip(2'-Et-4'-OMe) | 4-(2'-Methylphenyl)-3-pyridylalanine-NH2 |
| 72 | H | (S)-α-Me-Pro | E | G | T | L-α-Me-Phe(2-Fluoro) | T | S | D | Bip(2'-Et) | 4-(2'-Ethylphenyl)-3-pyridylalanine-NH2 |
| 73 | Des-NH$_2$-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 74 | Des-NH$_2$-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 75 | Des-NH$_2$-His | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH2 |

TABLE 3-continued

| SEQ ID NO: | Xaa1 | Xaa2 | Xaa3 | Xaa4 | Xaa5 | Xaa6 | Xaa7 | Xaa8 | Xaa9 | Xaa10 | Xaa11-NH2 |
|---|---|---|---|---|---|---|---|---|---|---|---|
| 76 | Des-NH$_2$-His | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH2 |
| 77 | (R)-Imp | Aib | E | G | T | L-α-Me-Phe(2-Fluoro) | T | H | D | Bip(2'-Et-4'-OMe) | 4-(2'-Methylphenyl)-3-pyridylalanine-NH2 |
| 78 | (R)-Imp | Aib | E | G | T | L-α-Me-Phe(2-Fluoro) | T | H | D | Bip(2'-Et-4'-OMe) | 4-(2'-Methylphenyl)-3-pyridylalanine-NH2 |
| 79 | (S)-Imp | Aib | E | G | T | L-α-Me-Phe(2-Fluoro) | T | S | D | Bip(2'-Et-4'-OMe) | 4-(2'-Methylphenyl)-3-pyridylalanine-NH2 |
| 80 | (S)-Imp | Aib | E | G | T | L-α-Me-Phe(2-Fluoro) | T | H | D | Bip(2'-Et-4'-OMe) | 4-(2'-Methylphenyl)-3-pyridylalanine-NH2 |
| 81 | CH$_3$O—CO-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 82 | CH$_3$O—CO-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 83 | CH$_3$O—CO-His | N—Me-(D)-Ala | E | G | T | L-α-Me-Phe(2-Fluoro) | T | S | D | Bip(2'-Et-4'-OMe) | 4-(2'-Methylphenyl)-3-pyridylalanine-NH2 |
| 84 | CH$_3$O—CO-His | N—Me-(D)-Ala | E | G | T | L-α-Me-Phe(2,6-di-Fluoro) | T | S | D | Bip(2'-Et-4'-OMe) | 4-(2'-Methylphenyl)-3-pyridylalanine-NH2 |
| 85 | CH$_3$SO$_2$-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 86 | CH$_3$SO$_2$-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 87 | L-Lactyl-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH2 |
| 88 | L-Lactyl-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH2 |
| 89 | H | Aib | E | G | T | L-α-Me-Phe(2-Fluoro) | T | S | D | Bip(2'-Et-4'-OMe) | 4-(3',5'-di-Me)phenyl-3-pyridylalanine-NH2 |
| 90 | H | Aib | E | G | T | L-α-Me-Phe(2-Fluoro) | T | H | D | Bip(2'-Et-4'-OMe) | 4-(2'-Methylphenyl)-3-pyridylalanine-NH2 |
| 91 | H | D-Ala | E | G | T | L-α-Me-Phe(2-Fluoro) | T | S | D | Bip(2'-Et-4'-OMe) | 4-(2'-Methylphenyl)-3-pyridylalanine-NH2 |
| 92 | H | Aib | H | G | T | L-α-Me-Phe(2-Fluoro) | T | S | D | Bip(2'-Et-4'-OMe) | 4-(2'-Methylphenyl)-3-pyridylalanine-NH2 |
| 93 | | | | | | | T | S | D | Bip | pyridyl alanine |
| 94 | CH3O—CO-His | (S)-α Me-Pro | E | G | T | L-α-Me-Phe(2-Fluoro) | T | H | D | Bip(2'-Et-4'-OMe) | 4-(2'-Methylphenyl)-3-pyridylalanine-NH2 |

Amino Acid Abbreviations and Structures
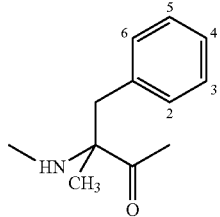
Numbering of the α-methyl-
phenylalanine
(α-Me-Phe) ring carbons
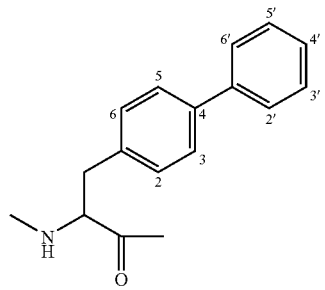
Numbering of the
biphenylalanine
ring carbons
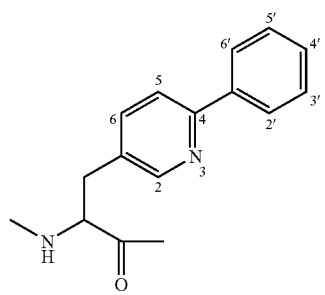
Numbering of the hetero-
biphenylalanine
ring carbons
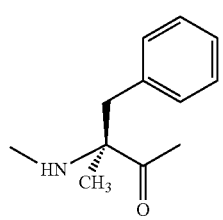 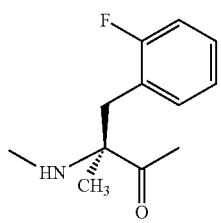
(L)-α-Me-Phe  (L)-α-Me-Phe(2-Fluoro)
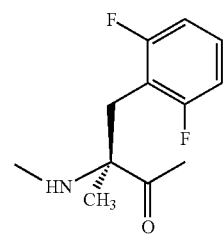
(L)-α-Me-Phe(2,6-di-Fluoro)
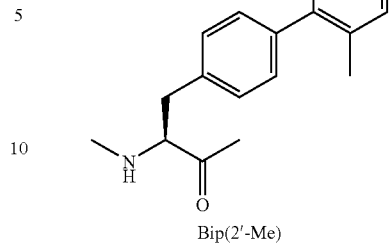
Bip(2'-Me)
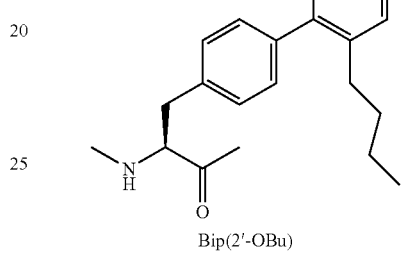
Bip(2'-OBu)
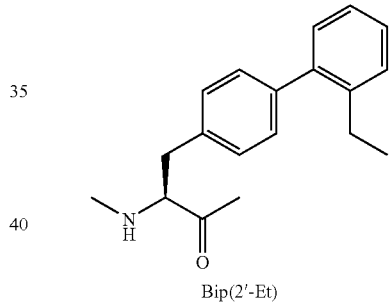
Bip(2'-Et)
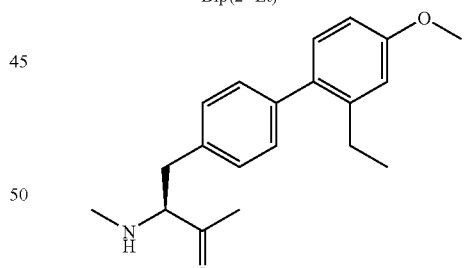
Bip(2'-Et-4'-OMe)
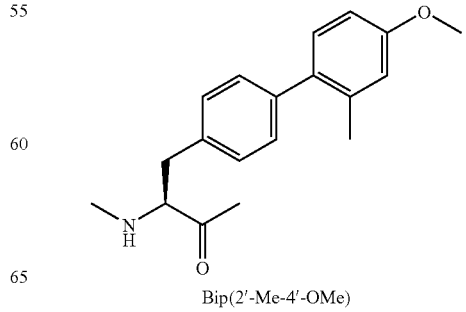
Bip(2'-Me-4'-OMe)

-continued
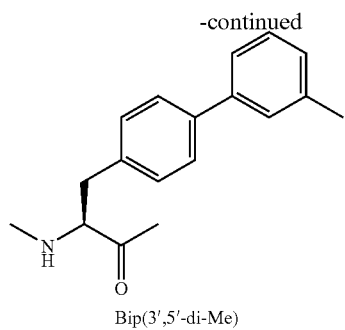
Bip(3',5'-di-Me)
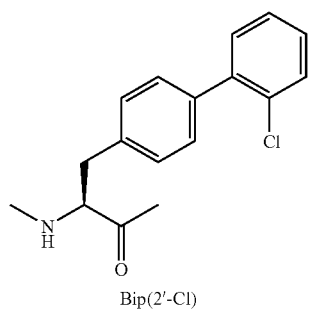
Bip(2'-Cl)
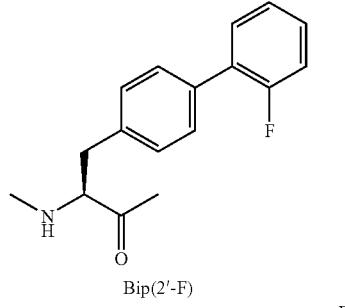
Bip(2'-F)
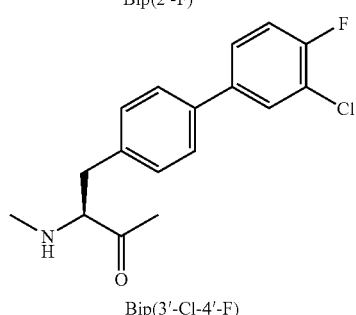
Bip(3'-Cl-4'-F)
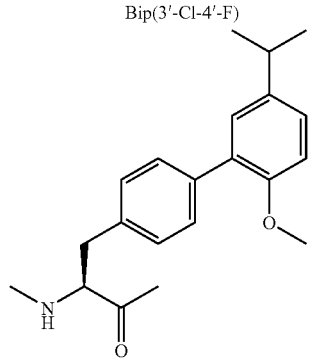
-continued
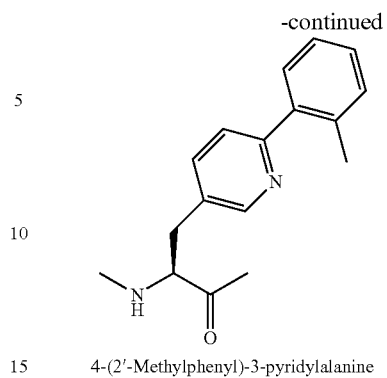
4-(2'-Methylphenyl)-3-pyridylalanine
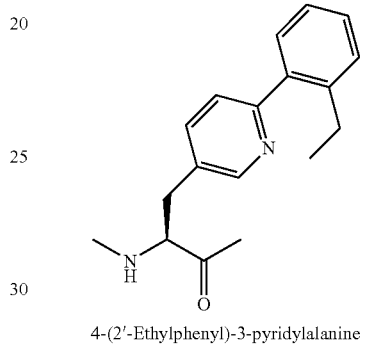
4-(2'-Ethylphenyl)-3-pyridylalanine
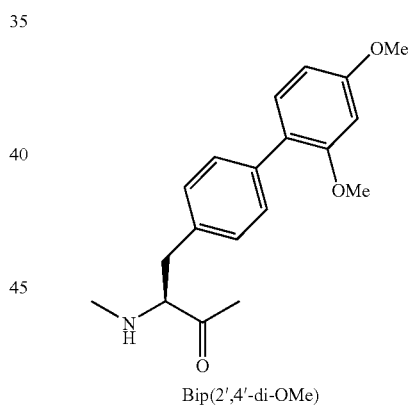
Bip(2',4'-di-OMe)
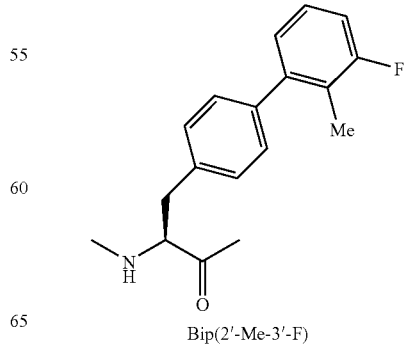
Bip(2'-Me-3'-F)

-continued
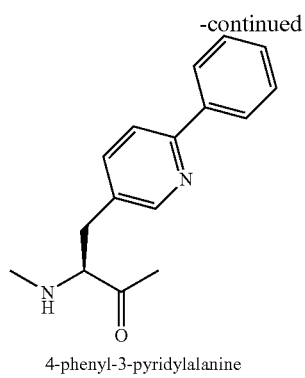
4-phenyl-3-pyridylalanine
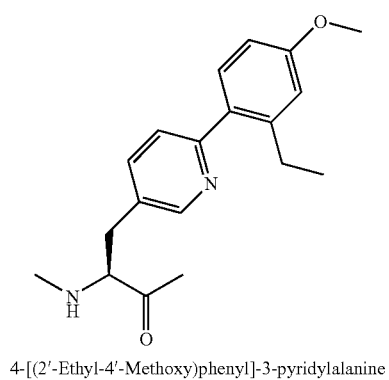
4-[(2'-Ethyl-4'-Methoxy)phenyl]-3-pyridylalanine
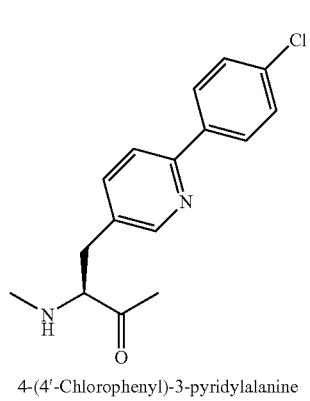
4-(4'-Chlorophenyl)-3-pyridylalanine
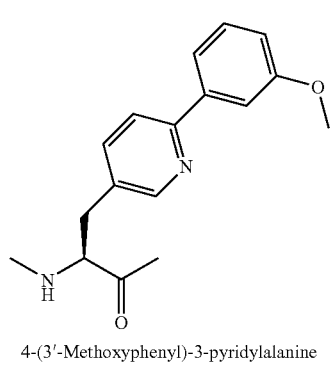
4-(3'-Methoxyphenyl)-3-pyridylalanine
-continued
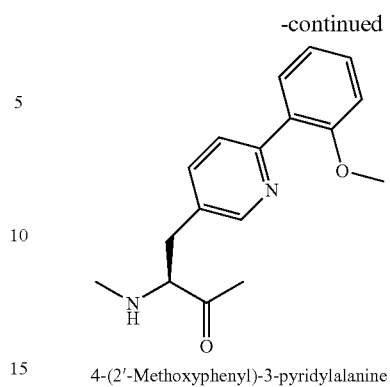
4-(2'-Methoxyphenyl)-3-pyridylalanine
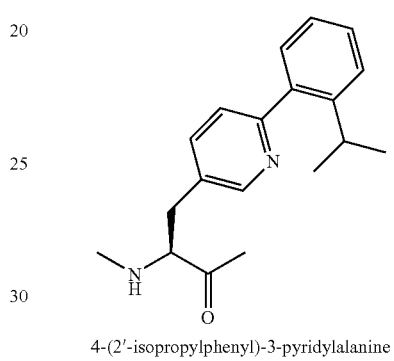
4-(2'-isopropylphenyl)-3-pyridylalanine
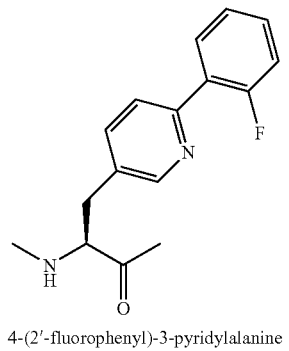
4-(2'-fluorophenyl)-3-pyridylalanine
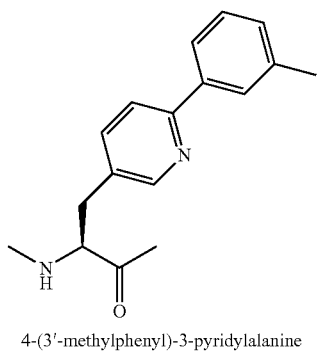
4-(3'-methylphenyl)-3-pyridylalanine -continued
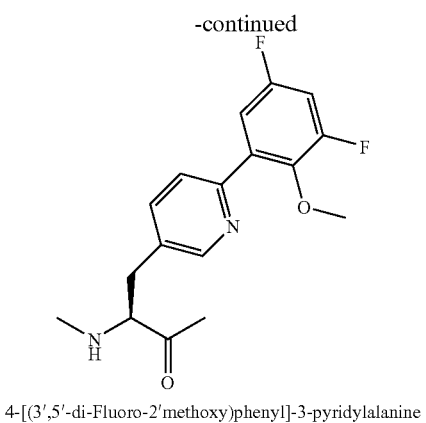
4-[(3′,5′-di-Fluoro-2′methoxy)phenyl]-3-pyridylalanine
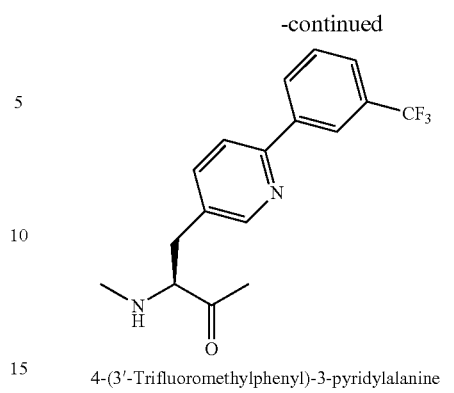
4-(3′-Trifluoromethylphenyl)-3-pyridylalanine
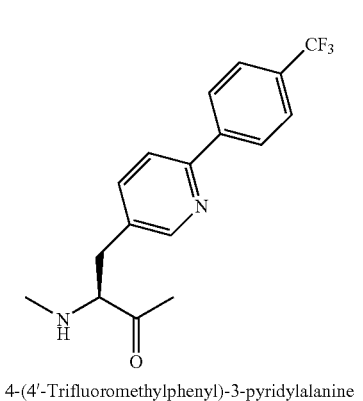
4-(4′-Trifluoromethylphenyl)-3-pyridylalanine
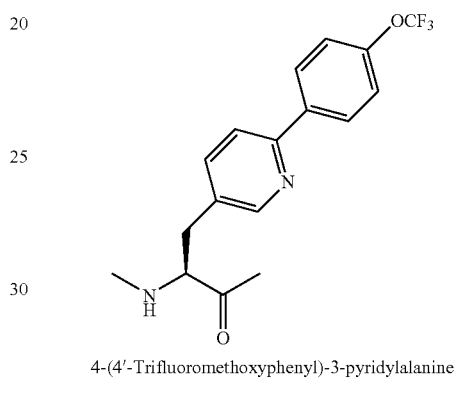
4-(4′-Trifluoromethoxyphenyl)-3-pyridylalanine
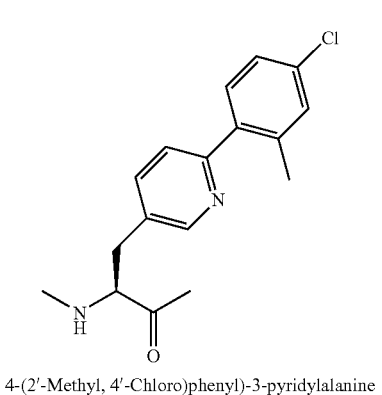
4-(2′-Methyl, 4′-Chloro)phenyl)-3-pyridylalanine
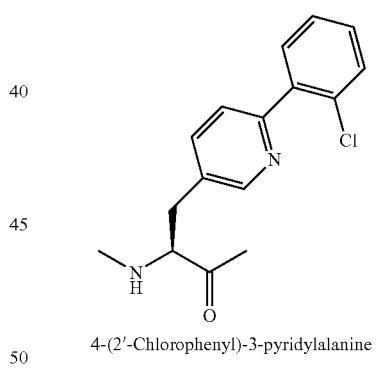
4-(2′-Chlorophenyl)-3-pyridylalanine
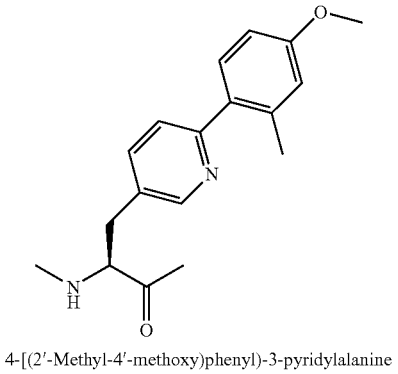
4-[(2′-Methyl-4′-methoxy)phenyl]-3-pyridylalanine
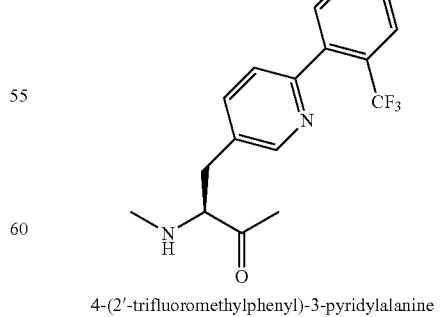
4-(2′-trifluoromethylphenyl)-3-pyridylalanine -continued
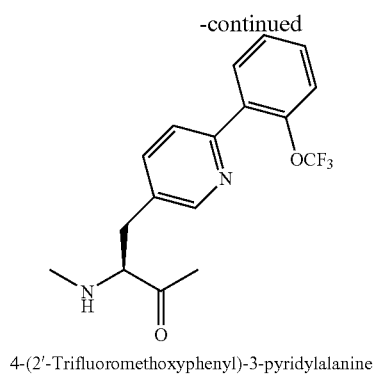
4-(2'-Trifluoromethoxyphenyl)-3-pyridylalanine
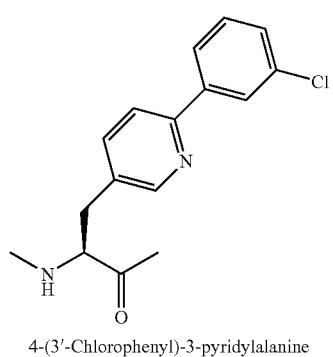
4-(3'-Chlorophenyl)-3-pyridylalanine
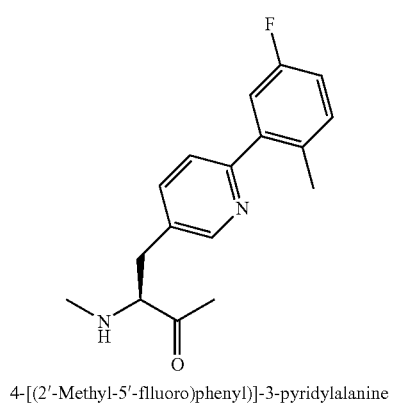
4-[(2'-Methyl-5'-flluoro)phenyl]-3-pyridylalanine
-continued
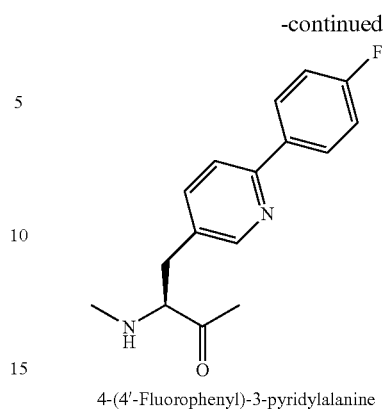
4-(4'-Fluorophenyl)-3-pyridylalanine
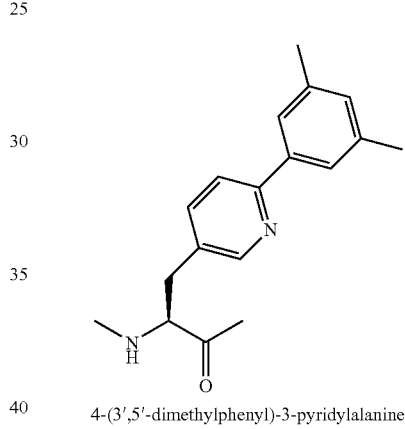
4-(3',5'-dimethylphenyl)-3-pyridylalanine
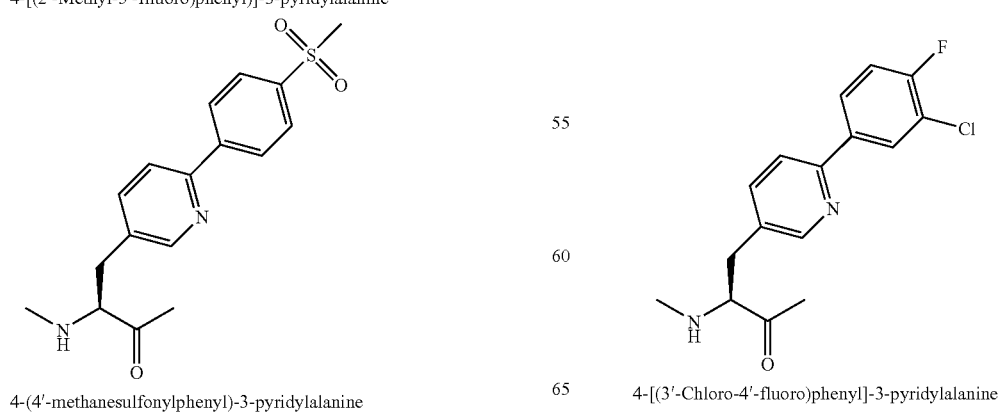
4-(4'-methanesulfonylphenyl)-3-pyridylalanine
4-[(3'-Chloro-4'-fluoro)phenyl]-3-pyridylalanine -continued
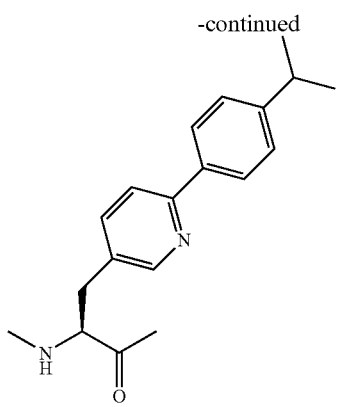
4-(4'-Isopropylphenyl)-3-pyridylalanine
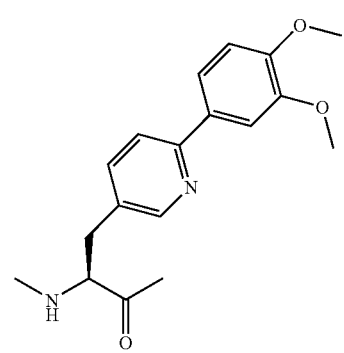
4-[(3',4'-dimethoxy)phenyl]-3-pyridylalanine
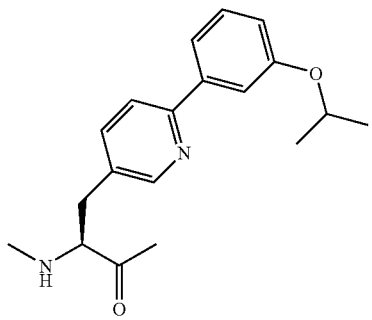
4-(3'-Isopropoxyphenyl)-3-pyridylalanine
-continued
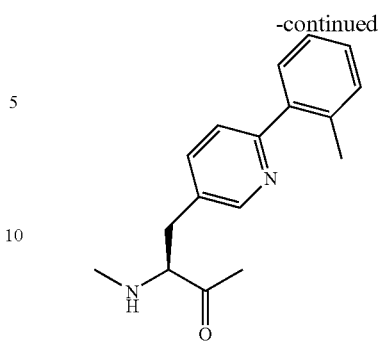
4-(2'-Methylphenyl)-3-pyridylalanine
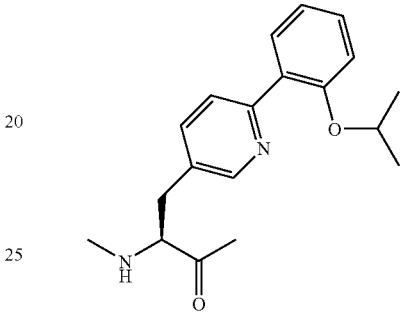
4-(2'-Isopropoxyphenyl)-3-pyridylalanine
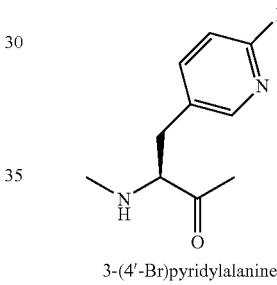
3-(4'-Br)pyridylalanine
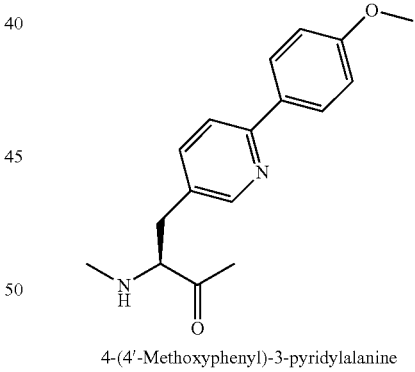
4-(4'-Methoxyphenyl)-3-pyridylalanine
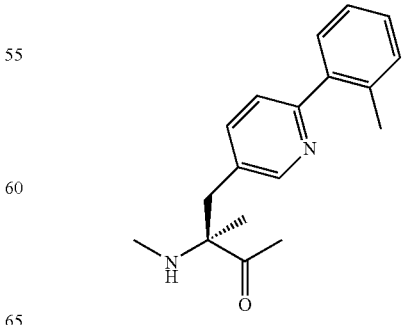
(S)-4-(2'-Methylphenyl)-α-Me-3-pyridylalanine -continued

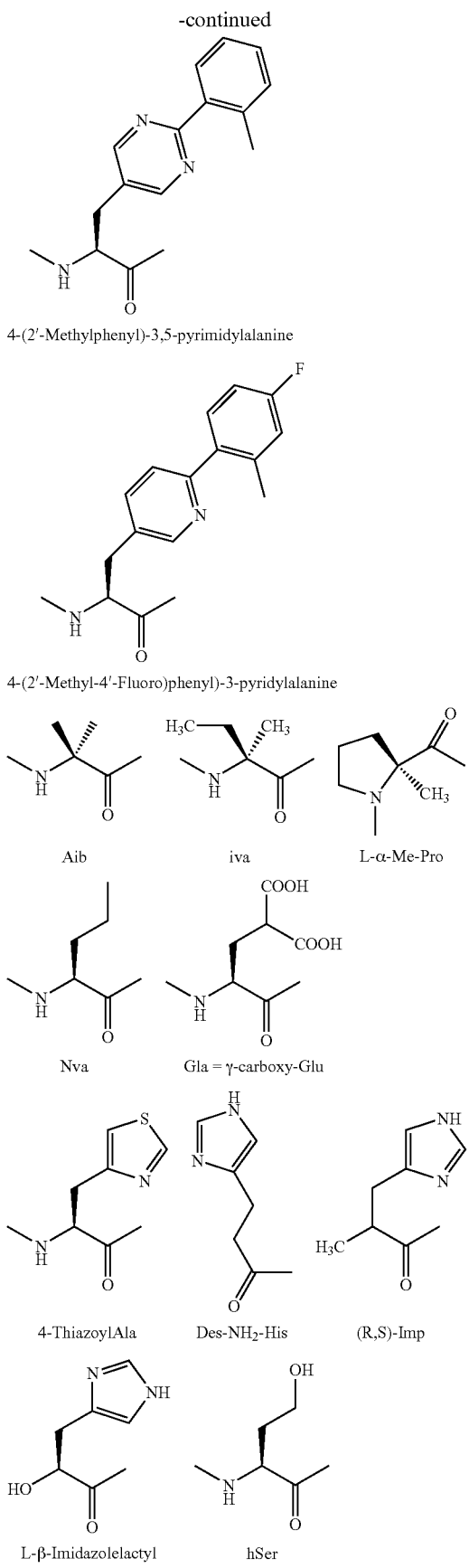

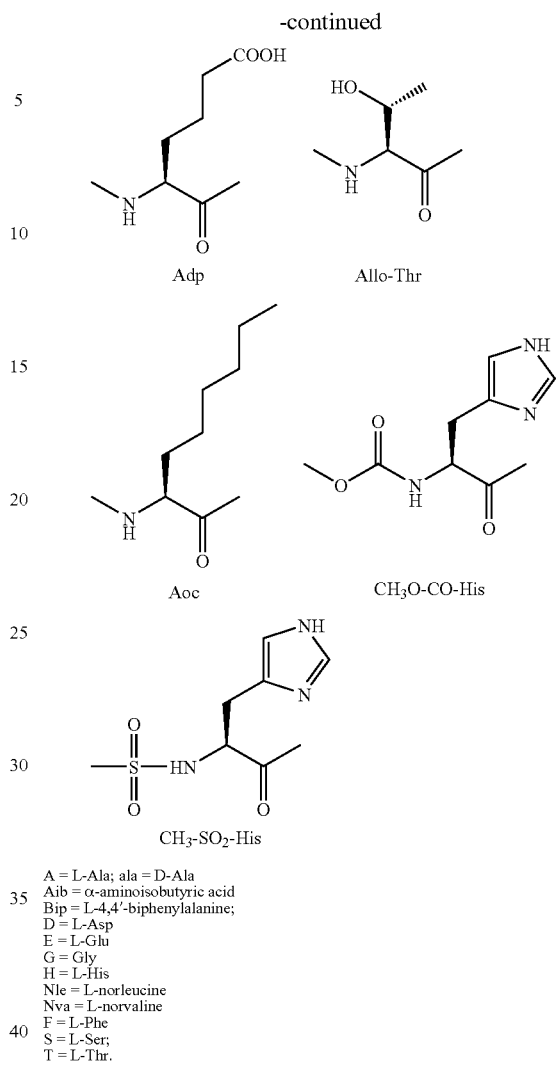

A = L-Ala; ala = D-Ala
Aib = α-aminoisobutyric acid
Bip = L-4,4'-biphenylalanine;
D = L-Asp
E = L-Glu
G = Gly
H = L-His
Nle = L-norleucine
Nva = L-norvaline
F = L-Phe
S = L-Ser;
T = L-Thr.

Those skilled in the art of amino acid and peptide chemistry may be aware that a phenylalanine amino acid bearing a phenyl substituent at the 4 or para position may otherwise be defined as a 4-(phenyl)phenylalanine or 4,4'-biphenylalanine and thus may be abbreviated as "Bip". For the purpose of the abbreviations shown in the "Amino Acid Abbreviations and Structures" section and in the Tables herein, a biphenylalanine amino acid may be abbreviated, for example, as "Bip(2'-Me)", which is intended to represent a phenylalanine substituted at its 4 position with a 2'-methylphenyl group in which the 2'-methyl group is ortho relative to the attachment point of the phenyl ring.

EXAMPLE 21

Synthesis of (2(R and S)-(((9H-fluoren-9-yl)methoxy)carbonyl)-3-(2-o-tolylpyrimidin-5-yl)propanoic acid]

The following Scheme 21 describes the synthesis of (2S)-2-(((9H-fluoren-9-yl)methoxy)carbonylamino)-3-(6-o-tolylpyrimidin-5-yl)propanoic acid hydrochloride:

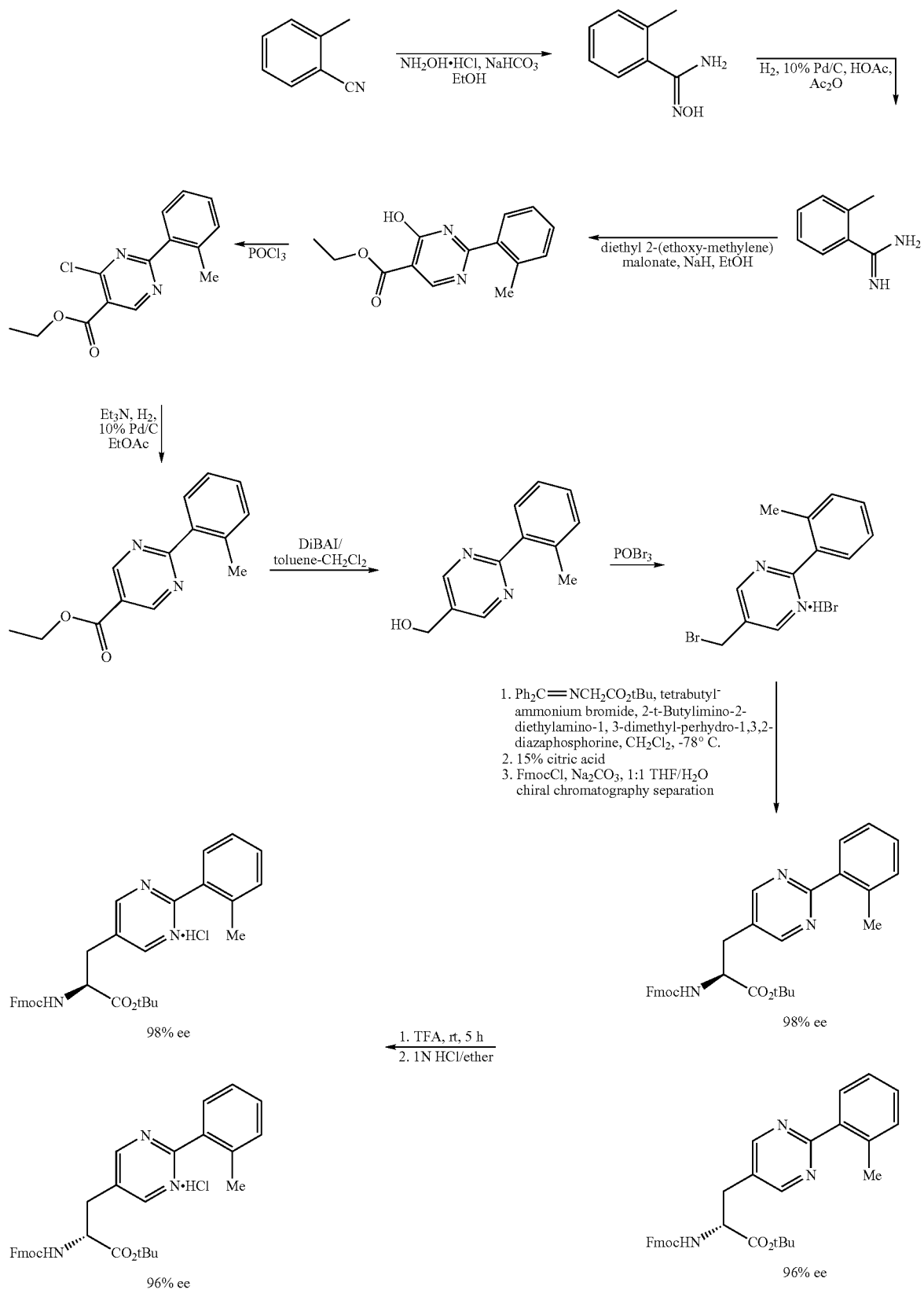

1. N'-hydroxy-2-methylbenzamidine

To a stirred solution of 9.92 g (84.7 mmol) of o-tolunitrile and 7.82 g (93.2 mmol) of sodium bicarbonate in water (20 mL) is added isopropanol (100 mL). The reaction mixture is heated to reflux under argon. After 20 h, the reaction mixture was cooled and evaporated to remove most of the isopropanol. The semi-solid residue was partitioned between water and hexane and the resulting solids were collected and dried to give a white solid, 8.03 g, 83% yield.

2. 2-methylbenzamidinium acetate

To a stirred solution of 7.82 g of the above compound (52.1 mmol) in acetic acid (100 mL) at room temperature under argon was added 5.65 mL of acetic anhydride (5.65 mmol, 1.15 eq) and 1.0 g of 10% Pd-on-C. The mixture was stirred and purged twice with argon. The mixture was then stirred under a hydrogen atmosphere (~1 atm) for 3 h. The reaction mixture was purged and filtered through Celite. Evaporation of the filtrate provided the product as a tan solid, 10.32 g, 99% yield.

3. Ethyl 4-hydroxy-2-o-tolylpyrimidine-5-carboxylate

To stirred ethanol (57 mL) under argon at 0-5° C. was added 2.35 g of sodium hydride in an oil dispersion (60%, 58.7 mmol) in portions over 10 min. After an additional 10 min, a solution of 5.70 g of 2-methylbenzamidinium acetate (29.3 mmol) was added. The resulting orange slurry was stirred as a solution of 5.93 mL of diethyl (2-ethoxy-methylene) malonate (29.3 mmol) in 14 mL of ethanol was added over 5 min. The mixture was heated to reflux, forming a solution. After 15 h, the solution was cooled and poured into 300 mL of ice water. The resulting solution was stirred and 2.3 mL of concentrated hydrochloric acid (27.6 mmol) was added to bring the solution to pH7. The resulting off-white flocculant slurry was filtered and dried under an $N_2$-stream to give the title compound as a white solid, 6.87 g, 91% yield.

4. Ethyl 4-chloro-2-o-tolylpyrimidine-5-carboxylate

A solution of 4.00 g of ethyl 4-hydroxy-2-o-tolylpyrimidine-5-carboxylate (15.5 mmol) in 11.6 mL of phosphorous oxychloride (124 mmol) was heated to reflux (calcium chloride filled tube as protection from the outside atmosphere). After 3 h, the excess $POCl_3$ was removed by distillation (~20 Torr, 90-100° C. oil bath). The residual red oil on cooling solidified. The solids were pulverized and covered with 100 mL of EtOAc. The slurry was cooled to -5° C. and agitated vigorously for 10 min with 25 mL of a potassium carbonate solution (2 M, 50 mmol). The resulting organic phase was separated, dried ($MgSO_4$), filtered and evaporated to give, after triturating in hexanes, the title compound as a light orange solid, 3.58 g, 84% yield.

5. Ethyl 2-o-tolylpyrimidine-5-carboxylate

At room temperature, a solution of 2.33 g of the above compound (8.42 mmol) and 1.17 mL of triethylamine (8.42 mmol) in 35 mL of ethyl acetate was treated with 210 mg of 10% Pd-on-C. The rapidly stirred mixture was purged twice with argon and then subjected to a hydrogen atmosphere (~3 atm) for 3 h. The reaction mixture was purged, filtered through Celite and evaporated. Re-evaporation from hexanes gave the title compound as a yellow solid, 1.88 g, 92% yield.

6. (2-o-Tolylpyrimidin-5-yl)methanol

To a stirred solution of 2.10 g of the above compound (8.67 mmol) in 45 mL of dichloromethane under argon at -78° C. was added 12.7 mL of a solution of diisobutylalum-inum in toluene (1.5 M, 19.1 mmol). After 90 min, a solution of 19.1 mL potassium sodium tartrate (1 M, 19.1 mmol) was added dropwise and the finely frozen dispersion was stirred and allowed to warm to room temperature. The mixture was partitioned between water and dichloromethane. The organic phase was separated, dried ($MgSO_4$), filtered and evaporated to give a yellow oil. Purification by silica gel chromatography (5×15 cm column, 1:1 EtOAc/hexanes) provided the title compound as a white solid, 975 mg, 56% yield.

7. (2-o-Tolylpyrimidin-5-yl)methylbromide and (R,S) t-Butyl 2-(((9H-fluoren-9-yl)methoxy)carbonyl)-3-(2-o-tolylpyrimidin-5-yl)propanoate A mixture of 918 mg of the above compound (4.58 mmol) and 2.20 g of phosphorous oxybromide (7.67 mmol) was heated to 120 deg C. (calcium-chloride filled drying tube as protection from the outside atmosphere). After 1 h, the reaction mixture was distilled (~20 Torr, 90-100° C. oil bath). The resulting black resinous residuum was cooled to room temperature, covered with EtOAc, cooled again to 0° C. and carefully treated with 10 mL of a sodium carbonate solution (2 N, 10 mmol). The organic extract, the unstable 2-o-tolylpyrimidin-5-yl)methylbromide was dried ($MgSO_4$), filtered and evaporated at <30° C. to give 1.35 g of yellow glass, to be used immediately in the following reaction.

To a stirred mixture of 1.31 g of the above compound (3.64 mmol), 1.075 g (3.64 mmol, 1.0 equivalent) of tert-butyl 2-(diphenylmethyleneamino)acetate and 117 mg (0.36 mmol, 0.1 equivalent) of tetrabutylammonium bromide in 16 mL of dichloromethane at -78° C. under argon was added 1.58 mL (5.46 mmol, 1.5 eq) of 2-t-butylimino-2-diethylamino-1,3-dimethyl-perhydro-1,3,2-diazaphosphorine over 5 min. The reaction mixture was stirred at -78° C. for 1 h and then allowed to warm to room temperature in situ. After 17 h, the mixture was directly purified by silica gel chromatography using ethyl ether/dichloromethane (3:47) as eluant (5×20 cm column), to give tert-butyl 2-(diphenylmethyleneamino)-3-(6-o-tolylpyrimidin-5-yl)propanoate yellow oil, 1.45 g, 78% yield.

To a stirred solution of 1.45 g (2.33 mmol) of tert-butyl 2-(diphenylmethyleneamino)-3-(6-o-tolylpyrimidin-5-yl) propanoate in 12 mL of THF at room temperature under argon was added 3.40 g (17.7 mmol, 5.8 equivalents) of citric acid in 12 mL of water. After 3 h, the reaction mixture was diluted with water and washed twice with ether. The aqueous phase was then brought to pH 9 with solid sodium carbonate and extracted twice with dichloromethane.

The dichloromethane extracts were combined, dried with sodium sulfate and concentrated. The resulting oil was dissolved in 6 mL of THF and treated with 4.2 mL of 10% sodium carbonate solution and then 864 mg (3.34 mmol, 1.1 equivalents) of 9-fluorenylmethyloxycarbonylchloride at room temperature. After 2 h, the reaction mixture was extracted twice with EtOAc, dried with magnesium sulfate, filtered, concentrated and purified by chromatography on silica gel using ethyl acetate/dichloromethane (1:19) as eluant (5×15 cm column), to give colorless oil, 1.61 g, 99% yield.

The product was dissolved in 1:1 EtOH/MeOH (130 mL). After 10 min, a precipitate formed. After filtration, the filtrate was subjected to chiral chromatography (Chiralpak AD column, 5×50 cm, 20μ packing; 2:2:96 MeOH/EtOH/hexanes as elutant, 50 mL/min flow rate) to give after collecting, pooling and evaporation, two fractions:

(S) t-Butyl 2-(((9H-fluoren-9-yl)methoxy)carbonyl)-3-(2-o-tolylpyrimidin-5-yl)propanoate (identified by comparison to the pyridine analog), 221 mg, >98% ee; and (R) t-Butyl 2-(((9H-fluoren-9-yl)methoxy)carbonyl)-3-(2-o-tolylpyrimidin-5-yl)propanoate, 295 mg, 96% ee, both by chiral HPLC analysis (4.6×250 mm AD column, 2:2:96 heptane:methanol:ethanol as eluant 1 mL/min flow rate).

8a. (2S)-2-(((9H-Fluoren-9-yl)methoxy)carbonylamino)-3-(6-o-tolylpyrimidin-5-yl)propanoic acid hydrochloride A solution of 220 mg (0.41 mmol) of (2S)-tert-butyl 2-(((9H-fluoren-9-yl)methoxy)carbonylamino)-3-(6-o-tolylpyrimidin-5-yl)propanoate in TFA (2.1 mL), protected from the atmosphere by a calcium chloride-filled drying tube was stirred at room temperature for 4 hours. The reaction mixture was concentrated in vacuo at less than 40° C. and the resulting orange oil was redissolved in toluene twice and evaporated to give the title compound as a white powder, 195 mg, 99% yield.

8b. (2R)-2-(((9H-Fluoren-9-yl)methoxy)carbonylamino)-3-(6-o-tolylpyrimidin-5-yl)propanoic acid hydrochloride A solution of 290 mg (0.54 mmol) of (2R)-tert-butyl 2-(((9H-fluoren-9-yl)methoxy)carbonylamino)-3-(6-o-tolylpyrimidin-5-yl)propanoate in TFA (2.7 mL), protected from the atmosphere by a calcium chloride-filled drying tube was stirred at room temperature for 4 hours. The reaction mixture was concentrated in vacuo at less than 40° C. and the resulting orange oil was redissolved in toluene twice and evaporated to give the title compound as a white powder, 255 mg, 98% yield.

EXAMPLE 22

Synthesis of (2S)-2-(((9H-fluoren-9-yl)methoxy)carbonyl)-2-methyl-3-(6-o-tolylpyridin-3-yl)propanoic acid The following Scheme 22 describes the synthesis of ((2S)-2-(((9H-fluoren-9-yl)methoxy)carbonyl)-2-methyl-3-(6-o-tolylpyridin-3-yl)propanoic acid:

Scheme 22

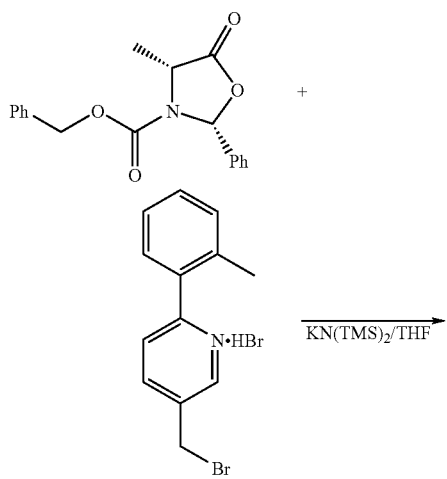

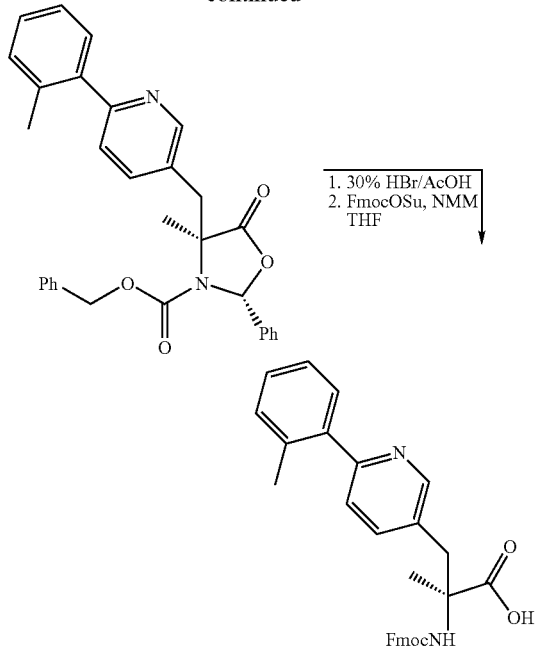

1. (2R,4S)-benzyl 4-methyl-5-oxo-2-phenyl-4-((6-o-tolylpyridin-3-yl)methyl)oxazolidine-3-carboxylate To a stirred slurry of 515 mg (1.50 mmol) of Example 11.4 at −78° C. under argon was added 3.08 mL of a solution of potassium hexamethyldisilazide (0.5 M in toluene, 1.54 mmol) After 20 min, a like amount of potassium hexamethyldisilazide and 467 mg (1.50 mmol) of (2R,4R)benzyl 4-methyl-5-oxo-2-phenyloxazolidine-3-carboxylate (S. R. Kapadia, J. Org. Chem. 66 1903 (2001)) in 2 mL of THF in separate syringes were alternatively added dropwise over 30 min. The reaction mixture was allowed to warm to room temperature. After 14 h, the reaction mixture was poured into saturated sodium bicarbonate solution and extracted twice with ether. The organic extracts were combine, dried (Na$_2$SO$_4$) filtered and evaporated. Purification by silica gel chromatography (5×15 cm column, 1:3 EtOAc/hexanes as elutant) provided the title compound as a white foam, 240 mg, 33% yield.

2. (2R,4S)-benzyl 4-methyl-5-oxo-2-phenyl-4-((6-o-tolylpyridin-3-yl)methyl)oxazolidine-3-carboxylate A stirred solution of 240 mg (0.49 mmol) of the above compound and 4 mL of 30% HBr in acetic acid was heated to reflux for 24 h. The resulting solution was evaporated to dryness and then redissolved in 9 mL of water. The solution was extracted once with ether. The aqueous phase was adjusted to pH8 with solid sodium bicarbonate (750 mg) and then stirred at room temperature as a solution of 216 mg (0.84 mmol) of FmocOSu in THF (3 mL) was added. After 60 h, the reaction mixture was quenched with 5% citric acid solution and extracted twice with EtOAc. The combined organic extracts are dried (MgSO$_4$), filtered and evaporated. Crystallization from 9:1 acetonitrile/water provided the title compound as a white solid, 52 mg, 22%.

EXAMPLE 23

Cyclic AMP Determination

The GLP-1 receptor is a G-protein coupled receptor. GLP-1 (7-36)-amide, the biologically active form, binds to the GLP-1 receptor and through signal transduction causes activation of adenylyl cyclase and increases intracellular cAMP concentrations. To monitor agonism of peptide compounds in stimulating the GLP-1 receptor, adenylyl cyclase activity was monitored by assaying for intracellular cAMP content. Full-length human glucagon-like peptide 1 receptor was stably expressed in CHO—K1 cells and clonal lines were established. The clones were screened for the greatest increase in cAMP content in response to a saturating dose of GLP-1 and clone CHO-GLP1R-19 was selected.

Cells were cultured in Ham's F12 nutritional media (Gibco # 11765-054), 10% FBS, 1×L-Glutamine, 1×Pen/Strep, and 0.4 mg/ml G418. CHO-GLP-1R-19 cells (20,000 in 100 µl of media) were plated into each well of a 96-well tissue culture microtiter plate and incubated overnight in a 5% $CO_2$ atmosphere at 37° C. On the day of the assay, cells were washed once with 100 µl of phosphate-buffered saline (PBS). A Biomek 2000 was used to serially dilute all peptides prior to beginning the assay. Serial dilutions were carried out in 100% DMSO. Peptide plates were created prior to the initiation of the assay using a Platemate Plus; 1.5 uL of compound was transferred to a V bottom plate and 150 uL of assay buffer supplemented with 100 µM 3-isobutyl-1-methylxanthine (a nonselective phosphodiesterase inhibitor) was added to the plate to give a 1:100 dilution and a 1% final concentration of DMSO.

In order to create a cAMP standard curve, a serial dilution of cAMP in the range 0.2-25.6 pmol/well was made up in lysis reagent 1 (Amersham cAMP SPA kit). 50 µl of each cAMP standard was added by hand and 70 µl of mix reagent (Amersham cAMP SPA kit) was added using the multidrop. The plates were then sealed and counted on a Trilux counter after 15 hours. This standard curve was used to convert CPM to pmol of cAMP.

1. cAMP Assay Protocol on the Platemate Plus.

Cell plates and peptide plates were loaded onto the Platemate. The media was aspirated from the wells and discarded. 100 uL per well of the peptide/buffer mixture were then added from the peptide plates to initiate the assay. After 30 minutes of incubation the peptide/buffer was removed and 50 uL of the lysis reagent 1 solution was added per well. The plate was kept for one hour at RT or overnight if refrigerated and sealed. 70 uL of the cAMP detection reagent (premixed $^{125}$I-cAMP analog, anti-cAMP antibody and anti-rabbit antibody conjugated to SPA beads—all from the Amersham cAMP SPA kit) was added using the multidrop and the plates were sealed. After 15 hours the plates were counted on a Trilux scintillation counter.

Dose dependence for compounds was determined at half-log concentrations in duplicate. Ten nM GLP-1 served as a reference standard for determination of maximal activity. A standard curve was determined using known amounts of cyclic AMP. The amounts of cAMP synthesized by the treated cells were determined from the cyclic AMP standard curve, and the percent of the maximal GLP-1 stimulated activity was calculated and plotted against log compound concentration. The data were analyzed by nonlinear regression curve fitting (4 parameter sigmoidal dose-response curve) to determine the $EC_{50}$ of the compounds. By way of example, peptides of the present invention have $EC_{50}$ values in the range of 0.0005 nM to 10 nM, more preferably in the range of 0.0005 nM to 0.200 nM.

EXAMPLE 24

In Vivo Studies

Peptides were dissolved in an appropriate vehicle at a concentration in nmol/ml equivalent to the dose that was to be administered in nmol/kg so that each mouse would receive the same volume/weight of dosing solution. Male C57BL/6J-ob/ob mice (10 weeks old) were randomized into groups of 6 mice per group based on fed plasma glucose and body weight. After an overnight fast, mice were weighed and placed in the experimental lab. After 30 min in the environment, the mice were bled via tail tip at −30 min and immediately injected subcutaneously (sc) with vehicle or the peptide dissolved in vehicle (0.1 ml solution/100 g body weight). At time 0 the mice were bled and then injected intraperitoneally with 50% glucose (2 g/kg) to initiate the intraperitoneal glucose tolerance test (ipGTT). The mice were bled 30, 60, 120 and 180 min after the glucose injection. Blood samples were drawn into potassium EDTA, placed on ice during the study and subsequently centrifuged for 10 min at 3000 rpm at 4° C. Plasma samples were diluted 11-fold for glucose analysis in the Cobas System. Another 5 µl plasma sample was diluted 5-fold with 20 µl of Sample Diluent (Insulin ELISA assay kit, Crystal Chem Inc.) and stored at −20° C. for subsequent analysis using the Ultra Sensitive Mouse Insulin ELISA kit (Crystal Chem Inc.).

Figure 2:
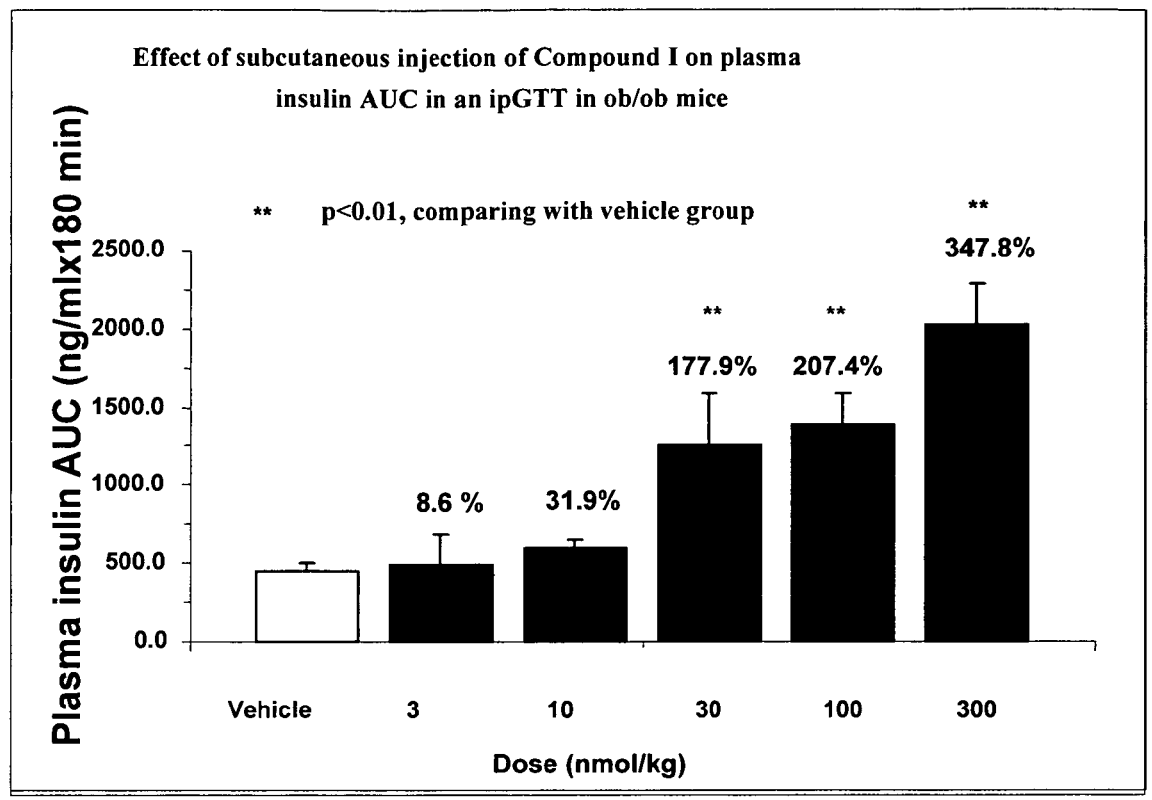
FIG. 2 illustrates the effects of subcutaneous injection of Compound I on plasma insulin in an ipGTT in ob/ob mice.

The in vivo glucose lowering properties for compound I, compound II and III in ob/ob mice (a mouse model of insulin resistance) are described above. Subcutaneous administration of peptide I attenuated the postprandial glucose excursion curve in an intraperitoneal glucose tolerance test (ipGTT), with the plasma glucose area under the curve (AUC) decreasing in a dose-dependent manner between 0 and 180 minutes (FIG. 1). The ED50 of compound I was determined to be 50 nmoles/kg. There was a concomitant and statistically significant dose-dependent increase in postprandial plasma insulin levels in these animals (FIG. 2). The correlation between changes in plasma glucose and insulin in animals treated with compound I (FIG. 1 and FIG. 2) suggests that the glucose lowering effect is mediated by stimulation of insulin release by compound I.

Figure 3:
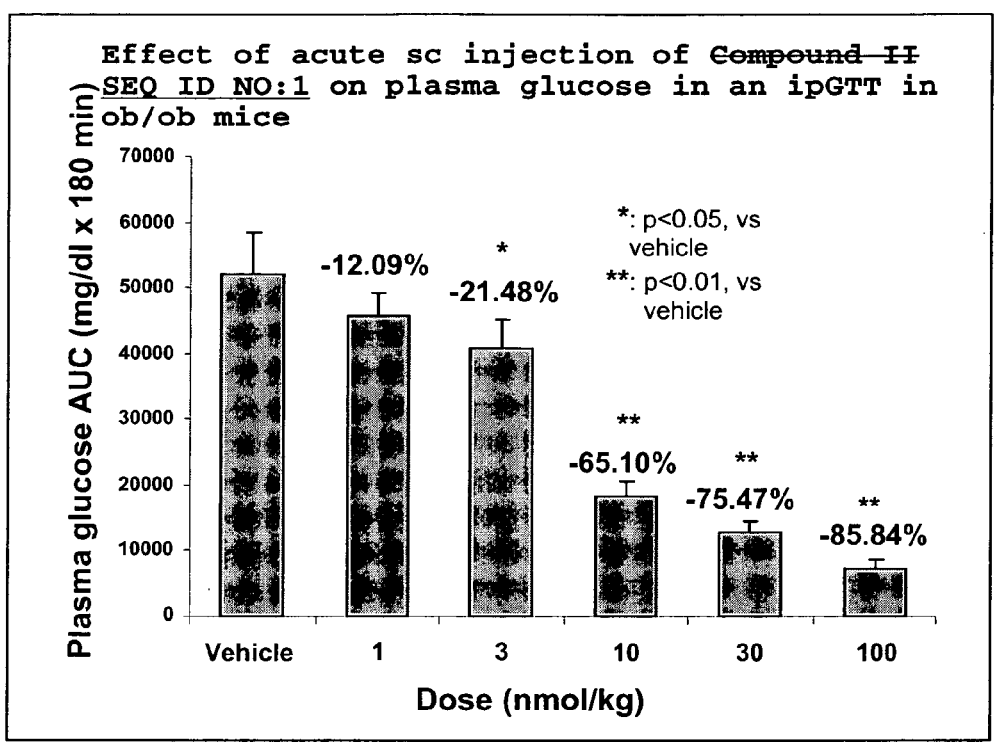
FIG. 3 illustrates the effects of subcutaneous injection of a polypeptide of SEQ ID NO:1 on plasma glucose in an ipGTT in ob/ob mice.
Figure 4:
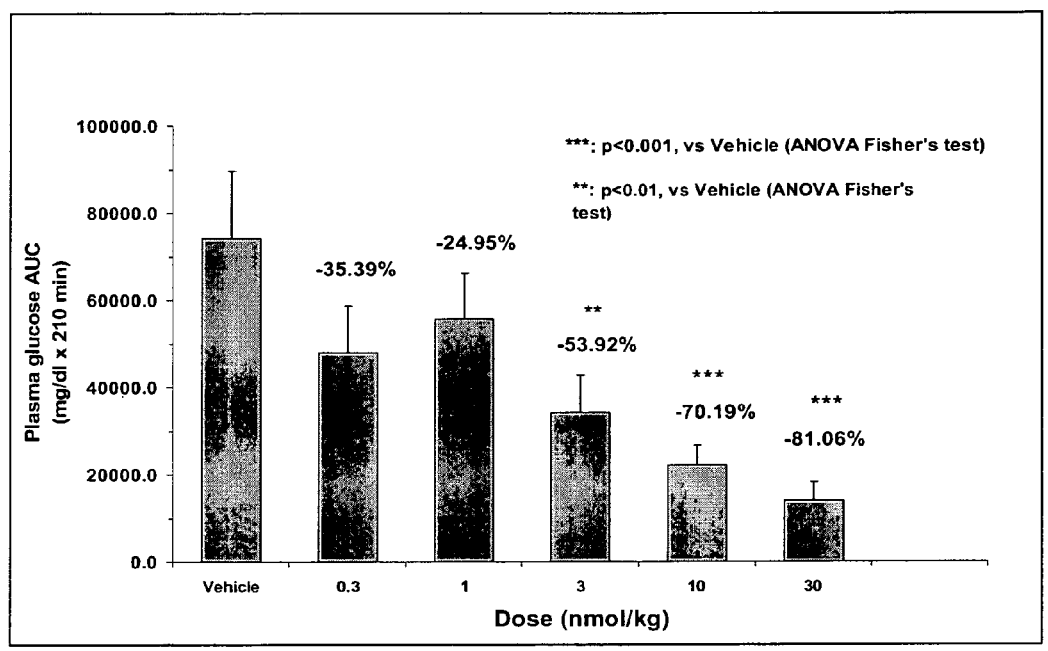
FIG. 4 illustrates the effects of subcutaneous injection of a polypeptide of SEQ ID NO:58 on plasma glucose in an ipGTT in ob/ob mice.

More significantly and unexpectedly, polypeptides of SEQ ID NO's:1 and 58 produced a time-dependent (between 0 and 180 minutes) statistically significant decrease in postprandial plasma glucose following subcutaneous administration in ob/ob mice (FIGS. 3 and 4). The effect of compound II on postprandial glucose was dose-dependent between 1-100 nmol/kg and plasma glucose AUC decreased 85.8% at 100 nmol/kg dose (FIG. 3). More significantly and unexpectedly, the $ED_{50}$ for the peptide of SEQ ID NO:1 was determined to be 5 nmoles/kg, indicating that compound II was approximately 10-fold more potent than compound I on a dose basis. The ED50 for the glucose lowering activity of the peptide of SEQ ID NO:58 was determined to be 2.5 nmol/kg (FIG. 4).

EXAMPLE 25

Dog Pharmacokinetic Study

The pharmacokinetic parameters of the peptide of SEQ ID NO:1 were determined in male beagle dogs (n=4, 14±1 kg). Following an overnight fast, each animal received the peptide of SEQ ID NO:1 either as an intravenous bolus via femoral vein (67 µg/kg) or by subcutaneous injection given at near the shoulder blades (67 µg/kg). Each animal received both intravenous and subcutaneous doses with a one-week washout between doses following a crossover design. The dosing vehicle for both routes of administration was propylene glycol:phosphate buffer (50:50). Serial blood samples were collected in EDTA-containing microcentrifuge tubes at predose, 0.083, 0.25, 0.5, 0.75, 1, 2, 4, 6, 8, 24, and 30 hours post-dose after intravenous administration; at predose, 0.25, 0.5, 0.75, 1, 2, 4, 6, 8, 24, and 30 hours post-dose after subcutaneous administration. Approximately 0.3 mL of blood was collected at each time point. Blood samples were immediately centrifuged at 4° C. The obtained plasma was frozen with dry ice and stored at −20°C. Plasma drug levels were determined using the LC-MS/MS assay described above.

Quantitation of a Peptide of SEQ ID NO:1 by LC-MS/MS

Plasma samples from in vivo dog study were prepared for analysis by precipitating plasma proteins with two volumes of acetonitrile containing an internal standard. The samples were vortex mixed and removed the precipitated proteins by centrifugation. The resulting supernatants were transferred to a 96-well plate and 10 μL were injected for analysis. Samples were prepared with the Packard Multiprobe II and Quadra 96 Liquid Handling System.

The HPLC system consisted of two Shimadzu LC10AD pumps (Columbia, Md.), a CTC PAL autosampler (Leap Technologies, Switzerland). The column used was a YMC Hydrosphere C18 (2.0×50 mm, 3 μm) (YMC, Inc., Milford, Mass.). The column temperature was maintained at 50° C. and the flow rate was 0.3 mL/minute. The mobile phase A consisted of 10 mM ammonium formate and 0.1% formic acid in water and mobile phase B consisted of 0.1% formic acid in acetonitrile. The initial mobile phase composition was 5% B, and remained at 5% B for one minute to equilibrate the column. The composition was ramped to 95% B over two minutes and held there for one additional minute. The mobile phase was then returned to initial conditions in one minute. Total analysis time was five minutes. A switching valve was used. The eluents between 0-1 minute were diverted to the waste.

The HPLC was interfaced to a Sciex API 4000 mass spectrometer, (Applied Biosystems, Foster City, CA) and was equipped with a Turbolonspray ionization source. Ultra high purity nitrogen was used as the nebulizing and turbo gas. The temperature of turbo gas was set at 300° C. and the interface heater was set at 60° C. Data acquisition utilized selected reaction monitoring (SRM). Ions representing the $(M+2H)^{2+}$ species for the peptide of SEQ ID NO:1, and $(M+2H)^{2+}$ for BMS-501143 (IS) were selected in Q1 and were collisionally dissociated with high purity nitrogen at a pressure of 3.5×10 torr to form specific product ions which were subsequently monitored by Q3. The transitions and voltages are summarized in Table 4.

TABLE 4

Parameters for MS/MS Analysis of a peptide of SEQ ID NO:1 and internal standard

|  | SEQ ID NO:1 | Internal Standard |
| --- | --- | --- |
| SRM transition (mz) | 765.1->195.2 | 740.7-> 210.0 |
| Declustering Potential (V) | 60 | 60 |
| Collision Energy (V) | 45 | 30 |

The standard curve concentrations, ranging from 1 to 1000 nM and from 4 to 5000 nM, were used for the in vivo samples obtained from low and high doses, respectively. The curves were fitted with a quadratic regression weighted by reciprocal concentration ($1/x^2$). Standards were analyzed in duplicate. Quality control (QC) samples, prepared in blank matrix at the same concentrations as the standard were also analyzed in each analytical set. For the peptide of SEQ ID NO:1, the calculated concentrations of more than 80% of the QCs were within 20% of nominal concentration, indicating acceptable assay performance.

Data Analysis

The plasma concentration of a peptide of SEQ ID NO:1 vs. time data were analyzed by noncompartmental methods using the KINETICA™ software program. The Cmax and Tmax values were recorded directly from experimental observations. The AUC0-n and AUCtot values were calculated using a combination of linear and log trapezoidal summations. The total plasma clearance ($CL_p$), terminal half life ($t_{1/2}$), mean residence time (MRT), and the steady state volume of distribution (Vss) were calculated after intraarterial or intravenous administration. The total blood clearance ($CL_B$) was calculated using the total plasma clearance and the blood to plasma concentration ratio. $CL_B$ and Vss values were compared to standard liver blood flow and total body water values, respectively, reported in the literature. The absolute subcutaneous bioavailability (expressed as %) was estimated by taking the ratio of dose -normalized AUC values after a subcutaneous dose of a peptide of SEQ ID NO:1 to that after an intravenous dose.

Dog Pharmacokinetics Results

The pharmacokinetic parameters of a peptide of SEQ ID NO:1 in male beagle dogs, following intravenous (IV) and subcutaneous (SC) administration are summarized in Table 5.

The peptide of SEQ ID NO:1 exhibited low systemic clearance (0.9±0.2 mL/min/kg; 3.2% of liver blood flow, 31 mL/min/kg). The steady-state volume of distribution (Vss) was 0.10±0.03 L/kg (2 times of vascular fluid, 0.05 L/kg; 71% of extracellular fluid, 0.14 L/kg), indicating limited extravascular distribution. The estimated elimination half-life was 5.1±0.5 h and the mean residence time was 3.0±1.0 h. The time to reach peak concentrations (Tmax) after a subcutaneous dose of 67 μg/kg occurred at 5.0±1.0 h. The maximum plasma concentration (Cmax) after subcutaneous administration was 90±29 nM. The subcutaneous bioavailability of a peptide of SEQ ID NO:1 in dogs was 93±22%.

TABLE 2

Pharmacokinetic Parameters of Compound II in the Dog.

| Parameter | Intravenous (n = 3, Mean ± SD) | Subcutaneous (n = 3, Mean ± SD) |
| --- | --- | --- |
| Dose (μg/kg) | 67 | 67 |
| Cmax (nM) | — | 90 ± 29 |
| Tmax (h) | — | 5.0 ± 1.0 |
| AUCtot (nM × h) | 1266 ± 299 | 1223 ± 276 |
| $CL_p$ (mL/min/kg) | 0.6 ± 0.1 | — |
| $CL_B$ (mL/min/kg) | 0.9 ± 0.2 | — |
| $V_{SS}$ (L/kg) | 0.10 ± 0.03 | — |
| $t_{1/2}$ (h) | 5.1 ± 0.5 | 6.9 ± 1.3 |
| MRT (h) | 3.0 ± 1.0 | 12.5 ± 2.4 |
| Bioavailability (%) | — | 93 ± 22 |

EXAMPLE 26

Parenteral Routes of Administration

A. A liquid formulation for pulmonary/inhalation or nasal delivery, having the following composition is prepared as described below.

| Ingredient | Amount |
| --- | --- |
| 11-mer peptide drug | 10 mg |
| HCl or NaOH | To adjust pH between 5–8 |
| SBE-cyclodextrin (Captisol) | 50 mg |
| Purified water | q.s. to 1 ml |

Weighed amount of 11-mer peptide is dissolved in a portion of water at an optimum pH. Captisol is added to the drug solution and stirred for about 5 min. NaOH and HCL are added to adjust pH to desired value (between 5-8). Purified water is added to bring final volume to 1 ml. Other inactive ingredients such as preservatives, antioxidants, buffer salts, and cosolvents may be added as needed, prior to pH adjustment. Water is added to the desired target volume.

The above solution formulation can be administered to the lung as a fine spray with a syringe microsprayer, or an air-jet or ultrasound nebulizer. The above solution can be delivered to the nasal cavity with a metered nasal spray pump or syringe microsprayer.

B. A dry powder formulation for pulmonary/inhalation or nasal delivery, having the following composition is prepared as described below.

| Ingredient | Amount |
| --- | --- |
| 11-mer peptide drug | 10 mg |
| Lactose | 90 mg |

Weighed amount of 11-mer peptide, preferably with a mass median aerodynamic diameter (MMAD) of less than 5 micron, is blended with inhalation grade lactose 30-100 μm (Respitose, DMV International) in a Turbula® mixer for 5 min. The above dry powder blend can be delivered to the lung by a powder insufflator, or dry powder inhaler.

C. A suspension formulation for pulmonary/inhalation or nasal delivery, having the following composition is prepared as described below.

| Ingredient | Amount |
| --- | --- |
| 11-mer peptide drug | 10 mg |
| Lecithin | 0.1% |
| Propellant gas | 1 ml |

Micronized 11-mer peptide is homogeneously suspended in a mixture of lecithin and propellant gas such as hydrofluorocarbons (HFA's). The suspension is transferred to a pressurized metered dose inhaler.

D. 11-mer Peptide Absorption from a Solution Formulation in Rats

| Pharmacokinetic Parameters | Intra-trachea | Intra-nasal |
| --- | --- | --- |
| Dose (mg/kg) | 1 | 0.6 |
| AUC (nM · h) | 918.9 ± 103 | 177 ± 77 |
| Cmax (nM) | 359 ± 50.9 | 236 ± 125 |
| Tmax (h) | 0.03 | 0.17 |

An 11-mer peptide was administered as a solution (described above) to male Sprague-Dawley rats anesthetized with intraperitoneal injection of pentobarbital. Drug was introduced into the trachea with a syringe microsprayer to assess pulmonary delivery or instilled with a pipettor into each nostril for intranasal delivery. Blood samples were collected from the cannulated carotid artery into heparinized vaccutainers over a 4 hr period. The blood samples were centrifuged, the isolated plasma stored at −80° C. till analysis by LC/MS. From the plasma-time concentration curves the pharmacokinetic parameters were calculated and reported in the table. Three rats were used for each route of administration. Data is provided as a mean±standard deviation. Tmax is reported as a median value.

UTILITY & COMBINATIONS

A. Utilities

The present invention provides novel 11-mer peptides which have superior properties and act as GLP-1 receptor modulators, for example such that the 11-mer peptides have agonist activity for the GLP-1 receptor. Further, the 11-mer peptides of the present invention exhibit increased stability to proteolytic cleavage as compared to GLP-1 native sequences.

Accordingly, compounds of the present invention can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis, hypertension, AIDS, intestinal diseases (such as necrotizing enteritis, microvillus inclusion disease or celiac disease), inflammatory bowel syndrome, chemotherapy-induced intestinal mucosal atrophy or injury, anorexia nervosa, osteoporosis, dysmetabolic syndrome, as well as inflammatory bowel disease (such as Crohn's disease and ulcerative colitis). The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of Formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GLP-1 receptor modulators (e.g., agonists or partial agonists, such as a peptide agonist) or other suitable therapeutic agents useful in the treatment of the aforementioned disorders including: anti-diabetic agents; anti-hyperglycemic agents; hypolipidemic/lipid lowering agents; anti-obesity agents (including appetite suppressants/modulators) and anti-hypertensive agents. In addition, the compounds of the present invention may be combined with one or more of the following therapeutic agents; infertility agents, agents for treating polycystic ovary syndrome, agents for treating growth disorders, agents for treating frailty, agents for treating arthritis, agents for preventing allograft rejection in transplantation, agents for treating autoimmune diseases, anti-AIDS agents, anti-osteoporosis agents, agents for treating immunomodulatory diseases, antithrombotic agents, agents for the treatment of cardiovascular disease, antibiotic agents, anti-psychotic agents, agents for treating chronic inflammatory bowel disease or syndrome and/or agents for treating anorexia nervosa.

Examples of suitable anti-diabetic agents for use in combination with the compounds of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), DPP-IV inhibitors, and SGLT2 inhibitors.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include muraglitazar (Bristol-Myers Squibb), AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/644,598, filed Sep. 18, 2000, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors that may be used in combination with the compounds of the invention include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, LAF237, saxagliptin, MK0431, TSL-225 (tryptophyl-1,2,3,4-tetrahydroisoquinoline-3-carboxylic acid (disclosed by Yamada et al, Bioorg. & Med. Chem. Lett. 8 (1998) 1537-1540, 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996) employing dosages as set out in the above references.

Suitable meglitinides include nateglinide (Novartis) or KAD1229 (PF/Kissei).

Examples of other suitable glucagon-like peptide-1 (GLP-1) compounds that may be used in combination with the GLP-1 receptor modulators (e.g., agonists or partial agonists) of the present invention include GLP-1 (1-36) amide, GLP-1 (7-36) amide, GLP-1 (7-37) (as disclosed in U.S. Pat. No. 5,614,492 to Habener), as well as AC2993 (Amylin), LY-315902 (Lilly) and NN2211 (Novo Nordisk).

Examples of suitable hypolipidemic/lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440, all of which are incorporated by reference herein.

The HMG CoA reductase inhibitors which may be employed in combination with one or more compounds of Formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Desired hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, *J. Am. Chem. Soc.*, 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with one or more compounds of Formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of Formula I include those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425-430 (1999).

The lipoxygenase inhibitors which may be employed in combination with one or more compounds of Formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a NPY receptor antagonist, a NPY-Y2 or NPY-Y4 receptor agonist, a MCH antagonist, a GHSR antagonist, a CRH antagonist, a beta 3 adrenergic agonist, a lipase inhibitor, a serotonin (and dopamine) reuptake inhibitor, a thyroid receptor beta drug, a CB-1 antagonist and/or an anorectic agent.

The beta 3 adrenergic agonists which may be optionally employed in combination with compounds of the present invention include AJ9677 (Takeda/Dainippon), L750355 (Merck), or CP331648 (Pfizer) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor which may be optionally employed in combination with a compound of Formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF), WO99/00353 (KaroBio) and GB98/284425 (KaroBio), with compounds of the KaroBio applications being preferred.

Examples of CB-1 antagonists which may be optionally employed in combination with compounds of the present invention include CB-1 antagonists and rimonabant (SR141716A)

Examples of NPY-Y2 and NPY-Y4 receptor agonists include PYY(3-36) and Pancreatic Polypeptide (PP), respectively.

The anorectic agent which may be optionally employed in combination with compounds of the present invention include dexamphetamine, phentermine, phenylpropanolamine or mazindol, with dexamphetamine being preferred.

Examples of suitable anti-psychotic agents include clozapine, haloperidol, olanzapine (Zyprexa®), Prozac® and aripiprazole (Abilify®).

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

Dosage and Formulation

A suitable 11-mer peptide of Formula I can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in "The Pharmacological Basis of Therapeutics", Ch. 1, p. 1, 1975; "Remington's Pharmaceutical Sciences", 18$^{th}$ ed., Mack Publishing Co, Easton, Pa., 1990).

The pharmaceutically acceptable 11-mer peptide composition of the present invention can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The composition of the present invention can also be administered in oral, intravenous (bolus or infusion), intraperitoneal, subcutaneous, transdermally or intramuscular form, all using dosage forms well known to those of ordinary skill in the pharmaceutical arts. The composition may be administered alone, but generally will be administered with a pharmaceutical carrier selected on the basis of the chosen route of administration and standard pharmaceutical practice.

The dosage regimen for the composition of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The composition of this invention may be administered in a single daily dose, or the total daily dosage may be administered in divided doses of two, three, or four times daily. The composition of this invention may also be administered by a depot formulation that will allow sustained release of the drug over a period of days/weeks/months as desired.

The composition of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The composition is typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The composition of the present invention may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same and compositions containing the same.

The compositions of the present invention may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the composition of the present invention may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington: "The Science and Practice of Pharmacy", Nineteenth Edition, Mack Publishing Company, 1995, a standard reference text in this field Representative useful pharmaceutical dosage forms for administration of the compound of this invention can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of an 11-mer peptide composition of the present invention may or may not require the use of excipients such as those that have been approved by regulatory bodies. These excipients include, but are not limited to, solvents and co-solvents, solubilizing, emulsifying or thickening agents, chelating agents, anti-oxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Obviously, numerous modifications and variations of the present invention are possible in light of the above teachings. It is therefore understood that within the scope of the appended claims, the invention may be practiced otherwise than as specifically described herein.

The present invention is not to be limited in scope by the specific embodiments described that are intended as single illustrations of individual aspects of the invention. Functionally equivalent methods and components in addition to those shown and described herein will become apparent to those skilled in the art from the foregoing description and accompanying drawings. Such modifications are intended to fall within the scope of the appended claims. All references cited herein are hereby incorporated by reference in their entirety.

What is claimed is:

1. A polypeptide comprising the amino acid sequence of SEQ ID NO: 93 wherein said polypeptide binds and activates a GLP-1 receptor.

2. A pharmaceutical composition, comprising a polypeptide of claim 1 and a pharmaceutically acceptable carrier thereof.

3. A pharmaceutical combination comprising a polypeptide of claim 1 and at least one therapeutic agent selected from the group consisting of an antidiabetic agent, an anti-obesity agent, an anti-hypertensive agent, an anti-atherosclerotic agent and a lipid-lowering agent.

4. The combination of claim 3 wherein the antidiabetic agent is at least one agent selected from the group consisting of a biguanide, a sulfonyl urea, a glucosidase inhibitor, a peroxisome proliferator-activated receptor (PPALR) γ agonist, a PPAR α/γ dual agonist, an adipocyte lipid binding protein (aP2) inhibitor, a dipeptidyl peptidase 4 (DP4) inhibitor, an insulin sensitizer, a glucagon-like peptide-1(GLP-1), insulin and a meglitinide.

5. The combination of claim 4 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, farglitizar, isaglitazone, reglitizar, muraglitazar, saxagliptin, balaglitazone, (Z)-1,4-bis {4-[(3,5-Dioxo-1,2,4-oxadiazolidin-2-yl) methyl] phenoxy}but-2-ene, rivoglitazone, rafaegron, repaglinide, nateglinide, (S)-2-benzyl-4-oxo-4-(cis-perhydroisoindol-2-yl)butyric acid calcium salt, tesaglitizar, L-phenylalanine,N-[(1Z)-1-methyl-3-oxo-3-phenyl-1-propenyl]-4-[3-(5-methyl-2-phenyl-4-oxazolyl)propyl], 5-[(2,4-dioxo-5-thiazolidinyl)meth]-2-methoxy-N-[[4-(trifluoromethyl) phenyl]methyl]-benzamide, exenatide, 8-37-glucagon-like peptide I (human)-N-[3-(1H-imidazol-4-yl)-1-oxopropyl]-26-L-arginine-34-[N6-(1-oxooctyl)-L-lysine], and vildagliptin.

6. The combination of claim 3 wherein the anti-obesity agent is at least one agent selected from the group consisting of a beta 3 adrenergic agonist, a lipase inhibitor, a serotonin reuptake inhibitor, a dopamine reuptake inhibitor, a serotonin and dopamine reuptake inhibitor, a thyroid receptor beta compound, and an anorectic agent.

7. The combination of claim 6 wherein the anti-obesity agent is at least one agent selected from the group consisting of orlistat, cetilistat, rafabregon, N-[4-[2-[[((2S)-3-[(6-amino-3-pyridinyl)oxy]-2-hydroxypropyl]amino]ethyl]phenyl]-4-(1-methylethyl)-benzenesulfonamide, sibutramine, topiramate, axokine, dexamphetamine, phentermine, phenylpropanolamine, rimonabant and mazindol.

8. The combination of claim 3 wherein the lipid lowering agent is at least one agent selected from the group consisting of a microsomal triglyceride transfer protein (MTP) inhibitor, cholesterol ester transfer protein, a hydroxy-3-methyl-glutaryl -coenzyme A (HMG CoA) reductase inhibitor, a squalene synthetase inhibitor, a fibric acid derivative, an upregulator of low-density lipoprotein (LDL) receptor activity, a lipoxygenase inhibitor, or an acyl coenzyme A-cholesterol acyltransferase (ACAT) inhibitor.

9. The combination of claim 8 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, N-[2,6-bis(1-methylethyl)phenyl]-2-(tetradecylthio)-acetamide, 3-(13-hydroxy-10-oxotetradecyl)-5,7-dimethoxy-1(3H)-isobenzofuranone, torcetrapib, and (3 alpha, 4alpha,5 alpha)-4-(2-propenyl-cholestan-3-ol).

10. A polypeptide comprising a sequence selected from the group consisting of SEQ ID NOs: 1-16, 18-59, 61-63, 65-77, 79, 81-89, and 91-92.

11. A pharmaceutical composition comprising a polypeptide selected from the group consisting of:

217                                                                                 218
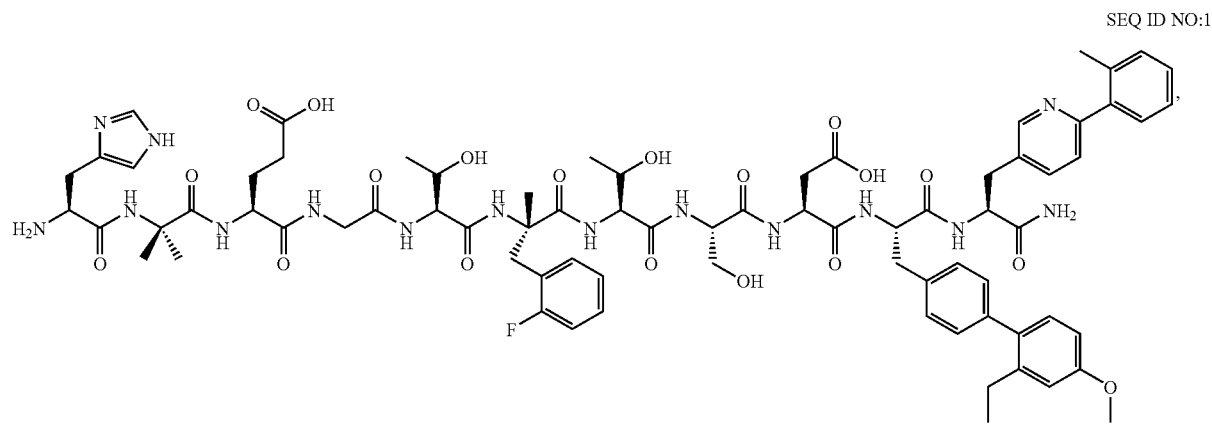
SEQ ID NO:1
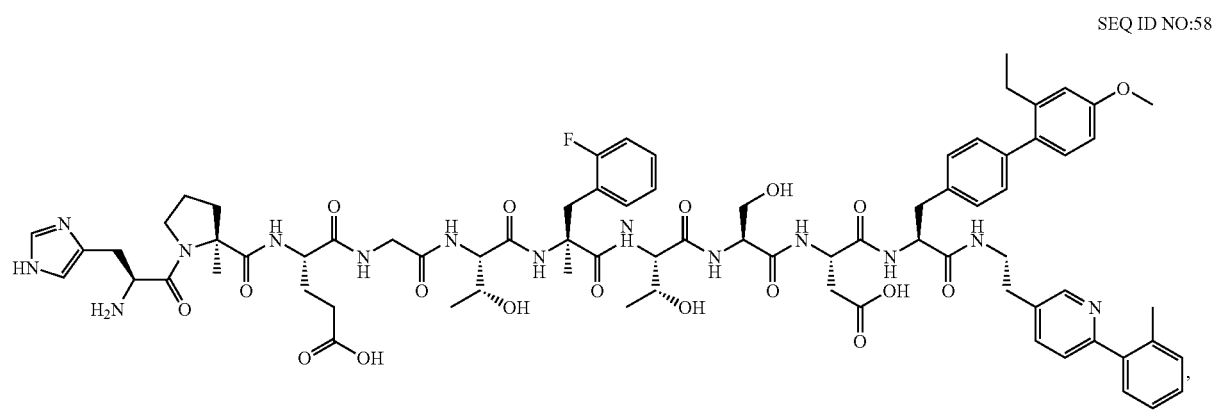
SEQ ID NO:58
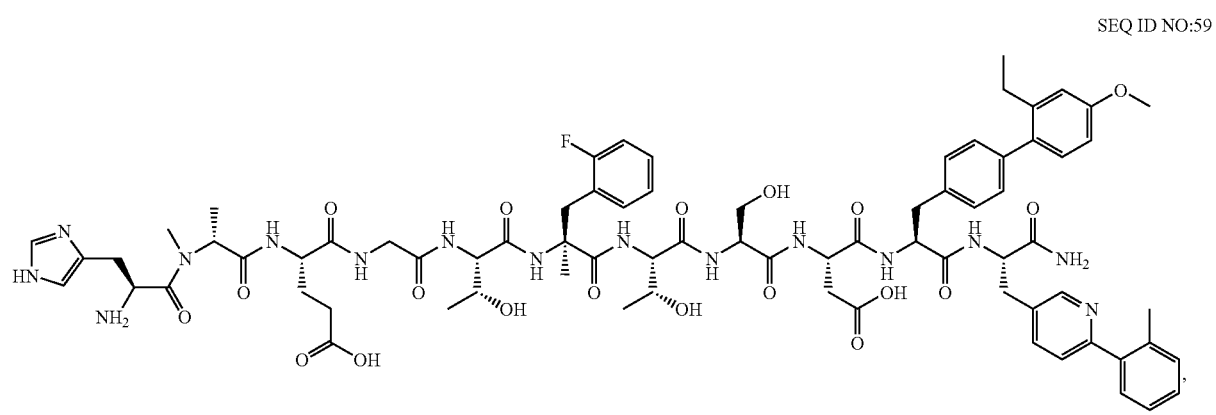
SEQ ID NO:59

SEQ ID NO:73
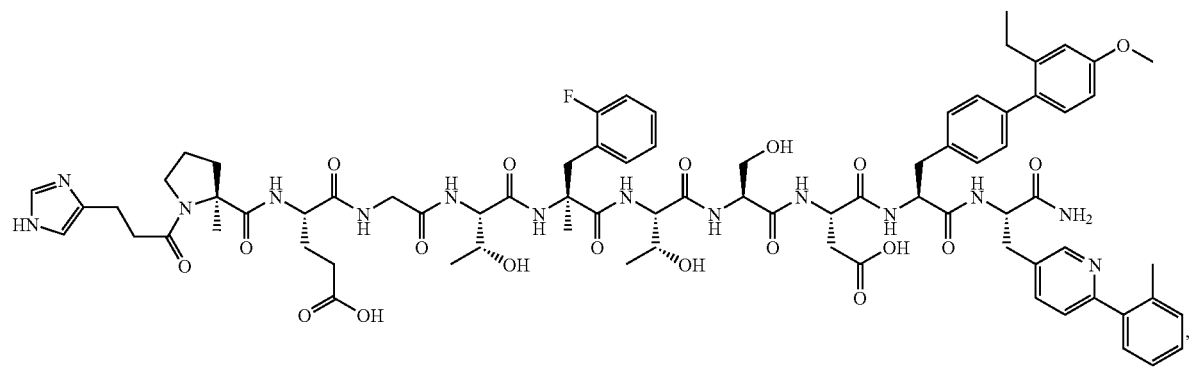
SEQ ID NO:79
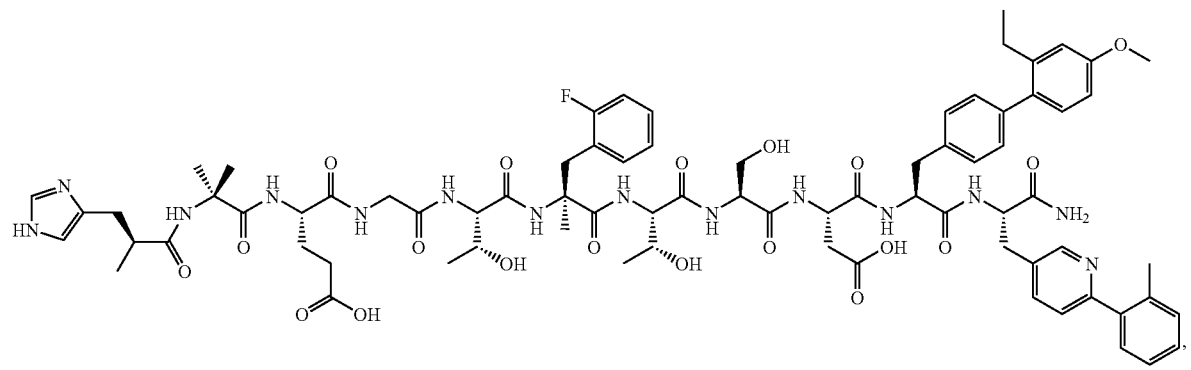
SEQ ID NO:81
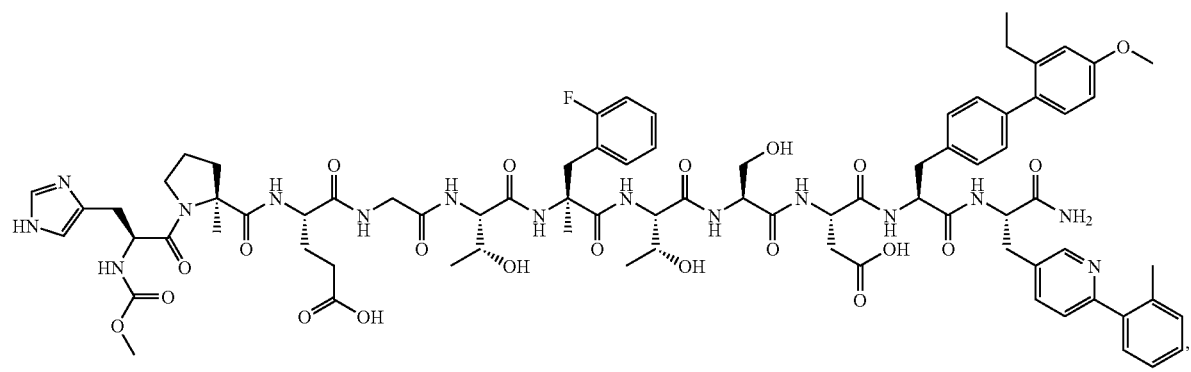

SEQ ID NO:86

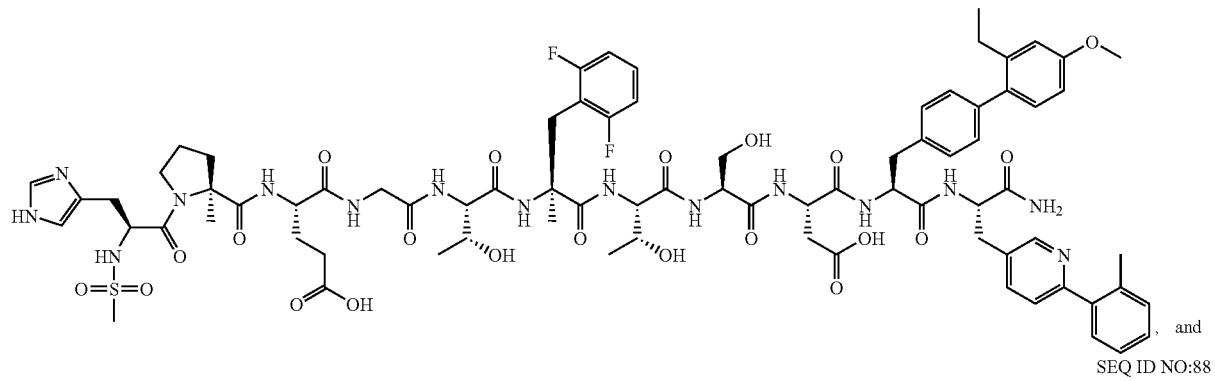

, and

SEQ ID NO:88

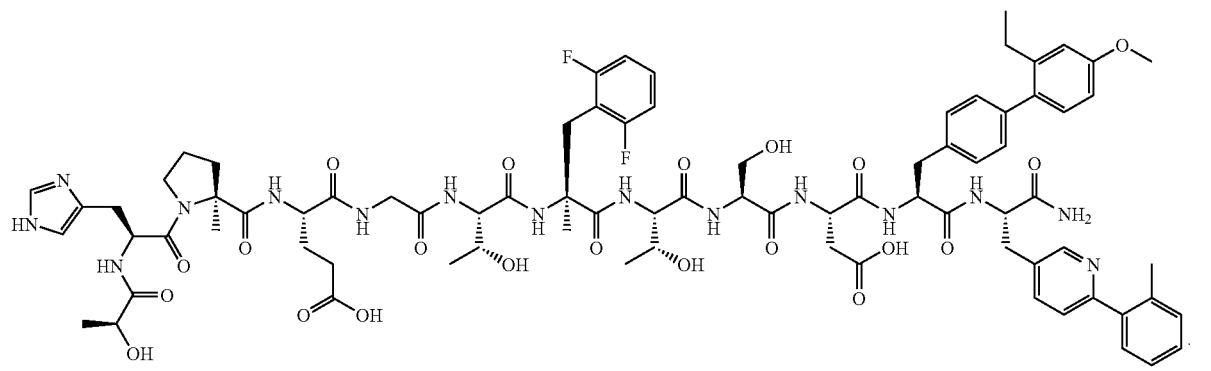

12. A polypeptide of claim 1 wherein said peptide comprises the amino acid sequence selected from the group consisting of SEQ ID NOs: 1, 58, 59, 61, 70, 81, 82, 91, and 92.

13. A polypeptide comprising the amino acid sequence of SEQ ID NO: 1.

14. A pharmaceutical composition, comprising a polypeptide of claim 13 and a pharmaceutically acceptable carrier thereof.

15. A pharmaceutical combination comprising a polypeptide of claim 13 and at least one therapeutic agent selected from the group consisting of an antidiabetic agent, an anti-obesity agent, an anti-hypertensive agent, an anti-atherosclerotic agent and a lipid-lowering agent.

16. The combination of claim 15 wherein the antidiabetic agent is at least one agent selected from the group consisting of a biguanide, a sulfonyl urea, a glucosidase inhibitor, a peroxisome proliferator-activated receptor (PPAR) γ agonist, a PPAR α/γ dual agonist, an adipocyte lipid binding protein (aP2) inhibitor, a dipeptidyl peptidase 4 (DP4) inhibitor, an insulin sensitizer, a glucagon-like peptide-1(GLP-1), insulin and a meglitinide.

17. The combination of claim 16 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, farglitizar, isaglitazone, reglitizar, muraglitazar, saxagliptin, balaglitazone, (Z)-1,4-bis {4-[(3,5-Dioxo-1,2,4-oxadiazolidin-2-yl) methyl] phenoxy}but-2-ene, rivoglitazone, rafaegron, repaglinide, nateglinide, (S)-2-benzyl-4-oxo-4-(cis-perhydroisoindol-2-yl)butyric acid calcium salt, tesaglitizar, L-phenylalanine,N-[(1Z)-1-methyl-3-oxo-3-phenyl-1-propenyl]-4-[3-(5-methyl-2-phenyl-4-oxazolyl)propyl], 5-[(2,4-dioxo-5-thiazolidinyl)methy[-2-methoxy-N-[[4-(trifluoromethyl) phenyl]methyl]-benzamide, exenatide, 8-37-glucagon-like peptide I (human)-N-[3-(1H-imidazol-4-yl)-1-oxopropyl]-26-L-arginine-34-[N6-(1-oxooctyl)-L-lysine], and vildagliptin.

18. The combination of claim 15 wherein the anti-obesity agent is at least one agent selected from the group consisting of a beta 3 adrenergic agonist, a lipase inhibitor, a serotonin reuptake inhibitor, a dopamine reuptake inhibitor, a serotonin and dopamine reuptake inhibitor, a thyroid receptor beta compound, and an anorectic agent.

19. The combination of claim 18 wherein the anti-obesity agent is at least one agent selected from the group consisting of orlistat, cetilistat, rafabregon, N-[4-[2-[[(2S)-3-[(6-amino-3-pyridinyl)oxy]-2-hydroxypropyl]amino]ethyl]phenyl]-4-(1-methylethyl)-benzenesulfonamide, sibutramine, topiramate, axokine, dexamphetamine, phentermine, phenylpropanolamine, rimonabant and mazindol.

20. The combination of claim 15 wherein the lipid lowering agent is at least one agent selected from the group consisting of a microsomal triglyceride transfer protein (MTP) inhibitor, cholesterol ester transfer protein, a hydroxy-3-methyl-glutaryl -coenzyme A (HMG CoA) reductase inhibitor, a squalene synthetase inhibitor, a fibric acid derivative, an upregulator of low-density lipoprotein (LDL) receptor activity, a lipoxygenase inhibitor, or an acyl coenzyme A-cholesterol acyltransferase (ACAT) inhibitor.

21. The combination of claim 20 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, N-[2,6-bis(1-methylethyl)phenyl]-2-(tetradecylthio)-acetamide, 3-(13-hydroxy-10-oxotetradecyl)-5,7-dimethoxy-1(3H)-isobenzofuranone, torcetrapib, and (3 alpha, 4 alpha, 5 alpha)-4-(2-propenyl-cholestan-3-ol).

22. A pharmaceutical composition comprising the following structure:
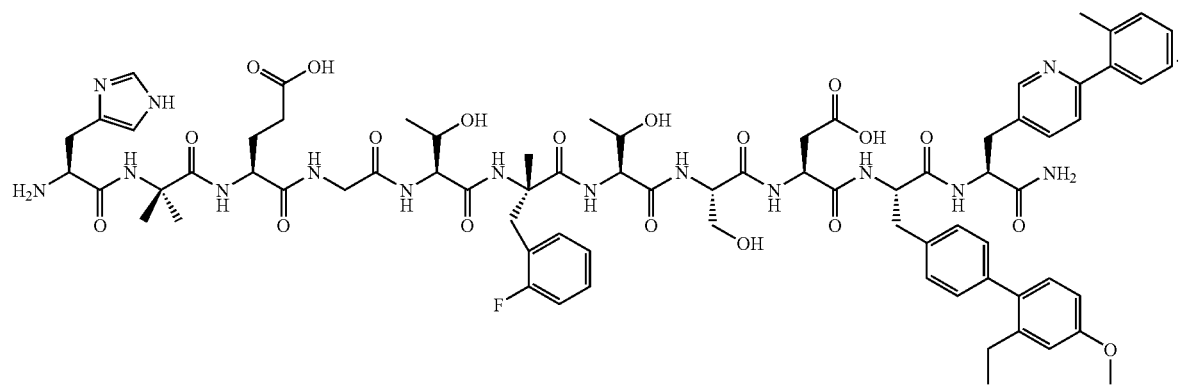
SEQ ID NO:1
* * * * *

SEQUENCE LISTING

```
<160> NUMBER OF SEQ ID NOS: 94

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 1

His Xaa Glu Gly Thr Phe Thr Ser Asp Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 2

His Xaa Glu Gly Thr Phe Thr Ser Asp Xaa Xaa
1               5                   10

<210> SEQ ID NO 3
<211> LENGTH: 11
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 3

His Xaa Glu Gly Thr Phe Thr Ser Asp Xaa Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 4

His Xaa Glu Gly Thr Phe Thr Ser Asp Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
```

```
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2-trifluoromethylphenyl)-3-
      pyridylalanine-NH2

<400> SEQUENCE: 5

His Xaa Glu Gly Thr Phe Thr Ser Asp Xaa Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-trifluoromethylphenyl)-3-
      pyridylalanine-NH2

<400> SEQUENCE: 6

His Xaa Glu Gly Thr Phe Thr Ser Asp Xaa Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-Methyl-5'-fluoro)phenyl)]-3-
      pyridylalanine-NH2

<400> SEQUENCE: 7

His Xaa Glu Gly Thr Phe Thr Ser Asp Xaa Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-methanesulfonylphenyl)-3-
      pyridylalanine-NH2

<400> SEQUENCE: 8

His Xaa Glu Gly Thr Phe Thr Ser Asp Xaa Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: 4-(2'-Methylphenyl)-3-pyridylalanine-NH2

<400> SEQUENCE: 9

His Xaa Glu Gly Thr Phe Thr Ser Asp Xaa Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 10

His Xaa Glu Gly Thr Phe Thr Ser Asp Xaa Xaa
```

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MOD_RES
<222> LOCATION: (5)..(5)
<223> OTHER INFORMATION: Nle
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 11

His Xaa Glu Gly Leu Phe Thr Ser Asp Xaa Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Cl)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 12

His Xaa Glu Gly Thr Phe Thr Ser Asp Xaa Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)

```
<220> FEATURE:
<221> NAME/KEY: MISC_FEATURE
<222> LOCATION: (10)..(10)
<223> OTHER INFORMATION: X is biphenylalanine(2',4'-di-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 13

His Xaa Glu Gly Thr Phe Thr Ser Asp Xaa Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Me-3'-Fluoro)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 14

His Xaa Glu Gly Thr Phe Thr Ser Asp Xaa Xaa
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is Biphenylalanine(2-Me-3-Fluoro)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 15

His Xaa Glu Gly Thr Phe Thr Ser Asp Xaa Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Fluoro)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 16

His Xaa Glu Gly Thr Phe Thr Ser Asp Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[2'-Cl-4'-CF3)-3'-pyridyl]-phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 17

His Xaa Glu Gly Thr Phe Thr Ser Asp Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MOD_RES
<222> LOCATION: (5)..(5)
<223> OTHER INFORMATION: Nva
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

```
<400> SEQUENCE: 18

His Xaa Glu Gly Val Phe Thr Ser Asp Xaa Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-ethylphenyl)-3-pyridylalanine-NH2

<400> SEQUENCE: 19

His Xaa Glu Gly Thr Phe Thr Ser Asp Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-ethylphenyl)-3-pyridylalanine-NH2

<400> SEQUENCE: 20

His Xaa Glu Gly Thr Phe Thr Ser Asp Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
```

```
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 21

His Xaa Glu Gly Thr Phe Thr Ser Asp Xaa Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-Methoxy)-3'-
      pyridyl)phenylalanine-NH2

<400> SEQUENCE: 22

His Xaa Glu Gly Thr Phe Thr Ser Asp Xaa Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-phenyl-3-pyridylalanine-NH2

<400> SEQUENCE: 23

His Xaa Glu Gly Thr Phe Thr Ser Asp Xaa Xaa
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-dimethylphenyl)-3-
      pyridylalanine-NH2

<400> SEQUENCE: 24

His Xaa Glu Gly Thr Phe Thr Ser Asp Xaa Xaa
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3'-chloro-4'-fluoro)phenyl]-3-
      pyridylalanine-NH2

<400> SEQUENCE: 25

His Xaa Glu Gly Thr Phe Thr Ser Asp Xaa Xaa
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3',4'-dimethoxy)phenyl]-3-
      pyridylalanine-NH2

<400> SEQUENCE: 26
```

His Xaa Glu Gly Thr Phe Thr Ser Asp Xaa Xaa
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-ethyl-4'-methoxy)phenyl]-3-
      pyridylalanine-NH2

<400> SEQUENCE: 27

His Xaa Glu Gly Thr Phe Thr Ser Asp Xaa Xaa
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-imidazole-lactyl
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 28

Xaa Xaa Glu Gly Thr Phe Thr Ser Asp Xaa Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:

```
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Isopropoxyphenyl)-3-
      pyridylalanine-NH2

<400> SEQUENCE: 29

His Xaa Glu Gly Thr Phe Thr Ser Asp Xaa Xaa
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl, 5'-Fluoro)phenyl)-3-
      pyridylalanine-NH2

<400> SEQUENCE: 30

His Xaa Glu Gly Thr Phe Thr Ser Asp Xaa Xaa
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Isopropoxyphenyl)-3-
      pyridylalanine-NH2

<400> SEQUENCE: 31

His Xaa Glu Gly Thr Phe Thr Ser Asp Xaa Xaa
1               5                   10
```

```
<210> SEQ ID NO 32
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Methoxyphenyl)-3-pyridylalanine-NH2

<400> SEQUENCE: 32

His Xaa Glu Gly Thr Phe Thr Ser Asp Xaa Xaa
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl, 4'-Fluoro)phenyl)-3-
      pyridylalanine-NH2

<400> SEQUENCE: 33

His Xaa Glu Gly Thr Phe Thr Ser Asp Xaa Xaa
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
```

```
<222> LOCATION: (11)..(11)
<223> OTHER INFORMATION: X is 4-(2'-Methylphenyl)-3-pyridylalanine-NH2

<400> SEQUENCE: 34

His Xaa Glu Gly Thr Phe Thr Ser Asp Xaa Xaa
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Trifluoromethoxyphenyl)-3-
      pyridylalanine-NH2

<400> SEQUENCE: 35

His Xaa Glu Gly Thr Phe Thr Ser Asp Xaa Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Trifluoromethoxyphenyl)-3-
      pyridylalanine-NH2

<400> SEQUENCE: 36

His Xaa Glu Gly Thr Phe Thr Ser Asp Xaa Xaa
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
```

```
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl,4'-Chloro)phenyl)-3-
      pyridylalanine-NH2

<400> SEQUENCE: 37

His Xaa Glu Gly Thr Phe Thr Ser Asp Xaa Xaa
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Me-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 38

His Xaa Glu Gly Thr Phe Thr Ser Asp Xaa Xaa
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Trifluoromethylphenyl)-3-
      pyridylalanine-NH2

<400> SEQUENCE: 39

His Xaa Glu Gly Thr Phe Thr Ser Asp Xaa Xaa
1               5                   10
```

```
<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Fluorophenyl)-3-pyridylalanine-NH2

<400> SEQUENCE: 40

His Xaa Glu Gly Thr Phe Thr Ser Asp Xaa Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Trifluoromethylphenyl)-3-
      pyridylalanine-NH2

<400> SEQUENCE: 41

His Xaa Glu Gly Thr Phe Thr Ser Asp Xaa Xaa
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
```

```
<222> LOCATION: (11)..(11)
<223> OTHER INFORMATION: X is 4-(2'-Chlorophenyl)-3-pyridylalanine-NH2

<400> SEQUENCE: 42

His Xaa Glu Gly Thr Phe Thr Ser Asp Xaa Xaa
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Chlorophenyl)-3-pyridylalanine-NH2

<400> SEQUENCE: 43

His Xaa Glu Gly Thr Phe Thr Ser Asp Xaa Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Isopropylphenyl)-3-
      pyridylalanine-NH2

<400> SEQUENCE: 44

His Xaa Glu Gly Thr Phe Thr Ser Asp Xaa Xaa
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
```

```
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-Methyl-4'-methoxy)phenyl]-3-
      pyridylalanine-NH2

<400> SEQUENCE: 45

His Xaa Glu Gly Thr Phe Thr Ser Asp Xaa Xaa
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Trifluoromethylphenyl)-3-
      pyridylalanine-NH2

<400> SEQUENCE: 46

His Xaa Glu Gly Thr Phe Thr Ser Asp Xaa Xaa
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Chlorophenyl)-3-pyridylalanine-NH2

<400> SEQUENCE: 47

His Xaa Glu Gly Thr Phe Thr Ser Asp Xaa Xaa
1               5                   10

<210> SEQ ID NO 48
```

```
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Pyridyl)-3-pyridylalanine-NH2

<400> SEQUENCE: 48

His Xaa Glu Gly Thr Phe Thr Ser Asp Xaa Xaa
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 49

His Xaa Glu Gly Thr Phe Thr Ser Asp Xaa Xaa
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(6'-Methoxypyridin-3'-yl)-3-
``` pyridylalanine-NH2

<400> SEQUENCE: 50

His Xaa Glu Gly Thr Phe Thr Ser Asp Xaa Xaa
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Isopropylphenyl)-3-
      pyridylalanine-NH2

<400> SEQUENCE: 51

His Xaa Glu Gly Thr Phe Thr Ser Asp Xaa Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methoxyphenyl)-3-pyridylalanine-NH2

<400> SEQUENCE: 52

His Xaa Glu Gly Thr Phe Thr Ser Asp Xaa Xaa
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE

```
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3',5'-di-Fluoro-2'-methoxy)phenyl]-3-
      pyridylalanine-NH2

<400> SEQUENCE: 53

His Xaa Glu Gly Thr Phe Thr Ser Asp Xaa Xaa
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-methylphenyl)-3-pyridylalanine-NH2

<400> SEQUENCE: 54

His Xaa Glu Gly Thr Phe Thr Ser Asp Xaa Xaa
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-fluorophenyl)-3-pyridylalanine-NH2

<400> SEQUENCE: 55

His Xaa Glu Gly Thr Phe Thr Ser Asp Xaa Xaa
1               5                   10

<210> SEQ ID NO 56
<211> LENGTH: 11
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-fluorophenyl)-3-pyridylalanine-NH2

<400> SEQUENCE: 56

His Xaa Glu Gly Thr Phe Thr Ser Asp Xaa Xaa
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 57

His Xaa Glu Gly Thr Phe Thr Ser Asp Xaa Xaa
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 58
```

His Pro Glu Gly Thr Phe Thr Ser Asp Xaa Xaa
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 59

His Ala Glu Gly Thr Phe Thr Ser Asp Xaa Xaa
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 60

His Pro Glu Gly Thr Phe Thr His Asp Xaa Xaa
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE

```
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is (S)-4-(2'-Methylphenyl)-alpha-Me-3-
      pyridylalanine-NH2

<400> SEQUENCE: 61

His Pro Glu Gly Thr Phe Thr Ser Asp Xaa Xaa
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is (S)-4-(2'-Methylphenyl)-alpha-Me-3-
      pyridylalanine-NH2

<400> SEQUENCE: 62

His Xaa Glu Gly Thr Phe Thr Ser Asp Xaa Xaa
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 63

His Pro Glu Gly Thr Phe Thr Ser Asp Xaa Xaa
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 64

His Pro Glu Gly Thr Phe Thr His Asp Xaa Xaa
 1               5                  10

<210> SEQ ID NO 65
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 65

His Pro Glu Gly Thr Phe Thr Ser Asp Xaa Xaa
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 66

His Pro Glu Gly Thr Phe Thr Ser Asp Xaa Xaa
 1               5                  10
```

```
<210> SEQ ID NO 67
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 67

His Pro Glu Gly Thr Phe Thr Ser Asp Xaa Xaa
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 68

His Pro Glu Gly Thr Phe Thr Ser Asp Xaa Xaa
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is N-Me-(L)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
```

```
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 69

His Ala Glu Gly Thr Phe Thr Ser Asp Xaa Xaa
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3,5-
      pyrimidylalanine-NH2

<400> SEQUENCE: 70

His Xaa Glu Gly Thr Phe Thr Ser Asp Xaa Xaa
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 71

His Pro Asp Gly Thr Phe Thr Ser Asp Xaa Xaa
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
```

```
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Ethylphenyl)-3-pyridylalanine-NH2

<400> SEQUENCE: 72

His Pro Glu Gly Thr Phe Thr Ser Asp Xaa Xaa
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 73

His Pro Glu Gly Thr Phe Thr Ser Asp Xaa Xaa
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

```
<400> SEQUENCE: 74

His Pro Glu Gly Thr Phe Thr Ser Asp Xaa Xaa
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 75

His Pro Glu Gly Thr Phe Thr Ser Asp Xaa Xaa
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 76

His Pro Glu Gly Thr Phe Thr Ser Asp Xaa Xaa
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 77

Xaa Xaa Glu Gly Thr Phe Thr Ser Asp Xaa Xaa
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 78

Xaa Xaa Glu Gly Thr Phe Thr His Asp Xaa Xaa
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
```

```
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 79

Xaa Xaa Glu Gly Thr Phe Thr Ser Asp Xaa Xaa
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 80

Xaa Xaa Glu Gly Thr Phe Thr His Asp Xaa Xaa
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 81
```

```
His Pro Glu Gly Thr Phe Thr Ser Asp Xaa Xaa
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 82

His Pro Glu Gly Thr Phe Thr Ser Asp Xaa Xaa
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 83

His Ala Glu Gly Thr Phe Thr Ser Asp Xaa Xaa
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
```

```
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 84

His Ala Glu Gly Thr Phe Thr Ser Asp Xaa Xaa
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3SO2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 85

His Pro Glu Gly Thr Phe Thr Ser Asp Xaa Xaa
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3SO2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
```

```
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 86

His Pro Glu Gly Thr Phe Thr Ser Asp Xaa Xaa
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is L-Lactyl-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 87

His Pro Glu Gly Thr Phe Thr Ser Asp Xaa Xaa
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is L-Lactyl-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 88

His Pro Glu Gly Thr Phe Thr Ser Asp Xaa Xaa
1               5                   10

<210> SEQ ID NO 89
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-di-Me)phenyl)-3-
      pyridylalanine-NH2

<400> SEQUENCE: 89

His Xaa Glu Gly Thr Phe Thr Ser Asp Xaa Xaa
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 90

His Xaa Glu Gly Thr Phe Thr His Asp Xaa Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

<400> SEQUENCE: 91

His Ala Glu Gly Thr Phe Thr Ser Asp Xaa Xaa
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 92

His Xaa His Gly Thr Phe Thr Ser Asp Xaa Xaa
1               5                   10

<210> SEQ ID NO 93
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is biphenylalanine
<220> FEATURE:
<221> NAME/KEY: MISC_FEATURE
<222> LOCATION: (5)..(5)
<223> OTHER INFORMATION: X is phenyl pyridylalanine

<400> SEQUENCE: 93

Thr Ser Asp Xaa Xaa
1               5

<210> SEQ ID NO 94
<211> LENGTH: 11
<212> TYPE: PRT
<213> ORGANISM: Artificial Sequence
<220> FEATURE:
<223> OTHER INFORMATION: Sythetic Peptide

```
-continued

<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 94

His Pro Glu Gly Thr Phe Thr His Asp Xaa Xaa
1               5                   10
```